(12) United States Patent
Himmelsbach et al.

(10) Patent No.: US 7,998,949 B2
(45) Date of Patent: Aug. 16, 2011

(54) BICYCLIC HETEROCYCLES, DRUGS CONTAINING SAID COMPOUNDS, USE THEREOF, AND METHOD FOR PRODUCTION THEREOF

(75) Inventors: Frank Himmelsbach, Mittelbiberach (DE); Birgit Jung, Laupheim (DE); Ralf Lotz, Schemmerhofen (DE); Markus Ostermeier, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/525,742

(22) PCT Filed: Jan. 30, 2008

(86) PCT No.: PCT/EP2008/051141
§ 371 (c)(1),
(2), (4) Date: Oct. 7, 2009

(87) PCT Pub. No.: WO2008/095847
PCT Pub. Date: Aug. 14, 2008

(65) Prior Publication Data
US 2010/0022505 A1    Jan. 28, 2010

(30) Foreign Application Priority Data

Feb. 6, 2007  (EP) .................................... 07101785
Oct. 17, 2007  (EP) .................................... 07118700

(51) Int. Cl.
*A61K 31/517* (2006.01)
(52) U.S. Cl. ........... 514/211.01; 514/212.01; 514/266.4; 540/484; 544/293; 544/358
(58) Field of Classification Search .................... 544/293
See application file for complete search history.

(56) References Cited

U.S. PATENT DOCUMENTS

| | | |
|---|---|---|
| 3,985,749 A | 10/1976 | Foster |
| 4,322,420 A | 3/1982 | Kobayashi et al. |
| 4,335,127 A | 6/1982 | Vandenberk et al. |
| 4,640,920 A | 2/1987 | Boyle et al. |
| 4,845,629 A | 7/1989 | Murga |
| 4,921,863 A | 5/1990 | Sugimoto et al. |
| 5,064,833 A | 11/1991 | Ife et al. |
| 5,252,586 A | 10/1993 | Cain et al. |
| 5,457,105 A | 10/1995 | Barker |
| 5,616,582 A | 4/1997 | Barker |
| 5,642,285 A | 6/1997 | Woo et al. |
| 5,721,237 A | 2/1998 | Myers et al. |
| 5,747,498 A | 5/1998 | Schnur et al. |
| 5,760,041 A | 6/1998 | Wissner et al. |
| 5,770,599 A | 6/1998 | Gibson |
| 5,770,603 A | 6/1998 | Gibson |
| 5,821,246 A | 10/1998 | Brown et al. |
| 5,866,572 A | 2/1999 | Barker et al. |
| 5,929,080 A | 7/1999 | Frost |
| 5,938,706 A | 8/1999 | Feldman |
| 5,962,458 A | 10/1999 | Lohmann et al. |
| 6,004,967 A | 12/1999 | McMahon et al. |
| 6,046,206 A | 4/2000 | Pamukcu et al. |
| 6,117,433 A | 9/2000 | Edens et al. |
| 6,126,917 A | 10/2000 | Mishani et al. |
| 6,177,433 B1 | 1/2001 | Uckun et al. |
| 6,225,318 B1 | 5/2001 | Sobolov-Jaynes et al. |
| 6,270,747 B1 | 8/2001 | Nadel et al. |
| 6,297,258 B1 | 10/2001 | Wissner et al. |
| 6,313,130 B1 | 11/2001 | Uckun et al. |
| 6,326,373 B1 | 12/2001 | Uckun et al. |
| 6,362,336 B1 | 3/2002 | Lohmann et al. |
| 6,384,223 B1 | 5/2002 | Gletsos |
| 6,399,602 B1 | 6/2002 | Barker et al. |
| 6,403,580 B1 | 6/2002 | Himmelsbach et al. |
| 6,414,148 B1 | 7/2002 | Thomas et al. |
| 6,551,989 B2 | 4/2003 | Nadel et al. |
| 6,562,319 B2 | 5/2003 | Mishani et al. |

(Continued)

FOREIGN PATENT DOCUMENTS

CA         2417897 A1      1/2003

(Continued)

OTHER PUBLICATIONS

International Search Report for PCT/EP2008/051141 mailed Jul. 11, 2008.
Singh et al. (1998) "Inhibitors of the epidermal growth factor receptor protein tyrosine kinase: A quantitative structure-activity relationship analysis" J. Enzyme Inhibition 13: 125-134.
Smaill et al. (2000) "Tyrosine kinase inhibitors. 17. Irreversible inhibitors of the epidermalgrowth factor receptor: 4-(Phenylamino)quinazoline- and 4-(Phe-nylamino)pyrido" J Med Chem 43(16): 3199.

(Continued)

*Primary Examiner* — James O Wilson
*Assistant Examiner* — Brian McDowell
(74) *Attorney, Agent, or Firm* — Michael P. Morris; Edward S. Lazer

(57) ABSTRACT

The present invention relates to bicyclic heterocycles of general formula (I)

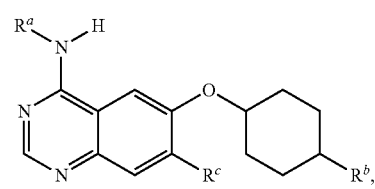

wherein
$R^a$, $R^b$ and $R^c$ are defined as in claim 1, their tautomers, their stereoisomers, their mixtures and their salts, in particular their physiologically acceptable salts with inorganic or organic acids and bases, which have valuable pharmacological properties, in particular an inhibitory action on the signal transduction mediated by tyrosine kinases, their use for the treatment of illnesses, in particular of tumoral diseases and of benign prostatic hyperplasia (BPH), of diseases of the lung and of the airways, and the preparation thereof.

9 Claims, No Drawings

U.S. PATENT DOCUMENTS

| | | | |
|---|---|---|---|
| 6,566,324 B2 | 5/2003 | Nadel et al. |
| 6,617,329 B2 | 9/2003 | Himmelsbach et al. |
| 6,627,634 B2 | 9/2003 | Himmelsbach et al. |
| 6,645,969 B1 | 11/2003 | Myers et al. |
| 6,653,305 B2 | 11/2003 | Himmelsbach et al. |
| 6,656,946 B2 | 12/2003 | Himmelsbach et al. |
| 6,740,561 B2 | 5/2004 | Himmelsbach et al. |
| 6,846,799 B1 | 1/2005 | Nadel et al. |
| 6,924,285 B2 | 8/2005 | Himmelsbach et al. |
| 6,972,288 B1 | 12/2005 | Himmelsbach et al. |
| 7,081,461 B1 | 7/2006 | Mortlock et al. |
| 7,119,084 B2 | 10/2006 | Himmelsbach et al. |
| 7,196,091 B2 | 3/2007 | Himmelsbach et al. |
| 7,354,894 B2 | 4/2008 | Nadel et al. |
| 7,358,222 B2 | 4/2008 | Nadel et al. |
| 7,456,189 B2 | 11/2008 | Himmelsbach et al. |
| 7,531,500 B2 | 5/2009 | Nadel et al. |
| 7,700,547 B2 | 4/2010 | Nadel et al. |
| 2001/0036919 A1 | 11/2001 | Nadel et al. |
| 2001/0041178 A1 | 11/2001 | Nadel et al. |
| 2001/0044435 A1 | 11/2001 | Himmelsbach et al. |
| 2002/0049197 A1 | 4/2002 | Himmelsbach et al. |
| 2002/0082270 A1 | 6/2002 | Himmelsbach et al. |
| 2002/0082271 A1 | 6/2002 | Himmelsbach et al. |
| 2002/0115675 A1 | 8/2002 | Himmelsbach et al. |
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0148990 A1 | 8/2003 | Nadel et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1 | 3/2004 | Himmelsbach et al. |
| 2004/0176361 A1 | 9/2004 | Fujio et al. |
| 2004/0265302 A1 | 12/2004 | Nadel et al. |
| 2005/0014772 A1 | 1/2005 | Himmelsbach et al. |
| 2005/0059661 A1 | 3/2005 | Jung et al. |
| 2005/0070560 A1 | 3/2005 | Himmelsbach et al. |
| 2005/0159436 A1 | 7/2005 | Himmelsbach et al. |
| 2005/0165035 A1 | 7/2005 | Bradbury et al. |
| 2005/0182043 A1 | 8/2005 | Himmelsbach et al. |
| 2005/0215574 A1 | 9/2005 | Bradbury et al. |
| 2006/0063752 A1 | 3/2006 | Himmelsbach et al. |
| 2006/0264450 A1 | 11/2006 | Himmelsbach et al. |
| 2006/0270672 A1 | 11/2006 | Himmelsbach et al. |
| 2007/0135463 A1 | 6/2007 | Himmelsbach et al. |
| 2007/0270330 A1 | 11/2007 | Nadel et al. |
| 2008/0103161 A1 | 5/2008 | Himmelsbach et al. |
| 2008/0175797 A1 | 7/2008 | Nadel et al. |
| 2008/0199462 A1 | 8/2008 | Nadel et al. |
| 2009/0036676 A1 | 2/2009 | Himmelsbach et al. |
| 2009/0203683 A1 | 8/2009 | Himmelsbach et al. |
| 2009/0306072 A1 | 12/2009 | Jung et al. |

FOREIGN PATENT DOCUMENTS

| | | | |
|---|---|---|---|
| CA | 2 476 008 A1 | 10/2003 |
| CA | 2 631 813 A1 | 6/2007 |
| CA | 2669187 A1 | 5/2008 |
| DE | 10042058 A1 | 3/2002 |
| EP | 288563 A1 | 11/1988 |
| EP | 326330 A2 | 8/1989 |
| EP | 520722 A1 | 12/1992 |
| EP | 0566226 A1 | 10/1993 |
| EP | 607439 | 7/1994 |
| EP | 635507 A1 | 1/1995 |
| EP | 0787722 A1 | 8/1997 |
| EP | 837063 A1 | 4/1998 |
| EP | 1230919 A2 | 8/2002 |
| EP | 1283039 A1 | 2/2003 |
| EP | 1369418 A1 | 12/2003 |
| GB | 2033894 A | 5/1980 |
| GB | 2160201 A | 12/1985 |
| GB | 2295387 A | 5/1996 |
| JP | 11-189586 A | 7/1999 |
| WO | 88/02365 A1 | 4/1988 |
| WO | 92/14746 A1 | 9/1992 |
| WO | 92/20642 A1 | 11/1992 |
| WO | 93/08170 A1 | 4/1993 |
| WO | 93/17682 A1 | 9/1993 |
| WO | 602851 A1 | 6/1994 |
| WO | 94/27965 A1 | 12/1994 |
| WO | 95/00146 A1 | 1/1995 |
| WO | 95/03283 A1 | 2/1995 |
| WO | 95/15758 A1 | 6/1995 |
| WO | 95/19169 A2 | 7/1995 |
| WO | 95/24190 A2 | 9/1995 |
| WO | 96/09294 A1 | 3/1996 |
| WO | 96/15118 A1 | 5/1996 |
| WO | 96/16960 A1 | 6/1996 |
| WO | 96/30347 A1 | 10/1996 |
| WO | 96/33977 A1 | 10/1996 |
| WO | 96/33978 A1 | 10/1996 |
| WO | 96/33979 A1 | 10/1996 |
| WO | 96/33980 A1 | 10/1996 |
| WO | 96/33981 A1 | 10/1996 |
| WO | 96/39145 A1 | 12/1996 |
| WO | 97/03069 A1 | 1/1997 |
| WO | 97/11692 A2 | 4/1997 |
| WO | 97/18813 A1 | 5/1997 |
| WO | 97/22596 A1 | 6/1997 |
| WO | 97/30034 A1 | 8/1997 |
| WO | 97/30035 A1 | 8/1997 |
| WO | 97/30044 A1 | 8/1997 |
| WO | 97/32856 A1 | 9/1997 |
| WO | 97/38983 A1 | 10/1997 |
| WO | 97/38994 A1 | 10/1997 |
| WO | 97/42187 A1 | 11/1997 |
| WO | 98/02434 A1 | 1/1998 |
| WO | 98/13354 A1 | 4/1998 |
| WO | 98/19649 A2 | 5/1998 |
| WO | 98/38984 A2 | 9/1998 |
| WO | 98/43960 A1 | 10/1998 |
| WO | 98/50038 A1 | 11/1998 |
| WO | 98/50370 A1 | 11/1998 |
| WO | 99/01467 A2 | 1/1999 |
| WO | 99/06378 A1 | 2/1999 |
| WO | 99/06396 A1 | 2/1999 |
| WO | 99/09016 A1 | 2/1999 |
| WO | 99/10349 A1 | 3/1999 |
| WO | 99/24037 A1 | 5/1999 |
| WO | 99/35132 A1 | 7/1999 |
| WO | 99/61428 A1 | 12/1999 |
| WO | 00/00202 A1 | 1/2000 |
| WO | 00/06555 A1 | 2/2000 |
| WO | 00/09481 A1 | 2/2000 |
| WO | 00/10981 A1 | 3/2000 |
| WO | 00/12497 A2 | 3/2000 |
| WO | 00/18740 A1 | 4/2000 |
| WO | 00/20402 A1 | 4/2000 |
| WO | 00/24718 A1 | 5/2000 |
| WO | 00/44728 A1 | 8/2000 |
| WO | 00/47212 A1 | 8/2000 |
| WO | 00/51587 A2 | 9/2000 |
| WO | 00/51991 A1 | 9/2000 |
| WO | 00/55141 A1 | 9/2000 |
| WO | 00/55162 A2 | 9/2000 |
| WO | 00/56338 A1 | 9/2000 |
| WO | 00/56720 A1 | 9/2000 |
| WO | 00/68201 A1 | 11/2000 |
| WO | 00/68203 A1 | 11/2000 |
| WO | 00/73260 A1 | 12/2000 |
| WO | 00/78735 A1 | 12/2000 |
| WO | 01/04102 A1 | 1/2001 |
| WO | 01/07432 A2 | 2/2001 |
| WO | 01/12227 A1 | 2/2001 |
| WO | 01/21594 A1 | 3/2001 |
| WO | 01/21595 A1 | 3/2001 |
| WO | 01/21596 A1 | 3/2001 |
| WO | 01/21597 A1 | 3/2001 |
| WO | 01/32632 A2 | 5/2001 |
| WO | 01/32651 A1 | 5/2001 |
| WO | 01/45641 A2 | 6/2001 |
| WO | 01/66099 A2 | 9/2001 |
| WO | 01/76586 A1 | 10/2001 |

| | | | |
|---|---|---|---|
| WO | 01/77085 A1 | 10/2001 |
| WO | 01/77104 A1 | 10/2001 |
| WO | 01/94341 A1 | 12/2001 |
| WO | 01/98277 A2 | 12/2001 |
| WO | 02/16352 A1 | 2/2002 |
| WO | 02/18351 A1 | 3/2002 |
| WO | 02/18370 A1 | 3/2002 |
| WO | 02/18373 A1 | 3/2002 |
| WO | 02/18376 A1 | 3/2002 |
| WO | 02/24684 A1 | 3/2002 |
| WO | 0218372 A1 | 3/2002 |
| WO | 02/30924 A1 | 4/2002 |
| WO | 02/34711 A1 | 5/2002 |
| WO | 02/34744 A1 | 5/2002 |
| WO | 02/41882 A2 | 5/2002 |
| WO | 02/44166 A1 | 6/2002 |
| WO | 02/48117 A1 | 6/2002 |
| WO | 02/50043 A1 | 6/2002 |
| WO | 02/056882 A1 | 7/2002 |
| WO | 02/062767 A1 | 8/2002 |
| WO | 02/066445 A1 | 8/2002 |
| WO | 02/068409 A1 | 9/2002 |
| WO | 02/073235 A2 | 9/2002 |
| WO | 02/076976 A2 | 10/2002 |
| WO | 02/092577 A1 | 11/2002 |
| WO | 02/092578 A1 | 11/2002 |
| WO | 02/092579 A1 | 11/2002 |
| WO | 02/094760 A2 | 11/2002 |
| WO | 03/000188 A2 | 1/2003 |
| WO | 03/040108 A1 | 5/2003 |
| WO | 03/404109 A2 | 5/2003 |
| WO | 03/045364 A2 | 6/2003 |
| WO | 03/045395 A1 | 6/2003 |
| WO | 03/049740 A1 | 6/2003 |
| WO | 03/082290 A1 | 10/2003 |
| WO | 03/082831 A1 | 10/2003 |
| WO | 2004/064718 A2 | 8/2004 |
| WO | 2004/093880 A1 | 11/2004 |
| WO | 2005/012290 A1 | 2/2005 |
| WO | 2005/026151 A1 | 3/2005 |
| WO | 2005/026152 A1 | 3/2005 |
| WO | 2005/028469 A1 | 3/2005 |
| WO | 2005/028470 A1 | 3/2005 |
| WO | 2005/030757 A1 | 4/2005 |
| WO | 2005/030765 A1 | 4/2005 |
| WO | 2005/041973 A1 | 5/2005 |
| WO | 2006034015 A1 | 3/2006 |
| WO | 2007/068552 A1 | 6/2007 |
| WO | 2008055854 A1 | 5/2008 |

OTHER PUBLICATIONS

Stamos et al., "Structure of the Epidermal Growth Factor Receptor Kinase Domain Alone and in Complex with a 4-Anilinoquinazoline Inhibitor," J. Bio. Chem. 277(48):46265-46272 (2002).

Tang, Patricia, A., et al; A Review of Erlotinib and its Clinical Use; Expert OpinionPharmacotherapy (2006) vol. 7, No. 2 pp. 177-193.

Traxler, "Monthly Focus: Oncologic, Endocrine & Metabolic: Tyrosine kinase inhibitors in cancer treatment (Part II)," Expert Opinion on Therapeutic Patents 8:1599-1625 (1998).

Traxler, "Oncologic, Endocrine & Metabolic: Protein tyrosine kinase inhibitors in cancer treatment," Expert Opinion on Therapeutic Patents 7:571-588 (1997).

Tsou et al., "6-Substituted-4-(3-bromophenylamino)quinazolines As Putative Irreversible Inhibitors of the Epidermal Growth Factor Receptor (Egfr) and Human Epidermal Growth Factor Receptor (Her-2) Tyrosine Kinases with Enhanced Antitumor Activity," J. Med. Chem 44:2719-2734 (2001).

Vema et al., "Design of EGFR Kinase Inhibitors: A Ligand-Based Approach and Its Confirmation with Structure-Based Studies," Bioorg. Med. Chem. 11:4643-4653 (2003).

Wright et al. (2001) "Allosteric inhibition of fructose-1,6-bisphosphatase by anilinoquinazolines" Bioorg Med Chem Lett. 11(1): 17-21.

B.C. Baguley et al.: "Inhibition of growth of primary human tumor cell cultures by a 4-anilinoquinaziline inhibitor of the epidermal growth factor receptor family of tyrosine kinase", European Journal of Cancer, 1998, vol. 34, No. 7, pp. 1086-1090.

Ballard, Peter et al, "5-Substituted 4-anilinoquinazolines as potent, selective and orally active inhibitors of erbB2 receptor tyrosine kinase," Bioorganic & Medicinal Chemistry Letters 15(19):4226-4229 (2005).

Ballard, Peter et al, "Inhibitors of epidermal growth factor receptor tyrosine kinase: Novel C-5 substituted anilinoquinazolines designed to target the ribose pocket," Bioorganic & Medicinal Chemistry Letters 16(6):1633-1637 (2006).

Ballard, Peter et al, "Inhibitors of epidermal growth factor receptor tyrosine kinase: Optimization of potency and in vivo pharmacokinetics," Bioorganic & Medicinal Chemistry Letters 16(18):4908-4912 (2006).

Barker et al., Studies Leading to the Identification of ZD1839 (IressaTM): An Orally Active, Selective Epidermal Growth Factor Receptor Tyrosine Kinase Inhibitor Targeted to the Treatment of Cancer, Bioorg. Med. Chem. Lett. 11(14): 1911-1914 (2001).

Boschelli, Diane H.; Small Molecule Inhibitors of Receptor Tyrosine Kinases; Review Article; Chemical Sciences (2001) pp. 1-35.

Bridges et al. (1996) "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor" J. Med. Chem.39: 267-276.

Chevalier et al. (1999) "Induction of DNA replication by peroxisome proliferators is independent of both tumour necrosis factor (alpha) priming and EGF-receptor tyrosine kinase activity" J. Cell Sci. 112(24): 4785-4791.

Communication from EPO dated Mar. 9, 2006, in EP Appin. No. 03 710 015.3, the European counterpart of the present application.

Communication from European Patent Office ("EPO") dated May 27, 2005, in EP Appin. No. 03 710 015.3, the European counterpart of the present application.

Communication from European Patent Office in EP Appin. No. 03 710 015.3, the European counterpart of the present application, dated Sep. 22, 2006.

Denny et al., "Structure-Activity Relationships for 4-Anilinoquinazolines as Potent Inhibitors at the ATP Binding Site for the Epidermal Growth Factor Receptor in vitro," Clinical and Experimental Pharmacology and Physiology 23:424-427 (1996).

Drug Chemistry ed. E. Pawelczyk, PZWL, Wassaw, 1986, e.g. chapter 1.2.2.

English translation of Office Action in Chinese Patent Appin. No. 03811739.8, the Chinese counterpart of the present application, dated Jul. 21, 2006.

English Translation of Office Action in Japanese Patent Appin. No. 2003-580299, the Japanese counterpart of the present application, dated May 11, 2006.

English Translation of Response to Office Action in Chinese Patent Appin. No. 03811739.8, the Chinese counterpart of the present application, dated Dec. 5, 2006.

English translation of Response to Office Action in Japanese Patent Appin. No. 2003-580299, the Japanese counterpart of the present application, dated Jul. 28, 2006.

English Translation of Response to Office Action in Japanese Patent Appin. No. 2003-580299, the Japanese counterpart of the present application, dated Oct. 26, 2006.

Gazit et al. (1996) "Tyrophostins IV-Highly Potent Inhibitors . . . Relationship Study of 4-Anilidoquinazolines" Bioorganic & Medicinal Chemistry 4(8): 1203-1207.

Ghosh et al. (1999) "Structure-based design of potent inhibitors of EGF-receptor tyrosine kinase as anti-cancer agents" Anti-Cancer Drug Design 14, 403-410.

Gibson, K.H., et al.: "Epidermal growth factor receptor tyrosine kinase: Structure-activity relationships and antitumor activity of novel quinazolines", Bioorganic & Medicinal Chemistry Letters, 1997, vol. 7, No. 21, pp. 2723-2728.

Goldkorn, Tzipora, et al; EGF-Receptor Phosphorylation and Signaling Are Trageted by H2O2 Redox Stress; Am. J. Respir. Cell Mol. Biol (1998) vol. 19 pp. 786-798.

Harris, Craig et al, "Facile synthesis of 7-amino anilinoquinazolines via direct amination of the quinazoline core," Tetrahedron Letters 46(43):7381-7384 (2005).

Harris, Craig et al, "Selective alkylation of a 6,7-dihydroxyquinazoline," Tetrahedron Letters 46(45):7715-7719 (2005).

Hennequin et al. (1999) "Design and structure-activity relationship of a new class of potent VEGF receptor tyrosine kinaseinhibitors" J. Med. Chem. 42: 5369-5389.

Hennequin et al. (2002) "Novel 4-anilinoquinazolines with C-7 basic side chains. Design and structure activity relationship of a series of potent, orally active, VEGF receptor tyrosine kinase inhibitors" J. Med. Chem. 45: 1300-1312.

Hennequin, Laurent et al, "Novel 4-anilinoquinazolines with C-6 carbon-linked side Synthesis and structure-activity relationship of a series of potent, orally active, EGF receptor tyrosine kinase inhibitors," Bioorganic & Medicinal Chemistry Letters 16(10):2672-2676 (2006).

International Search Report for PCT/EP2004/010723 mailed Mar. 10, 2005.

International Search Report for PCT/EP2006/065000 mailed Feb. 6, 2007.

International Search Report for PCT/EP2006/068598 mailed Mar. 6, 2007.

International Search Report for PCT/EP2007/061842 mailed Apr. 10, 2008.

International Search Report for PCT/EP2009/000805 mailed May 9, 2009.

International Search Report for PCT/EP2009/059511 mailed Sep. 18, 2009.

International Search Report for PCT/EP2009/059519 mailed Sep. 18, 2009.

International Search Report PCT/EP2003/03062 mailed Jun. 6, 2003.

International Search report, PCT/EP/00/02228, Jul. 18, 2000.

International Search Report, UAE/P/209/2001, Apr. 20, 2010.

Mendelsohn (2002) "Targeting the Epidermal Growth Factor Receptor for Cancer Therapy" Journal of Clinical Oncology 20(18s): 2s-13s.

Mendelsohn et al. (2003) "Status of Epidermal Growth Factor Receptor Antagonists in the Biology and Treatment of Cancer" Journal of Clinical Oncology 21(14): 2787-2799.

Myers et al. (1997) "The preparation and SAR of 4-(anilino), 4-(phenoxy), and 4-(thiophenoxy)-quinazolines: inhibitors of p56lck and EGF-R tyrosine kinase activity" Bioorg. Med. Chem. Lett. 7(4): 417-420.

Notices of Allowability and Allowance dated Jul. 26, 2006, in copending U.S. Appl. No. 10/857,342.

Office Action in Indian Patent Appin. No. 2630/DELNP/2004, the Indian counterpart of the present application, dated Apr. 20, 2006.

Pao et al. (2005) "Epidermal Growth Factor Receptor Mutations, Small-Molecule Kinase Inhibitors, and Non-Small-Cell Lung Cancer: Current Knowledge and Future Directions" Journal of Clinical Oncology 23(11):1-13.

pending U.S. Appl. No. 11/487,727, filed Aug. 2, 2006.

Rama Krishna Narla et al.: "4-(3'-Bromo-4'hyroxyphenyl)-amino-6,7-dimethoxyquinazoline: A novel quinazoline derivative with potent cytotoxic activity against human glioblastoma cells", Clinical cancer research,. Jun. 1998, vol. 4, pp. 1405-1414.

Reply to May 27, 2005, Communication from EPO dated Sep. 20, 2005.

Response to Office Action in Chinese Patent Appin. No. 03811739.8, the Chinese counterpart of the present application, dated Dec. 5, 2006.

Response to Office Action in Indian Patent Appin. No. 2630/DELNP/2004, the Indian counterpart of the present application, dated Jul. 24, 2006.

Response to Office Action in Japanese Patent Appin. No. 2003-580299, the Japanese counterpart of the present application, dated Jul. 28, 2006.

Rewcastle et al. (1995) "Tyrosine Kinase Inhibitors. 5 . . . 4-(Phenylamino)quinazolines as Potent . . . Inhibitors of the Tyrosine Kinase Domain of the Epidermal Growth Factor Receptor" J.Med. Chem. 38: 3482-3487.

BICYCLIC HETEROCYCLES, DRUGS CONTAINING SAID COMPOUNDS, USE THEREOF, AND METHOD FOR PRODUCTION THEREOF

This application is the national phase entry under 35 U.S.C. §371 of International Application No. PCT/EP2008/051141, filed Jan. 30, 2008, which claims priority to European Application No. 07101785.9, filed Feb. 6, 2007, and European Application No. 07118700.9, filed Oct. 17, 2007, each of which is hereby incorporated by reference in its entirety.

The present invention relates to bicyclic heterocycles of general formula

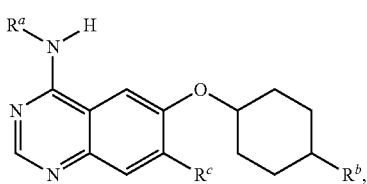

(I)

their tautomers, their stereoisomers, their mixtures and their salts, in particular their physiologically acceptable salts with inorganic or organic acids and bases, which have valuable pharmacological properties, in particular an inhibitory action on the signal transduction mediated by tyrosine kinases, their use for the treatment of illnesses, in particular of tumoral diseases and of benign prostatic hyperplasia (BPH), of diseases of the lung and of the airways, and the preparation thereof.

In the above general formula (I)

$R^a$ denotes a phenyl, 1-phenylethyl or indan-4-yl group, wherein the phenyl nucleus is substituted in each case by the groups $R^1$ to $R^3$, wherein $R^1$ and $R^2$, which may be identical or different, each denote a hydrogen, fluorine, chlorine, bromine or iodine atom,
a $C_{1-4}$-alkyl, hydroxy, $C_{1-4}$-alkoxy, $C_{2-3}$-alkenyl or $C_{2-3}$-alkynyl group,
an aryl, aryloxy, arylmethyl or arylmethoxy group,
a heteroaryl, heteroaryloxy, heteroarylmethyl or heteroarylmethoxy group,
a methyl or methoxy group substituted by 1 to 3 fluorine atoms or
a cyano, nitro or amino group, and $R^3$ denotes a hydrogen, fluorine, chlorine or bromine atom or
a methyl or trifluoromethyl group, $R^b$ denotes an azetidin-1-yl, pyrrolidin-1-yl, piperidin-1-yl, homopiperidin-1-yl, morpholin-4-yl, homomorpholin-4-yl, piperazin-1-yl, 4-($C_{1-4}$-alkyl-carbonyl)-piperazin-1-yl, 4-($C_{1-4}$-alkyl-sulphonyl)-piperazin-1-yl, homopiperazin-1-yl, 4-($C_{1-4}$-alkyl-carbonyl)-homopiperazin-1-yl or 4-($C_{1-4}$-alkyl-sulphonyl)-homopiperazin-1-yl group which may be mono-, di- or trisubstituted by $R^4$ in each case, while the substituents may be identical or different and $R^4$ denotes a fluorine, chlorine, bromine or iodine atom,
a $C_{1-4}$-alkyl, $C_{2-4}$-alkenyl or $C_{2-4}$-alkynyl group,
a methyl or methoxy group substituted by 1 to 3 fluorine atoms,
an amino, $C_{1-4}$-alkylamino, di-($C_{1-4}$-alkyl)amino, $C_{1-4}$-alkyl-carbonylamino, N—($C_{1-4}$-alkyl)-$C_{1-4}$-alkyl-carbonylamino, $C_{1-4}$-alkyl-sulphonylamino or N—($C_{1-4}$-alkyl)-$C_{1-4}$-alkyl-sulphonylamino group,
an amino-$C_{1-4}$-alkyl, $C_{1-4}$-alkylamino-$C_{1-4}$-alkyl, di-($C_{1-4}$-alkyl)amino-$C_{1-4}$-alkyl, $C_{1-4}$-alkyl-carbonylamino-$C_{1-4}$-alkyl, N—($C_{1-4}$-alkyl)-$C_{1-4}$-alkyl-carbonylamino-$C_{1-4}$-alkyl, $C_{1-4}$-alkyl-sulphonylamino-$C_{1-4}$-alkyl or N—($C_{1-4}$-alkyl)-$C_{1-4}$-alkyl-sulphonylamino-$C_{1-4}$-alkyl group,
a hydroxy, $C_{1-4}$-alkyloxy or $C_{1-4}$-alkyl-carbonyloxy group
a hydroxy-$C_{1-4}$-alkyl, $C_{1-4}$-alkyloxy-$C_{1-4}$-alkyl or $C_{1-4}$-alkyl-carbonyloxy-$C_{1-4}$-alkyl group,
a $C_{1-4}$-alkyl-carbonyl, cyano, $C_{1-4}$-alkyl-oxycarbonyl, carboxy, aminocarbonyl, $C_{1-4}$-alkyl-aminocarbonyl, di-($C_{1-4}$-alkyl)amino-carbonyl, pyrrolidin-1-yl-carbonyl, piperidin-1-yl-carbonyl, piperazin-1-yl-carbonyl, 4-$C_{1-4}$-alkyl-piperazin-1-yl-carbonyl or morpholin-4-yl-carbonyl group,
a $C_{1-4}$-alkylcarbonyl-$C_{1-4}$-alkyl, cyano-$C_{1-4}$-alkyl, $C_{1-4}$-alkyloxycarbonyl-$C_{1-4}$-alkyl, aminocarbonyl-$C_{1-4}$-alkyl, $C_{1-4}$-alkylaminocarbonyl-$C_{1-4}$-alkyl, di-($C_{1-4}$-alkyl)aminocarbonyl-$C_{1-4}$-alkyl, pyrrolidin-1-yl-carbonyl-$C_{1-4}$-alkyl, piperidin-1-yl-carbonyl-$C_{1-4}$-alkyl, piperazin-1-yl-carbonyl-$C_{1-4}$-alkyl, 4-$C_{1-4}$-alkyl-piperazin-1-yl-carbonyl-$C_{1-4}$-alkyl or morpholin-4-yl-carbonyl-$C_{1-4}$-alkyl group,
a $C_{1-4}$-alkylsulphanyl, $C_{1-4}$-alkylsulphinyl, $C_{1-4}$-alkylsulphonyl, aminosulphonyl, $C_{1-4}$-alkyl-aminosulphonyl or di-($C_{1-4}$-alkyl)amino-sulphonyl group,
a $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, aminosulphonyl-$C_{1-4}$-alkyl, $C_{1-4}$-alkyl-aminosulphonyl-$C_{1-4}$-alkyl or di-($C_{1-4}$-alkyl)amino-sulphonyl-$C_{1-4}$-alkyl group and wherein the heterocycles mentioned under $R^b$ above may additionally be substituted by an oxo group, $R^c$ denotes a hydrogen atom,
a fluorine, chlorine, bromine or iodine atom,
a $C_{1-4}$-alkyl group,
a $C_{1-4}$-alkyl group which is substituted by an $R^5$ group, where $R^5$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group or
a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group,
a hydroxy group,
a $C_{1-4}$-alkyloxy group,
a methoxy or ethyloxy group substituted by 1 to 3 fluorine atoms,
a $C_{2-4}$-alkyloxy group which is substituted by the group $R^5$, where $R^5$ is as hereinbefore defined,
a $C_{3-7}$-cycloalkyloxy or $C_{3-7}$-cycloalkyl-$C_{1-4}$-alkyloxy group,
a tetrahydrofuran-3-yloxy, tetrahydropyran-3-yloxy or tetrahydropyran-4-yloxy group,
a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^6$, where
  $R^6$ denotes a hydrogen atom or a $C_{1-3}$-alkyl group,
or a $C_{1-4}$-alkoxy group which is substituted by a morpholinyl group substituted in the 4 position by the group $R^6$, where $R^6$ is as hereinbefore defined, and wherein the pyrrolidinyl, piperidinyl, piperazinyl and morpholinyl groups mentioned above in the definition of the group $R^c$ may each be substituted by one or two $C_{1-3}$-alkyl groups, and wherein by the aryl groups mentioned in the definition of the foregoing groups is meant in each case a phenyl group which is mono- or disubstituted by $R^7$, wherein the substituents may be identical or different and
  $R^7$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, and by the heteroaryl groups mentioned in the definition of the foregoing groups is meant a pyridyl, pyridazinyl, pyrimidinyl or pyrazinyl group, wherein the above-mentioned heteroaryl groups are mono- or disubstituted by the group $R^7$, wherein the substituents may be identical or different and $R^7$ is as hereinbefore defined, and unless stated otherwise, the above-mentioned alkyl groups may be straight-chain or branched.

Preferred compounds of the above general formula I are those wherein $R^a$ denotes a phenyl, 1-phenylethyl or indan-4-yl group, wherein the phenyl nucleus is substituted in each case by the groups $R^1$ to $R^3$, wherein
  $R^1$ denotes a hydrogen, fluorine, chlorine or bromine atom, a methyl, trifluoromethyl or ethynyl group,
  a phenyloxy or phenylmethoxy group, wherein the phenyl moiety of the above-mentioned groups may optionally be substituted by a fluorine or chlorine atom, or
  a pyridyloxy or pyridinylmethoxy group, wherein the pyridinyl moiety of the above-mentioned groups is optionally substituted by a methyl or trifluoromethyl group,
  $R^2$ denotes a hydrogen, fluorine or chlorine atom or a methyl group and
  $R^3$ denotes a hydrogen atom,
$R^b$ denotes an azetidin-1-yl, pyrrolidin-1-yl, piperidin-1-yl, homopiperidin-1-yl, morpholin-4-yl, homomorpholin-4-yl, piperazin-1-yl, 4-($C_{1-3}$-alkyl-carbonyl)-piperazin-1-yl, 4-($C_{1-3}$-alkyl-sulphonyl)-piperazin-1-yl, homopiperazin-1-yl, 4-($C_{1-3}$-alkyl-carbonyl)-homopiperazin-1-yl or 4-($C_{1-3}$-alkyl-sulphonyl)-homopiperazin-1-yl group which may be mono- or disubstituted in each case by $R^4$, wherein the substituents may be identical or different and
  $R^4$ denotes a fluorine atom,
  a $C_{1-3}$-alkyl group,
  an amino, $C_{1-3}$-alkylamino, di-($C_{1-3}$-alkyl)amino, $C_{1-3}$-alkyl-carbonylamino, N—($C_{1-3}$-alkyl)-$C_{1-3}$-alkyl-carbonylamino, $C_{1-3}$-alkyl-sulphonylamino or N—($C_{1-3}$-alkyl)-$C_{1-3}$-alkyl-sulphonylamino group,
  an amino-$C_{1-3}$-alkyl, $C_{1-3}$-alkylamino-$C_{1-3}$-alkyl, di-($C_{1-3}$-alkyl)amino-$C_{1-3}$-alkyl, $C_{1-3}$-alkyl-carbonylamino-$C_{1-3}$-alkyl, N—($C_{1-3}$-alkyl)-$C_{1-3}$-alkyl-carbonylamino-$C_{1-3}$-alkyl, $C_{1-3}$-alkyl-sulphonylamino-$C_{1-3}$-alkyl or N—($C_{1-3}$-alkyl)-$C_{1-3}$-alkyl-sulphonylamino-$C_{1-3}$-alkyl group,
  a hydroxy, $C_{1-3}$-alkyloxy or $C_{1-3}$-alkyl-carbonyloxy group,
  a hydroxy-$C_{1-3}$-alkyl, $C_{1-3}$-alkyloxy-$C_{1-3}$-alkyl or $C_{1-3}$-alkyl-carbonyloxy-$C_{1-3}$-alkyl group,
  a $C_{1-3}$-alkyl-carbonyl, cyano, $C_{1-4}$-alkyl-oxycarbonyl, carboxy, aminocarbonyl, $C_{1-3}$-alkyl-aminocarbonyl or di-($C_{1-3}$-alkyl)amino-carbonyl-group,
  a $C_{1-3}$-alkylcarbonyl-$C_{1-3}$-alkyl, cyano-$C_{1-3}$-alkyl, $C_{1-4}$-alkyloxycarbonyl-$C_{1-3}$-alkyl-group, aminocarbonyl-$C_{1-3}$-alkyl, $C_{1-3}$-alkylaminocarbonyl-$C_{1-3}$-alkyl or di-($C_{1-3}$-alkyl)aminocarbonyl-$C_{1-3}$-alkyl group,
  a $C_{1-4}$-alkylsulphanyl, $C_{1-4}$-alkylsulphinyl, $C_{1-4}$-alkylsulphonyl, aminosulphonyl, $C_{1-3}$-alkyl-aminosulphonyl or di-($C_{1-3}$-alkyl)amino-sulphonyl group,
  a $C_{1-4}$-alkylsulphanyl-$C_{1-3}$-alkyl, $C_{1-4}$-alkylsulphinyl-$C_{1-3}$-alkyl, $C_{1-4}$-alkylsulphonyl-$C_{1-3}$-alkyl, aminosulphonyl-$C_{1-3}$-alkyl, $C_{1-3}$-alkyl-aminosulphonyl-$C_{1-3}$-alkyl or di-($C_{1-3}$-alkyl)amino-sulphonyl-$C_{1-3}$-alkyl group, and wherein the heterocycles mentioned above under $R^b$—may additionally be substituted by an oxo group,
$R^c$ denotes a hydrogen atom,
  a hydroxy group,
  a $C_{1-3}$-alkyloxy group,
  a methoxy group which is substituted by one to three fluorine atoms,
  an ethyloxy group which is substituted in the 2 position by an $R^5$ group, wherein
    $R^5$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, morpholin-4-yl, homomorpholin-4-yl, piperazin-1-yl or a 4-$C_{1-3}$-alkyl-piperazin-1-yl group,
  a propyloxy group which is substituted in the 3 position by the group $R^5$, wherein $R^5$ is as hereinbefore defined, or
  a butyloxy group which is substituted in the 4 position by a group $R^5$, wherein $R^5$ is as hereinbefore defined, and
wherein, unless stated otherwise, the above-mentioned alkyl groups may be straight-chain or branched,
the tautomers, the stereoisomers, the mixtures thereof and salts thereof.

Particularly preferred compounds of the above general formula I are those wherein $R^a$ denotes a 1-phenylethyl, 3-ethynylphenyl, 3-bromo-2-fluoro-phenyl, 3-bromo-4-fluoro-phenyl, 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 2,5-difluoro-3-methyl-phenyl, 3-chloro-2-methyl-phenyl or an indan-4-yl group,
a 3-chloro-4-benzyloxy-phenyl, 3-chloro-4-[(3-fluoro-benzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyridin-3-yl)oxy]-phenyl group,
$R^b$ denotes an azetidin-1-yl, pyrrolidin-1-yl, piperidin-1-yl, morpholin-4-yl, piperazin-1-yl, 4-($C_{1-3}$-alkyl-carbonyl)-piperazin-1-yl or 4-($C_{1-3}$-alkyl-sulphonyl)-piperazin-1-yl group which may be mono- or disubstituted in each case by $R^4$, wherein the substituents may be identical or different and
$R^4$ denotes a fluorine atom,
  a $C_{1-3}$-alkyl group,
  an amino, $C_{1-3}$-alkylamino, di-($C_{1-3}$-alkyl)amino, $C_{1-3}$-alkyl-carbonylamino, N—($C_{1-3}$-alkyl)-$C_{1-3}$-alkyl-carbonylamino, $C_{1-3}$-alkyl-sulphonylamino or N—($C_{1-3}$-alkyl)-$C_{1-3}$-alkyl-sulphonylamino group,
  an amino-$C_{1-3}$-alkyl, $C_{1-3}$-alkylamino-$C_{1-3}$-alkyl, di-($C_{1-3}$-alkyl)amino-$C_{1-3}$-alkyl, $C_{1-3}$-alkyl-carbonylamino-$C_{1-3}$-alkyl, N—($C_{1-3}$-alkyl)-$C_{1-3}$-alkyl-carbonylamino-$C_{1-3}$-alkyl, $C_{1-3}$-alkyl-sulphonylamino-$C_{1-3}$-alkyl or N—($C_{1-3}$-alkyl)-$C_{1-3}$-alkyl-sulphonylamino-$C_{1-3}$-alkyl group, a hydroxy, $C_{1-3}$-alkyloxy or $C_{1-3}$-alkyl-carbonyloxy group, a hydroxy-$C_{1-3}$-alkyl, $C_{1-3}$-alkyloxy-$C_{1-3}$-alkyl or $C_{1-3}$-alkyl-carbonyloxy-$C_{1-3}$-alkyl group, a $C_{1-3}$-alkyl-carbonyl, cyano, $C_{1-4}$-alkyl-oxycarbonyl, carboxy, aminocarbonyl, $C_{1-3}$-alkyl-aminocarbonyl or di-($C_{1-3}$-alkyl)amino-carbonyl group, a $C_{1-3}$-alkylcarbonyl-$C_{1-3}$-alkyl, cyano-$C_{1-3}$-alkyl, $C_{1-4}$-alkyloxycarbonyl-$C_{1-3}$-alkyl-group, aminocarbonyl-$C_{1-3}$-alkyl, $C_{1-3}$-alkylaminocarbonyl-$C_{1-3}$-alkyl or di-($C_{1-3}$-alkyl)aminocarbonyl-$C_{1-3}$-alkyl group, a $C_{1-4}$-alkylsulphanyl, $C_{1-4}$-alkylsulphinyl, $C_{1-4}$-alkylsulphonyl, aminosulphonyl, $C_{1-3}$-alkyl-aminosulphonyl or di-($C_{1-3}$-alkyl)amino-sulphonyl group, a $C_{1-4}$-alkylsulphanyl-$C_{1-3}$-alkyl, $C_{1-4}$-alkylsulphinyl-$C_{1-3}$-alkyl, $C_{1-4}$-alkylsulphonyl-$C_{1-3}$-alkyl, aminosulphonyl-$C_{1-3}$-alkyl, $C_{1-3}$-alkyl-aminosulphonyl-$C_{1-3}$-alkyl or di-($C_{1-3}$-alkyl)amino-sulphonyl-$C_{1-3}$-alkyl group, and wherein the heterocycles mentioned above under $R^b$ may additionally be substituted by an oxo group, $R^c$ denotes a hydrogen atom, a methoxy or ethyloxy group, an ethyloxy group which is substituted in the 2 position by the group $R^5$, wherein $R^5$ denotes a hydroxy, methoxy, ethoxy, amino, dimethylamino, diethylamino, bis-(2-methoxyethyl)-amino, pyrrolidin-1-yl, piperidin-1-yl, morpholin-4-yl, homomorpholin-4-yl, piperazin-1-yl, 4-methylpiperazin-1-yl or 4-ethylpiperazin-1-yl group, a propyloxy group which is substituted in the 3 position by the group $R^5$, wherein $R^5$ is as hereinbefore defined, or a butyloxy group which is substituted in the 4 position by the group $R^5$, wherein $R^5$ is as hereinbefore defined, and wherein, unless stated otherwise, the above-mentioned alkyl groups may be straight-chain or branched, the tautomers, the stereoisomers, the mixtures thereof and salts thereof.

Most particularly preferred compounds of general formula I are those wherein $R^a$ denotes a 1-phenylethyl, 3-ethynylphenyl, 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 2,5-difluoro-3-methyl-phenyl, 3-chloro-2-methyl-phenyl or an indan-4-yl group, $R^b$ denotes an azetidin-1-yl, pyrrolidin-1-yl, piperidin-1-yl, morpholin-4-yl, piperazin-1-yl, 4-($C_{1-3}$-alkyl-carbonyl)-piperazin-1-yl or 4-($C_{1-3}$-alkyl-sulphonyl)-piperazin-1-yl group which may be mono- or disubstituted in each case by $R^4$, wherein the substituents may be identical or different and $R^4$ denotes a fluorine atom, a $C_{1-3}$-alkyl group, an amino, $C_{1-2}$-alkylamino, di-($C_{1-2}$-alkyl)amino, $C_{1-2}$-alkyl-carbonylamino, N—($C_{1-2}$-alkyl)-$C_{1-2}$-alkyl-carbonylamino, $C_{1-2}$-alkyl-sulphonylamino or N—($C_{1-2}$-alkyl)-$C_{1-2}$-alkyl-sulphonylamino group, an amino-$C_{1-2}$-alkyl, $C_{1-2}$-alkylamino-$C_{1-2}$-alkyl, di-($C_{1-2}$-alkyl)amino-$C_{1-2}$-alkyl, $C_{1-2}$-alkyl-carbonylamino-$C_{1-2}$-alkyl, N—($C_{1-2}$-alkyl)-$C_{1-2}$-alkyl-carbonylamino-$C_{1-2}$-alkyl, $C_{1-2}$-alkyl-sulphonylamino-$C_{1-2}$-alkyl or N—($C_{1-2}$-alkyl)-$C_{1-2}$-alkyl-sulphonylamino-$C_{1-2}$-alkyl group, a hydroxy, $C_{1-2}$-alkyloxy or $C_{1-2}$-alkyl-carbonyloxy group, a hydroxy-$C_{1-2}$-alkyl, $C_{1-2}$-alkyloxy-$C_{2-4}$-alkyl or $C_{1-2}$-alkyl-carbonyloxy-$C_{1-2}$-alkyl group, a $C_{1-2}$-alkyl-carbonyl, cyano, $C_{1-2}$-alkyl-oxycarbonyl, carboxy, aminocarbonyl, $C_{1-2}$-alkyl-aminocarbonyl or di-($C_{1-2}$-alkyl)amino-carbonyl group, a $C_{1-2}$-alkylcarbonyl-$C_{1-2}$-alkyl, cyano-$C_{1-2}$-alkyl, $C_{1-2}$-alkyloxycarbonyl-$C_{1-2}$-alkyl group, aminocarbonyl-$C_{1-2}$-alkyl, $C_{1-2}$-alkylaminocarbonyl-$C_{1-2}$-alkyl or di-($C_{1-2}$-alkyl) aminocarbonyl-$C_{1-2}$-alkyl group, a $C_{1-2}$-alkylsulphanyl, $C_{1-2}$-alkylsulphinyl or $C_{1-2}$-alkylsulphonyl group, a $C_{1-2}$-alkylsulphanyl-$C_{1-2}$-alkyl, $C_{1-2}$-alkylsulphinyl-$C_{1-2}$-alkyl or $C_{1-2}$-alkylsulphonyl-$C_{1-2}$-alkyl group, and wherein the heterocycles mentioned above under $R^b$ may additionally be substituted by an oxo group, $R^c$ denotes a hydrogen atom, a methoxy, ethyloxy or 2-(methoxy)-ethyloxy group, a 2-(morpholin-4-yl)ethyloxy, 3-(morpholin-4-yl)propyloxy or 4-(morpholin-4-yl) butyloxy group, the tautomers, the stereoisomers, the mixtures thereof and salts thereof.

Particularly preferred compounds of general formula I are those wherein $R^a$ denotes a 1-phenylethyl, 3-chloro-2-fluoro-phenyl, 3-4-fluoro-phenyl, 5- chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 3-chloro-2-methyl-phenyl or an indan-4-yl group, $R^b$ denotes an azetidin-1-yl, pyrrolidin-1-yl, piperidin-1-yl, morpholin-4-yl or 3-oxo-piperazin-1-yl group which may be mono- or disubstituted in each case by $R^4$, wherein the substituents may be identical or different and $R^4$ denotes a methyl, hydroxy, cyano, aminocarbonyl, methylamino-carbonyl or dimethylamino-carbonyl group, and $R^c$ denotes a methoxy group, the tautomers, the stereoisomers, the mixtures thereof and salts thereof.

Of the bicyclic heterocycles of general formula I described hereinbefore and the subgroups designated in each case as being preferred, particularly preferred, most particularly preferred and especially preferred, special emphasis should be placed in each case on those compounds wherein $R^a$ denotes a 3-chloro-2-fluoro-phenyl group, a 2-fluoro-3-methyl-phenyl group, a 2-fluoro-5-methyl-phenyl group or a 3-chloro-2-methyl-phenyl group, $R^b$ denotes a 3-oxo-piperazin-1-yl group or a 4-methyl-3-oxo-piperazin-1-yl group, and $R^c$ denotes a methoxy group, wherein for $R^a$ the 3-chloro-2-fluoro-phenyl group in particular, for $R^b$ the 3-oxo-piperazin-1-yl or 4-methyl-3-oxo-piperazin-1-yl group and for $R^c$ the methoxy group deserves special mention, and wherein the trans arrangement of the substituents in the 1,4 position of the cyclohexane ring is preferred in each case.

The following particularly preferred compounds of general formula I deserve particular mention:

(a) 4-[(3-chloro-2-fluoro-phenyl)amino]-6-[cis-4-(morpholin-4-yl)-cyclohexyloxy]-7-methoxy-quinazoline, (b) 4-[(3-chloro-2-fluoro-phenyl)amino]-6-[trans-4-(morpholin-4-yl)-cyclohexyloxy]-7-methoxy-quinazoline, (c) 4-[(3-chloro-2-fluoro-phenyl)amino]-6-[(R)-cis-4-(3-hydroxy-pyrrolidin-1-yl)-cyclohexyloxy]-7-methoxy-quinazoline, (d) 4-[(3-chloro-2-fluoro-phenyl)amino]-6-[(R)-trans-4-(3-hydroxy-pyrrolidin-1-yl)-cyclohexyloxy]-7-methoxy-quinazoline,
(e) 4-[(3-chloro-2-fluoro-phenyl)amino]-6-[(S)-cis-4-(3-hydroxy-pyrrolidin-1-yl)-cyclohexyloxy]-7-methoxy-quinazoline,
(f) 4-[(3-chloro-2-fluoro-phenyl)amino]-6-[(S)-trans-4-(3-hydroxy-pyrrolidin-1-yl)-cyclohexyloxy]-7-methoxy-quinazoline,
(g) 4-[(3-chloro-2-fluoro-phenyl)amino]-6-[cis-4-(3-oxo-piperazin-1-yl)-cyclohexyloxy]-7-methoxy-quinazoline,
(h) 4-[(3-chloro-2-fluoro-phenyl)amino]-6-[trans-4-(3-oxo-piperazin-1-yl)-cyclohexyloxy]-7-methoxy-quinazoline,
(i) 4-[(3-chloro-2-fluoro-phenyl)amino]-6-{(S)-cis-4-[2-(N,N-dimethylaminocarbonyl)-pyrrolidin-1-yl]-cyclohexyloxy]-7-methoxy-quinazoline,
(j) 4-[(3-chloro-2-fluoro-phenyl)amino]-6-{(S)-trans-4-[2-(N,N-dimethylaminocarbonyl)-pyrrolidin-1-yl]-cyclohexyloxy]-7-methoxy-quinazoline,
(k) 4-[(3-chloro-2-fluoro-phenyl)amino]-6-{(S)-cis-4-[2-(aminocarbonyl)-pyrrolidin-1-yl]-cyclohexyloxy]-7-methoxy-quinazoline,
(l) 4-[(3-chloro-2-fluoro-phenyl)amino]-6-{(S)-trans-4-[2-(aminocarbonyl)-pyrrolidin-1-yl]-cyclohexyloxy]-7-methoxy-quinazoline,
(m) 4-[(3-chloro-2-fluoro-phenyl)amino]-6-[trans-4-(4-methyl-3-oxo-piperazin-1-yl)-cyclohexyloxy]-7-methoxy-quinazoline,
(n) 4-[(2-fluoro-3-methyl-phenyl)amino]-6-[trans-4-(3-oxo-piperazin-1-yl)-cyclohexyloxy]-7-methoxy-quinazoline,
(o) 4-[(2-fluoro-5-methyl-phenyl)amino]-6-[trans-4-(3-oxo-piperazin-1-yl)-cyclohexyloxy]-7-methoxy-quinazoline,
(p) 4-[(2,4-difluoro-3-methyl-phenyl)amino]-6-[trans-4-(3-oxo-piperazin-1-yl)-cyclohexyloxy]-7-methoxy-quinazoline and
(q) 4-[(3-chloro-2-methyl-phenyl)amino]-6-[trans-4-(3-oxo-piperazin-1-yl)-cyclohexyloxy]-7-methoxy-quinazoline
and the salts thereof.

The compounds of general formula I may be prepared for example by the following methods:

a) reacting a compound of general formula

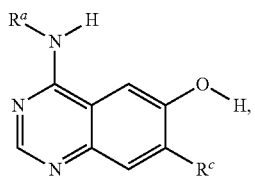
(II)

wherein
$R^a$ and $R^c$ are as hereinbefore defined, with a compound of general formula

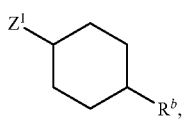
(III)

wherein
$R^b$ is as hereinbefore defined and $Z^1$ denotes a leaving group such as a halogen atom, e.g. a chlorine or bromine atom, a sulphonyloxy group such as a methanesulphonyloxy or p-toluenesulphonyloxy group or a hydroxy group.

With a compound of general formula (III), wherein $Z^1$ denotes a halogen atom or a sulphonyloxy group, the reaction is expediently carried out in a solvent such as ethanol, isopropanol, acetonitrile, toluene, tetrahydrofuran, dioxane, dimethylformamide, dimethylsulphoxide or N-methylpyrrolidinone, preferably in the presence of a base such as potassium carbonate, potassium-tert-butoxide, sodium hydride or N-ethyl-diisopropylamine, at temperatures in the range from 20° C. to 160° C., for example at temperatures in the range from 80° C. to 140° C.

With a compound of general formula III wherein $Z^1$ denotes a hydroxy group, the reaction is carried out in the presence of a dehydrating agent, preferably in the presence of a phosphine and an azodicarboxylic acid derivative such as e.g. Triphenylphosphine/diethyl azodicarboxylate, conveniently in a solvent such as methylene chloride, acetonitrile, tetrahydrofuran, dioxane, toluene or ethyleneglycol diethyl-ether at temperatures between −50 and 150° C., but preferably at temperatures between −20 and 80° C.

b) reacting a compound of general formula

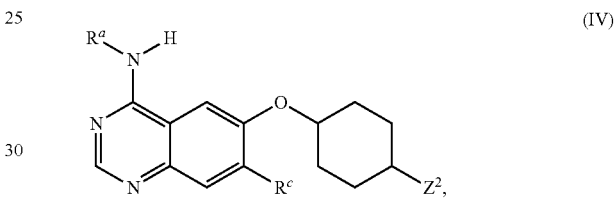
(IV)

wherein
$R^a$ and $R^c$ are as hereinbefore defined, and $Z^2$ denotes a leaving group such as a halogen atom, e.g. a chlorine or bromine atom or a sulphonyloxy group such as a methanesulphonyloxy or p-toluenesulphonyloxy group, with a compound of general formula H—$R^b$, (V)

wherein
$R^b$ is as hereinbefore defined.

The reaction is preferably carried out in the presence of an organic or inorganic base such as potassium carbonate or N-ethyl-diisopropylamine, for example, in a solvent such as ethanol, isopropanol, acetonitrile, toluene, tetrahydrofuran, dioxane, dimethylformamide, dimethylsulphoxide or N-methylpyrrolidinone at temperatures in the range from 0° C. and 150° C.

c) reacting a compound of general formula

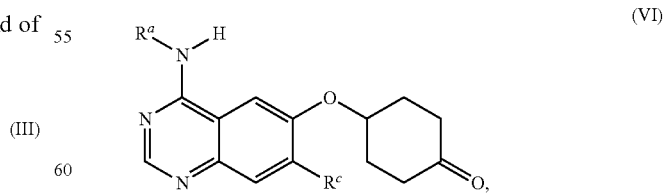
(VI)

wherein
$R^a$ and $R^c$ are as hereinbefore defined, with a compound of general formula H—$R^b$, (VII)

wherein
$R^b$ is as hereinbefore defined, in the presence of a reducing agent.

The reductive amination is carried out for example in a solvent such as dichloromethane, 1,2-dichloroethane, methanol, ethanol, tetrahydrofuran or dioxane in the presence of a reducing agent such as sodium triacetoxyborohydride or sodium cyanoborohydride, optionally in the presence of acetic acid at temperatures between 0° C. and 80° C. The reductive amination may also be carried out with hydrogen in the presence of a catalyst such as palladium on activated charcoal or platinum oxide. Another possibility is to form the enamine from the ketone of general formula VI and the amine of general formula VII while cleaving water, for example with titanium (IV) isopropoxide, and then to reduce this, for example with sodium borohydride or hydrogen/palladium on activated charcoal.

d) reacting a compound of general formula (VIII)

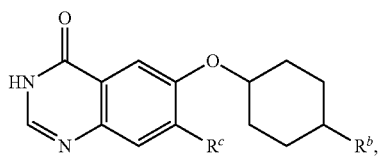

(VIII)

wherein $R^b$ and $R^c$ are as hereinbefore defined, with a halogenating agent, for example an acid halide such as thionyl chloride, thionylbromide, phosphorus trichloride, phosphorus pentachloride or phosphorus oxychloride, to obtain an intermediate compound of general formula (IX),

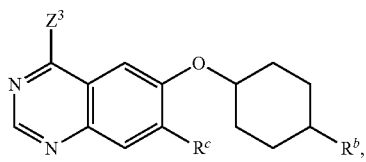

(IX)

wherein $R^b$ and $R^c$ are as hereinbefore defined and $Z^3$ denotes a halogen atom such as a chlorine or bromine atom,
and subsequently reacting with a compound of general formula (X),
$R^a$—$NH_2$ (X), wherein $R^a$ is as hereinbefore defined, or the salts thereof.

The reaction with the halogenating agent is optionally carried out in a solvent such as methylene chloride, chloroform, acetonitrile or toluene and optionally in the presence of a base such as N,N-diethylaniline, triethylamine or N-ethyl-diisopropylamine at temperatures in the range from 20° C. to 160° C., preferably 40° C. to 120° C. However, the reaction is preferably carried out with thionyl chloride and catalytic amounts of dimethylformamide at the boiling temperature of the reaction mixture or with phosphorus oxychloride in acetonitrile in the presence of triethylamine at the boiling temperature of the reaction mixture.

The reaction of the compound of general formula (IX) with the compound of general formula (X) or the salts thereof is conveniently carried out in a solvent such as ethanol, isopropanol, acetonitrile, dioxane or dimethylformamide, optionally in the presence of a base such as potassium carbonate, triethylamine or N-ethyl-diisopropylamine, at temperatures in the range from 20° C. and 160° C., preferably from 60° C. to 120° C. However, the reaction is preferably carried out in isopropanol at the boiling temperature of the reaction mixture.

The reaction of a compound of general formula (VIII) to form a compound of general formula (I) may also be carried out as a one-pot reaction, for example in acetonitrile in the presence of triethylamine.

e) in order to prepare compounds of general formula I wherein $R^c$ denotes one of the above-mentioned, optionally substituted alkyloxy groups:

reacting a compound of general formula

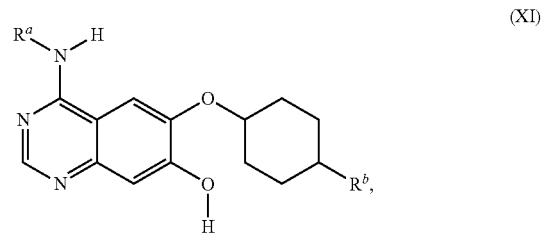

(XI)

wherein $R^a$ and $R^b$ are defined as mentioned hereinbefore, with a compound of general formula $$Z^4\text{—}R^{c'} \quad (XII)$$

wherein $R^{c'}$ denotes a $C_{1-4}$-alkyl group, a methyl or ethyl group substituted by 1 to 3 fluorine atoms, a $C_{3-7}$-cycloalkyl or $C_{3-7}$-cycloalkyl-$C_{1-4}$-alkyl group, a tetrahydrofuran-3-yl, tetrahydropyran-3-yl or tetrahydropyran-4-yl group, a tetrahydrofuranyl-$C_{1-4}$-alkyl or tetrahydropyranyl-$C_{1-4}$-alkyl group, a $C_{2-4}$-alkyl group substituted by $R^7$, wherein $R^7$ is as hereinbefore defined, a $C_{1-4}$-alkyl group which is substituted by a pyrrolidinyl, piperidinyl or homopiperidinyl group substituted in the 1 position by the group $R^8$, or a $C_{1-4}$-alkyl group which is substituted by a morpholinyl group substituted in the 4 position by the group $R^8$, wherein $R^8$ in each case is as hereinbefore defined, and $Z^4$ denotes a leaving group such as a halogen atom, an alkylsulphonyloxy, arylsulphonyloxy or a hydroxy group.

If the leaving group is a halogen atom such as a chlorine, bromine or iodine atom or an alkylsulphonyloxy or arylsulphonyloxy group such as the methanesulphonyloxy or p-toluenesulphonyloxy group, the reaction is preferably carried out in the presence of an organic or inorganic base such as potassium carbonate, sodium hydride or N-ethyl-diisopropylamine. If the leaving group is a hydroxy group, the reaction is carried out in the presence of a dehydrating agent, preferably in the presence of a phosphine and an azodicarboxylic acid derivative such as e.g. Triphenyl phosphine/diethyl azodicarboxylate.

f) in order to prepare compounds of general formula I wherein $R^c$ denotes one of the above-mentioned alkyloxy groups which is substituted by an optionally substituted amino, alkylamino or dialkylamino group or by an optionally substituted heterocyclic group bound via an imino nitrogen atom:

reacting a compound of general formula

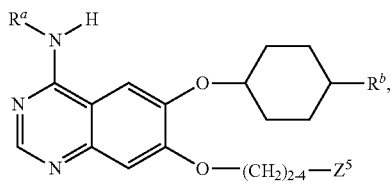
(XIII)

wherein $R^a$ and $R^b$ are as hereinbefore defined and $Z^5$ denotes a leaving group such as a halogen atom, e.g. a chlorine or bromine atom or a sulphonyloxy group such as a methanesulphonyloxy or p-toluenesulphonyloxy group, with ammonia, a corresponding, optionally substituted alkylamine, dialkylamine or an imino compound or the suitable salts or derivatives thereof, such as morpholine, for example.

g) In order to prepare compounds of general formula I wherein $R^b$ contains one or more hydroxy groups:
cleaving protective groups from a compound of general formula

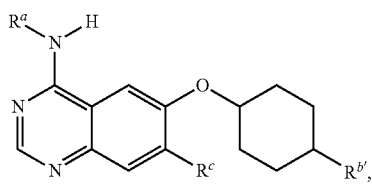
(XIV)

wherein $R^a$ and $R^c$ are as hereinbefore defined and $R^{b'}$ contains one or more groups that can be converted into hydroxy groups, for example an optionally substituted benzyloxy group, a silyloxy, acetyloxy, benzoyloxy, methoxy, ethoxy, tert-butoxy or trityloxy group.

The protective groups are cleaved, for example, hydrolytically in an aqueous solvent, e.g. In water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. In the presence of iodotrimethylsilane, at temperatures between 0 and 120° C., preferably at temperatures between 10 and 100° C.

A benzyl or methoxybenzyl group is cleaved, for example, hydrogenolytically, e.g. With hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and under a hydrogen pressure of 1 to 7 bar, but preferably from 3 to 5 bar. A 2,4-dimethoxybenzyl group however is preferably cleaved in trifluoroacetic acid in the presence of anisole.

A tert.-butyl or benzyl group is cleaved for example by treating with an acid such as trifluoroacetic acid, hydrochloric acid or hydrobromic acid or by treating with iodotrimethylsilane, optionally using a solvent such as methylene chloride, dioxane, methanol or diethyl ether.

A silyloxy group, for example a tert.-butyl-dimethylsilyl group, is cleaved for example by treating with fluorides such as tetrabutylammonium fluoride, optionally using a solvent such as tetrahydrofuran or dioxane.

h) in order to prepare compounds of general formula I wherein $R^b$ contains an —NH— group:
cleaving a protective group from a compound of general formula

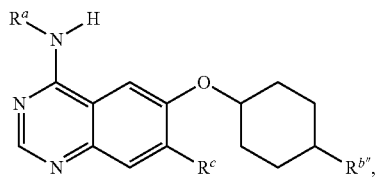
(XV)

wherein $R^a$ and $R^c$ are as hereinbefore defined and $R^{b''}$ has the meanings given for $R^b$ hereinbefore, with the proviso that $R^{b''}$ contains a protected nitrogen atom.

Conventional protecting groups for an amino, alkylamino or imino group include for example the formyl, acetyl, trifluoroacetyl, ethoxycarbonyl, tert.-butoxycarbonyl, benzyloxycarbonyl, benzyl, methoxybenzyl or 2,4-dimethoxybenzyl group, while additionally the phthalyl group may be used for the amino group.

The protective group is cleaved for example by hydrolysis in an aqueous solvent, e.g. In water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

A benzyl, methoxybenzyl or benzyloxycarbonyl group, however, is cleaved by hydrogenolysis, for example, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and under a hydrogen pressure of 1 to 7 bar, but preferably from 3 to 5 bar.

A 2,4-dimethoxybenzyl group, however, is preferably cleaved in trifluoroacetic acid in the presence of anisole.

A tert.-butyl or tert.-butyloxycarbonyl group is preferably cleaved by treatment with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably carried out by treatment with an acid such as hydrochloric acid, optionally in the presence of a solvent such as acetic acid at temperatures between 50 and 120° C. or by treatment with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine, n-butylamine or ethanolamine in a solvent such as methanol, ethanol, isopropanol, toluene/water or dioxane at temperatures between 20 and 50° C.

If according to the invention a compound of general formula I is obtained which contains an amino, alkylamino or imino group, this may be converted by acylation or sulphonylation into a corresponding acyl or sulphonyl compound of general formula I, wherein the acylating agents used may be, for example, carboxylic acid halides, carboxylic acid anhydrides and carboxylic acids with activating agents such as N,N'-carbonyldiimidazole, N,N'-dicyclohexylcarbodiimide or O-(benzotriazol-1-yl)-N,N,N'N'-tetramethyluronium tetrafluoroborate and the sulphonylating agents used may be sulphonylhalides, and/or if a compound of general formula I is obtained which contains an amino, alkylamino or imino group, this may be converted by alkylation or reductive alkylation into a corresponding alkyl compound of general formula I and/or if a compound of general formula I is obtained which contains an alkoxycarbonyl group, this may be converted by ester cleavage into a carboxylic acid, and/or if a compound of general formula I is obtained which contains an alkoxycarbonyl group, this may be converted by reaction with an amine into a carboxylic acid amide derivative, and/or if a compound of general formula I is obtained which contains a carboxy group, this may be converted by reaction with an amine into a carboxylic acid amide derivative.

In the reactions described hereinbefore any reactive groups present such as hydroxy, amino, alkylamino or imino groups may be protected during the reaction by conventional protective groups which are cleaved again after the reaction.

For example a protecting group for a hydroxy group might be the trimethylsilyl, acetyl, trityl, benzyl or tetrahydropyranyl group.

Protecting groups for an amino, alkylamino or imino group might be, for example, the formyl, acetyl, trifluoroacetyl, ethoxycarbonyl, tert.-butoxycarbonyl, benzyloxycarbonyl, benzyl, methoxybenzyl or 2,4-dimethoxybenzyl group.

Any protective group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. In the presence of iodotrimethylsilane, at temperatures between 0 and 120° C., preferably at temperatures between 10 and 100° C.

A benzyl, methoxybenzyl or benzyloxycarbonyl group, however, is cleaved by hydrogenolysis, for example, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and under a hydrogen pressure of 1 to 7 bar, but preferably from 3 to 5 bar. A 2,4-dimethoxybenzyl group, however, is preferably cleaved in trifluoroacetic acid in the presence of anisole.

A tert.-butyl or tert.-butyloxycarbonyl group is preferably cleaved by treatment with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treatment with an acid such as hydrochloric acid, optionally in the presence of a solvent such as acetic acid at temperatures between 50 and 120° C. or by treatment with sodium hydroxide solution, optionally in the presence of a solvent such as tetrahydrofuran at temperatures between 0 and 50° C.

Other suitable protective groups and possible methods of introducing and cleaving them are described for example in "Protective Groups in Organic Synthesis" by Theodora W. Greene and Peter G. M. Wuts, Wiley-VCH.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. In "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids or bases. Acids which may be used for this purpose include for example hydrochloric acid, hydrobromic acid, sulphuric acid, methanesulphonic acid, ethanesulphonic acid, benzenesulphonic acid, p-toluenesulphonic acid, phosphoric acid, fumaric acid, succinic acid, benzoic acid, salicylic acid, mandelic acid, lactic acid, malonic acid, citric acid, L-malic acid, L-tartaric acid or maleic acid. Suitable bases for this purpose include for example sodium hydroxide solution, potassium hydroxide solution, calcium hydroxide, diethanolamine or N-methyl-D-glucamine.

By the term "$C_{1-4}$-alkyl" (including where it is a component of other groups) are meant branched and unbranched alkyl groups with 1 to 4 carbon atoms. Examples include: methyl, ethyl, n-propyl, iso-propyl, n-butyl, iso-butyl, sec-butyl or tert-butyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{2-3}$-alkenyl" (including where it is a component of other groups) are meant branched and unbranched alkenyl groups with 2 to 3 carbon atoms, provided that they have at least one double bond. Examples include: ethenyl or allyl.

By the term "$C_{2-3}$-alkynyl" (including where it is a component of other groups) are meant alkynyl groups with 2 to 3 carbon atoms meant, provided that they have at least one triple bond. Examples include: ethynyl or propargyl.

By the term "$C_{3-7}$-cycloalkyl" (including where it is a component of other groups) are meant cyclic alkyl groups with 3 to 7 carbon atoms. Examples include: cyclopropyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "aryl" (including where it is a component of other groups) are meant aromatic ring systems with 6, 10 or 14 carbon atoms. Examples include: phenyl or naphthyl, the preferred aryl group being phenyl. Unless stated otherwise, the aromatic groups may be substituted by one or more groups selected from among methyl, ethyl, iso-propyl, tert-butyl, hydroxy, fluorine, chlorine, bromine and iodine.

The compounds of general formulae II to XV used as starting materials are known from the literature to some extent or may be obtained by methods known from the literature (cf. Examples I to XVIII), optionally with the additional introduction of protecting groups.

Standard processes for preparing the starting materials are described for example in "March's Advanced Organic Chemistry" by Michael B. Smith and Jerry March, Wiley-VCH or in "Science of Synthesis/Houben-Weyl" published by Thieme.

For example the compounds of general formula (IX) may be obtained as follows:

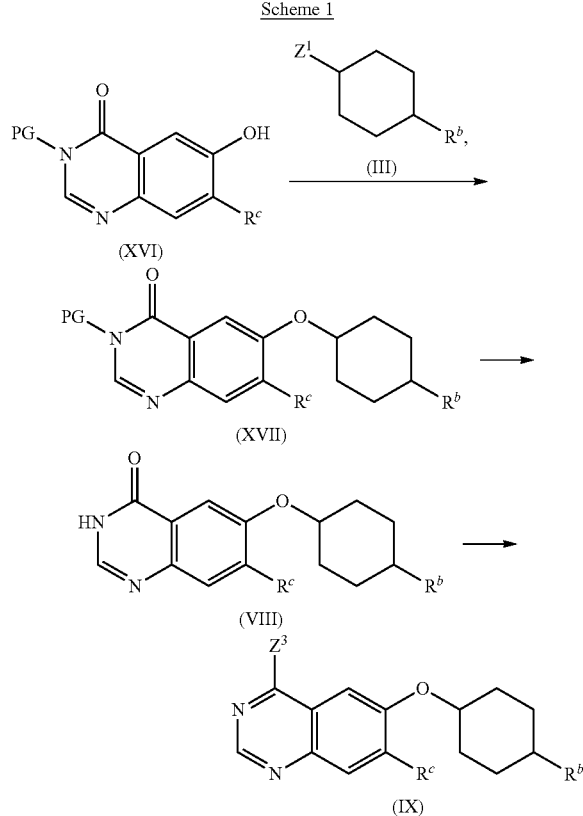

Scheme 1

Starting from a compound of general formula (XVI), wherein PG denotes a protective group such as benzyl, 4-methoxybenzyl or 2,4-dimethoxybenzyl, for example, the reaction is carried out with a compound of general formula (III) analogously to process a) described hereinbefore to obtain a compound of general formula (XVII). The compounds of general formula (XVI) are known from the literature (cf e.g. WO 2004/108664 or WO 2007/003486) or may be obtained by methods known from the literature.

The cleaving of the protective group from a compound of general formula (XVII) to obtain a compound of general formula (VIII) is carried out, if PG denotes benzyl, with hydrogen, for example, in the presence of a catalyst such as palladium/charcoal (e.g. analogously to Example IV). The cleaving of the protective group if PG denotes 4-methoxybenzyl or 2,4-dimethoxybenzyl may also be carried out oxidatively (e.g. with cerium(IV)-ammonium nitrate or with 2,3-dichloro-5,6-dicyano-1,4-benzoquinone) or with acids (e.g. with trifluoroacetic acid in the presence of anisole).

A compound of general formula (VIII) may then be converted into a compound of general formula (IX), as described in the previous process d). The meanings for $R^b$, $R^c$, $Z^1$ and $Z^3$ in the compounds of Scheme 1 are defined as mentioned hereinbefore.

As already mentioned hereinbefore, the compounds of general formula (I) according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible to block the transmission of signals to components located further downstream.

The biological properties of the new compounds were investigated as follows:

The inhibition of the EGF-R-mediated signal transmission can be demonstrated e.g. With cells which express human EGF-R and whose survival and proliferation depend on stimulation by EGF or TGF-alpha. A murine haematopoietic cell line is genetically modified so as to express functional human EGF-R. The proliferation of this cell line can therefore be stimulated by EGF.

The test is carried out as follows:

The cells are cultivated in RPMI/1640 medium. The proliferation is stimulated with 20 ng/ml of human EGF (Promega). To investigate the inhibitory activity of the compounds according to the invention these compounds are dissolved in 100% dimethylsulphoxide (DMSO) and added to the cultures in various dilutions, the maximum DMSO concentration being 1%. The cultures are incubated for 48 hours at 37° C.

In order to determine the inhibitory activity of the compounds according to the invention the relative cell number is measured in O.D. units using the Cell Titer 96™ AQueous Non-Radioactive Cell Proliferation Assay (Promega). The relative cell number is calculated as a percentage of the control and the concentration of active substance which inhibits the proliferation of the cells by 50% (IC50) is derived therefrom.

The compounds of general formula I according to the invention exhibit IC50 values of <10 micromolar, preferably <1 micromolar, for example.

The following results are obtained, for example:

| Compound (Example No.) | Inhibition of the EGFR-dependent proliferation $IC_{50}$ [nM] |
|---|---|
| 1 (trans compound) | 1 |
| 1(1) (trans compound) | 1 |
| 1(3) (trans compound) | 1 |
| 1(5) (trans compound) | 1 |
| (36) | 1 |
| (44) | 1 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis (COPD), asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating inflammatory diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers or polyps in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, the treatment of nasal polyps, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. Cis-platin, cyclophosphamide, adriamycin), hormone antagonists (e.g. tamoxifen), inhibitors of metabolic processes (e.g. 5-FU etc.), cytokines (e.g. Interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01-100 mg/kg of body weight, preferably 0.1-15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof to produce conventional galenic preparations such as plain or coated tablets, capsules, powders, suspensions, solutions, sprays or suppositories.

The Examples that follow are intended to illustrate the present invention in more detail without restricting it:

Preparation of the Starting Compounds:

EXAMPLE I

4-[(3-chloro-2-fluoro-phenyl)amino]-6-(4-oxo-cyclohexyloxy)-7-methoxy-quinazoline

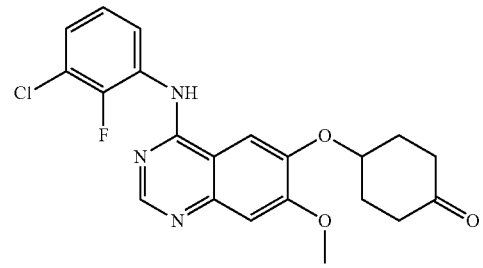

25 ml 4M sulphuric acid are added to 9.0 g 4-[(3-chloro-2-fluoro-phenyl)amino]-6-(1,4-dioxa-spiro[4.5]decan-8-yloxy)-7-methoxy-quinazoline in 110 ml of tetrahydrofuran and the mixture is stirred for 18 hours at ambient temperature. The mixture is made alkaline with 4M sodium hydroxide solution and extracted several times with ethyl acetate. The combined organic phases are dried, evaporated down and stirred with diethyl ether. The solid is suction filtered and dried.

Yield: 7.4 g (90% of theory)

Mass spectrum (ESI$^+$): m/z=416, 418 [M+H]$^+$

The following compounds are obtained analogously to Example I:

(1) 4-[(3-chloro-4-fluoro-phenyl)amino]-6-(4-oxo-cyclohexyloxy)-7-methoxy-quinazoline

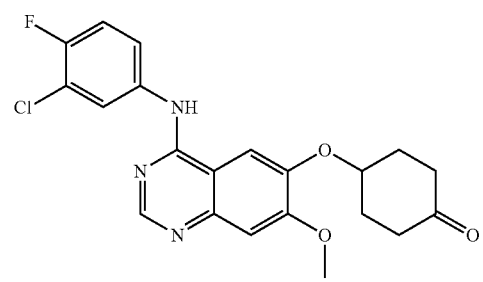

Mass spectrum (ESI$^+$): m/z=416, 418 [M+H]$^+$ (2) 3-benzyl-3,4-dihydro-4-oxo-6-(4-oxo-cyclohexyloxy)-7-methoxy-quinazoline

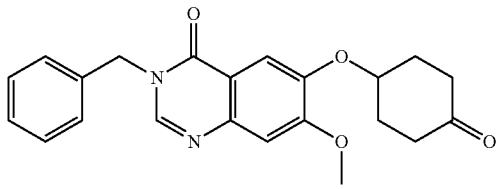

Mass spectrum (ESI⁺): m/z=379 [M+H]⁺

EXAMPLE II

4-[(3-chloro-2-fluoro-phenyl)amino]-6-(1,4-dioxaspiro[4.5]decan-8-yl-oxy)-7-methoxy-quinazoline

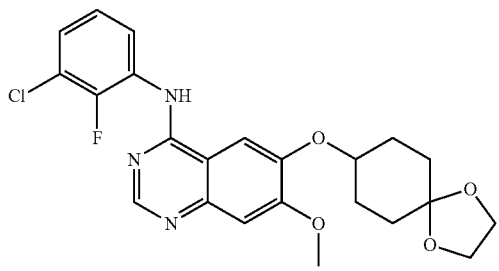

At 50° C. 12.5 g potassium carbonate and 16 g 8-methanesulphonyloxy-1,4-dioxa-spiro[4,5]decane (cf for example Journal of Medicinal Chemistry (1992), 35(12), 2243-7) are added to 18.1 g 4-[(3-chloro-2-fluoro-phenyl)amino]-6-hydroxy-7-methoxy-quinazoline (cf for example Bioorganic & Medicinal Chemistry Letters (2006), 16(18), 4908-4912) in 125 ml dimethylformamide and the mixture is stirred for 18 hours at 80° C. Another 4.7 g potassium carbonate and 4.0 g of 8-methanesulphonyloxy-1,4-dioxa-spiro[4,5]decane are added and the mixture is stirred for another 7 hours at 80° C. The reaction mixture is cooled, diluted with water and ethyl acetate and the precipitate formed is suction filtered and dried.

Yield: 12.2 g (47% of theory)
Mass spectrum (ESI⁺): m/z=460, 462 [M+H]⁺

The following is obtained analogously to Example II:

4-[(3-chloro-4-fluoro-phenyl)amino]-6-(1,4-dioxaspiro[4,5]decan-8-yl-oxy)-7-methoxy-quinazoline

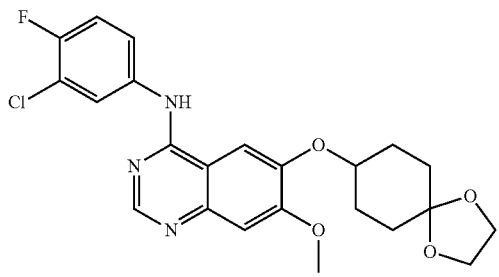

Mass spectrum (ESI⁺): m/z=460, 462 [M+H]⁺

EXAMPLE III

4-[(2-fluoro-5-methyl-phenyl)amino]-6-(4-oxo-cyclohexyloxy)-7-methoxy-quinazoline

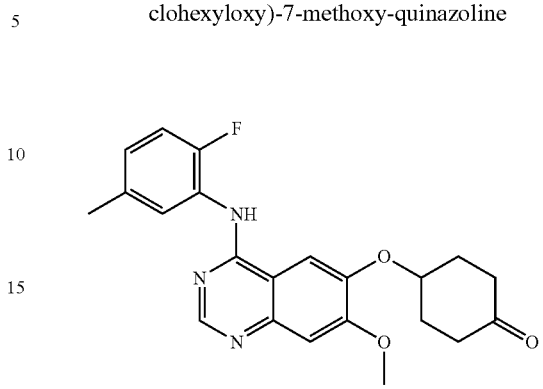

6 ml phosphorus oxychloride are added dropwise to 12.1 g 3,4-dihydro-4-oxo-6-(1,4-dioxa-spiro[4,5]decan-8-yl-oxy)-7-methoxy-quinazoline in 120 ml acetonitrile and the mixture is heated to an internal temperature of 40° C. Then 9.3 ml triethylamine are added dropwise and the reaction mixture is refluxed for 3 hours. The mixture is cooled to ambient temperature and after standing overnight half the solution of the intermediate product (4-chloro-6-(1,4-dioxa-spiro[4,5]decan-8-yl-oxy)-7-methoxy-quinazoline, see Example IX) is combined dropwise with 2.7 ml of 2-fluoro-5-methylaniline in 5 ml acetonitrile. The reaction mixture is heated to 40° C. for 3 hours, then cooled and evaporated down. The residue is mixed with water and stirred. The precipitate formed is suction filtered and divided between 1M sodium hydroxide solution and dichloromethane. The organic phase is separated off, dried, evaporated down and stirred with diisopropylether. The solid is suction filtered and dried.

Mass spectrum (ESI⁺): m/z=396 [M+H]⁺

The following compounds are obtained analogously to Example III:

(1) 4-[(2,4-difluoro-3-methyl-phenyl)amino]-6-(4-oxo-cyclohexyloxy)-7-methoxy-quinazoline

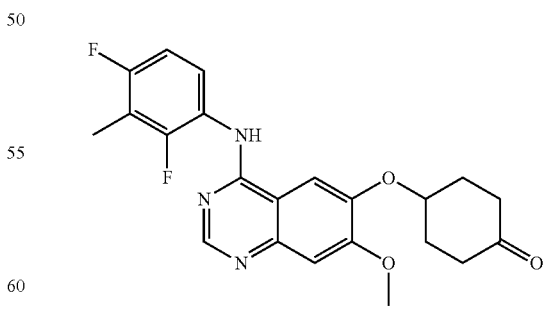

For synthesis of 2,4-difluoro-3-methyl-aniline cf for example EP 28698 In order to cleave the ketal totally the crude product is also stirred with aqueous hydrochloric acid.

Mass spectrum (ESI⁺): m/z=414 [M+H]⁺

(2) 4-[(2-fluoro-3-methyl-phenyl)amino]-6-(4-oxo-cyclohexyloxy)-7-methoxy-quinazoline

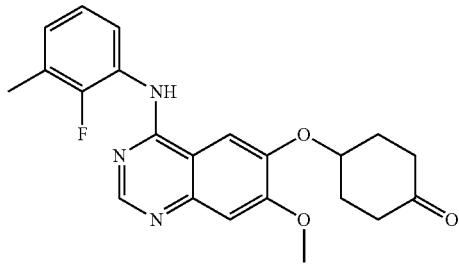

In order to cleave the ketal totally the crude product is also stirred with aqueous hydrochloric acid.

Mass spectrum (ESI⁺): m/z=396 [M+H]⁺

(3) 4-[(3-chloro-2-methyl-phenyl)amino]-6-(4-oxo-cyclohexyloxy)-7-methoxy-quinazoline

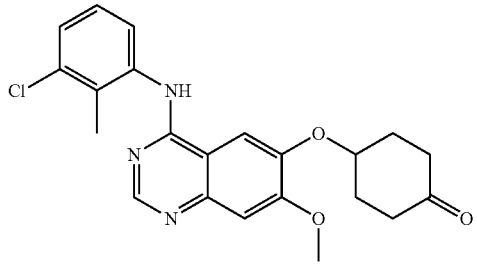

In order to cleave the ketal totally the crude product is also stirred with aqueous hydrochloric acid.

Mass spectrum (ESI⁺): m/z=412, 414 [M+H]⁺

(4) 4-[(5-chloro-2-fluoro-phenyl)amino]-6-(4-oxo-cyclohexyloxy)-7-methoxy-quinazoline

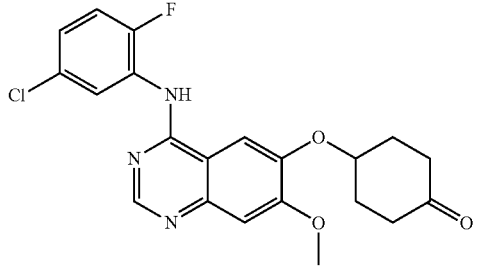

In order to cleave the ketal totally the crude product is also stirred with aqueous hydrochloric acid.

Mass spectrum (ESI⁺): m/z=416, 418 [M+H]⁺

(5) 4-[(4-fluoro-3-methyl-phenyl)amino]-6-(4-oxo-cyclohexyloxy)-7-methoxy-quinazoline

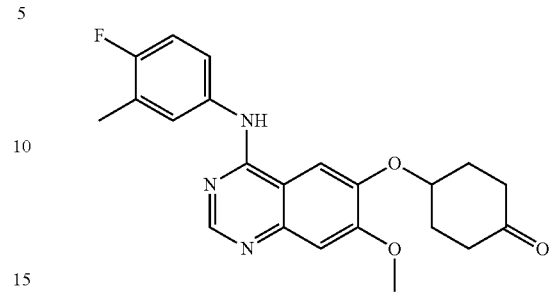

In order to cleave the ketal totally the crude product is also stirred with aqueous hydrochloric acid.

Mass spectrum (ESI⁺): m/z=396 [M+H]⁺

(6) 4-[(3-fluoro-5-methyl-phenyl)amino]-6-(4-oxo-cyclohexyloxy)-7-methoxy-quinazoline

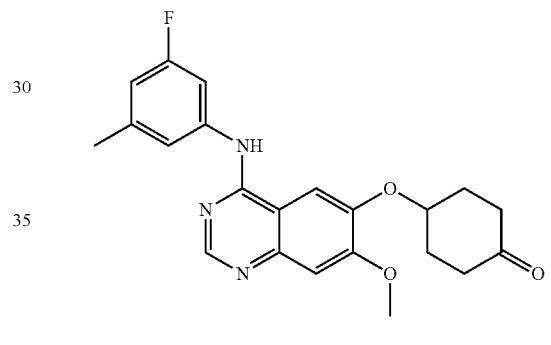

In order to cleave the ketal totally the crude product is also stirred with aqueous hydrochloric acid.

Mass spectrum (ESI⁺): m/z=396 [M+H]⁺

(7) (R)-4-[(1-phenylethyl)amino]-6-(4-oxo-cyclo-hexyloxy)-7-methoxy-quinazoline

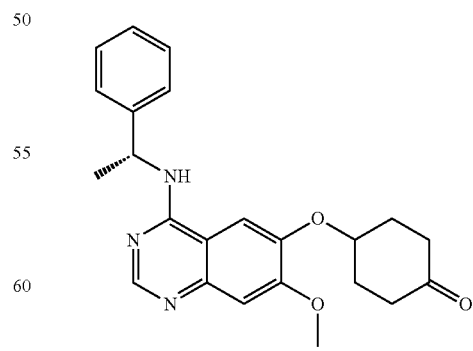

In order to cleave the ketal totally the crude product is also stirred with aqueous hydrochloric acid.

Mass spectrum (ESI⁺): m/z=392 [M+H]⁺

(8) 4-[(4-indanyl)amino]-6-(4-oxo-cyclohexyloxy)-7-methoxy-quinazoline

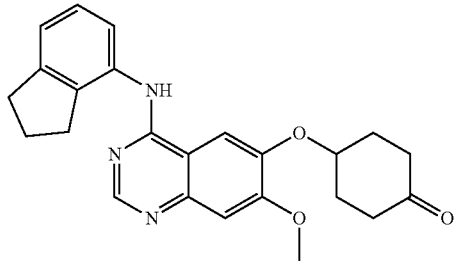

In order to cleave the ketal totally the crude product is also stirred with aqueous hydrochloric acid.
Mass spectrum (ESI⁺): m/z=404 [M+H]⁺

(9) 4-[(3-chloro-2-fluoro-phenyl)amino]-6-(4-oxo-cyclohexyloxy)-7-methoxy-quinazoline

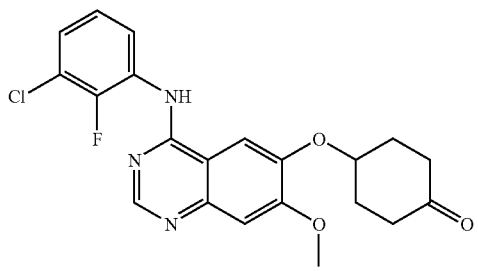

In order to cleave the ketal totally the crude product is also stirred with aqueous hydrochloric acid.
Mass spectrum (ESI⁺): m/z=416, 418 [M+H]⁺

EXAMPLE IV 3,4-dihydro-4-oxo-6-(1,4-dioxa-spiro[4,5]decan-8-yl-oxy)-7-methoxy-quinazoline

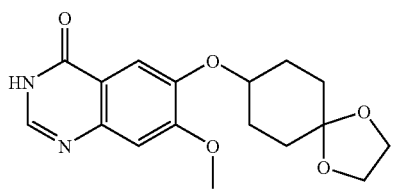

16.0 g 3-benzyl-3,4-dihydro-4-oxo-6-(1,4-dioxa-spiro[4,5]decan-8-yl-oxy)-7-methoxy-quinazoline in 150 ml glacial acetic acid are hydrogenated in the presence of 1.6 g palladium on activated charcoal (10% Pd) at 60° C. and at a hydrogen pressure of 50 psi. The catalyst is filtered off and the filtrate is evaporated down, combined with toluene and evaporated down again. The residue is mixed with water and made slightly alkaline with saturated sodium hydrogen carbonate solution. The precipitate is suction filtered and dried.
Mass spectrum (ESI⁺): m/z=333 [M+H]⁺

The following compounds may be obtained analogously to Example IV:

(1) 3,4-dihydro-4-oxo-6-[cis/trans-4-(morpholin-4-yl)-cyclohexyloxy]-7-methoxy-quinazoline

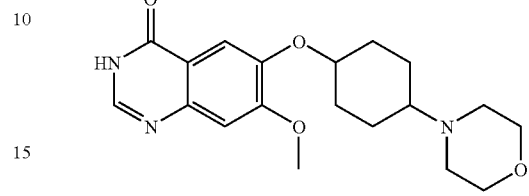

Carried Out at Ambient Temperature
Mass spectrum (ESI⁺): m/z=360 [M+H]⁺

(2) 3,4-dihydro-4-oxo-6-[trans-4-(4-methyl-3-oxo-piperazin-1-yl)-cyclohexyloxy]-7-methoxy-quinazoline

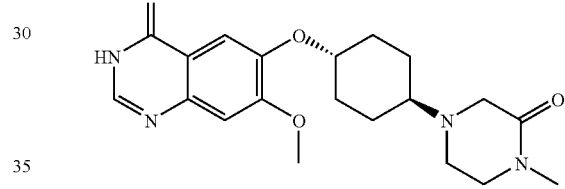

EXAMPLE V 3-benzyl-3,4-dihydro-4-oxo-6-(1,4-dioxa-spiro[4,5]decan-8-yl-oxy)-7-methoxy-quinazoline

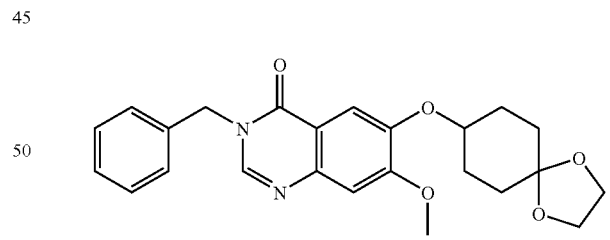

At 50° C. 16.0 g potassium carbonate and 20.0 g of 8-methanesulphonyloxy-(1,4-dioxa-spiro[4,5]decan are added to 20.0 g 3-benzyl-3,4-dihydro-4-oxo-6-hydroxy-7-methoxy-quinazoline in 150 ml N,N-dimethylformamide and the mixture is vigorously stirred for 18 hours at 80° C. To complete the reaction potassium carbonate and 8-methanesulphonyloxy-(1,4-dioxa-spiro[4,5]decane are each added three times more and in each case the mixture is stirred for several hours at 80° C. The reaction mixture is cooled and slowly combined with a total of 500 ml of water. The precipitate is suction filtered, washed with water and dried.
Mass spectrum (ESI⁺): m/z=423 [M+H]⁺

EXAMPLE VI

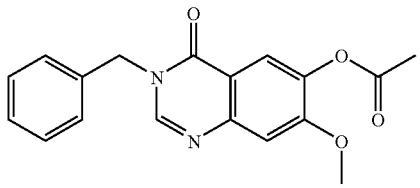

3-Benzyl-3,4-dihydro-4-oxo-6-acetyloxy-7-methoxy-quinazoline 169 g 3,4-dihydro-4-oxo-6-acetyloxy-7-methoxy-quinazoline, 118.8 ml benzyl bromide and 138.2 g potassium carbonate are heated in 1600 ml acetone for 8 hours to 35-40° C. The mixture is stirred for 15 hours at ambient temperature and then combined with 2000 ml of water. The suspension is cooled to 0° C., the precipitate is suction filtered, washed with 400 ml of water and 400 ml tert.-butylmethylether and dried at 50° C. The solid is dissolved in 4000 ml methylene chloride, filtered and evaporated down. The residue is suspended in tert.-butylmethylether, suction filtered and dried at 50° C. Yield: 203 g (86% of theory)

$R_f$ value: 0.80 (silica gel, methylene chloride/ethanol=9:1)

Mass spectrum (ESI$^+$): m/z=325 [M+H]$^+$

EXAMPLE VII

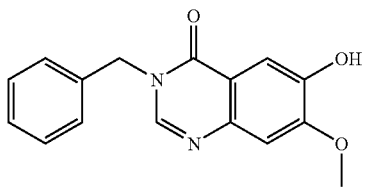

3-benzyl-3,4-dihydro-4-oxo-6-hydroxy-7-methoxy-quinazoline

Method A:

168.5 g 6-hydroxy-7-methoxy-benzo[d][1.3]oxazin-4-one are dissolved in 1200 ml of toluene and 74.7 ml benzylamine are added. The mixture is refluxed for 15 hours and then cooled to ambient temperature. The precipitate is filtered off and washed with tert.-butylmethylether.

Yield 124 g (72% of theory)

Method B:

200 g 3-benzyl-3,4-dihydro-4-oxo-6-acetyloxy-7-methoxy-quinazoline are suspended in 200 ml of water and 1000 ml of ethanol. 300 ml 10N sodium hydroxide solution are added at ambient temperature and the mixture is heated to 30° C. for 1 hour. After the addition of 172 ml acetic acid and 2000 ml of water the mixture is stirred for 20 hours at ambient temperature. The precipitate is suction filtered, washed with water and acetone and dried at 60° C.

Yield: 172.2 g (98% of theory)

$R_f$ value: 0.25 (silica gel, methylene chloride/ethanol=19:1)

Mass spectrum (ESI$^+$): m/z=283 [M+H]$^+$

EXAMPLE VIII

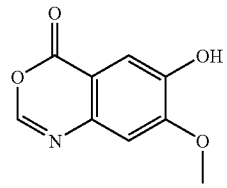

6-hydroxy-7-methoxy-benzo[d][1,3]oxazin-4-one 1 g 2-amino-5-hydroxy-4-methoxy-benzoic acid (prepared by reacting methyl 2-nitro-4,5-dimethoxy-benzoate with potassium hydroxide solution to obtain the potassium salt of 2-nitro-5-hydroxy-4-methoxy-benzoic acid and subsequent catalytic hydrogenation in the presence of palladium on activated charcoal) and 20 ml triethyl orthoformate are heated to 100° C. for 2.5 hours. After cooling to ambient temperature the precipitate is suction filtered and washed with diethyl ether.

Yield: 0.97 g (93% of theory)

$R_f$ value: 0.86 (silica gel, methylene chloride/methanol/acetic acid=90:10:1)

Mass spectrum (ESI$^+$): m/z=194 [M+H]$^+$

EXAMPLE IX 4-chloro-6-(1,4-dioxa-spiro[4,5]decan-8-yl-oxy)-7-methoxy-quinazoline

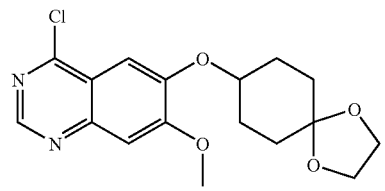

6 ml phosphorus oxychloride are added dropwise to 12.1 g 3,4-dihydro-4-oxo-6-(1,4-dioxa-spiro[4,5]decan-8-yl-oxy)-7-methoxy-quinazoline in 120 ml acetonitrile and the mixture is heated to an internal temperature of 40° C. Then 9.3 ml triethylamine are added dropwise and the reaction mixture is refluxed for 3 hours. The mixture is cooled to ambient temperature and left to stand overnight. The solution of the product is reacted further without any purification (see Example III).

The following compounds may be obtained analogously to Example IV:

(1) 4-chloro-6-[cis/trans-4-(morpholin-4-yl)-cyclohexyloxy]-7-methoxy-quinazoline

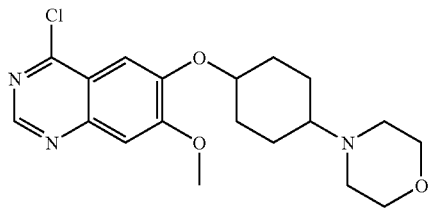

(2) 4-chloro-6-[trans-4-(4-methyl-3-oxo-piperazin-1-yl)-cyclohexyloxy]-7-methoxy-quinazoline

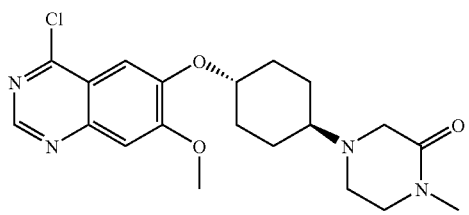

EXAMPLE X (cis)-1-methanesulphonyloxy-4-(4-methyl-3-oxo-piperazin-1-yl)-cyclohexane

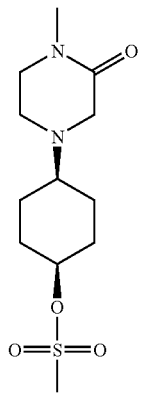

0.24 ml methanesulphonic acid chloride are added dropwise at 0° C. to 500 mg (cis)-1-hydroxy-4-(4-methyl-3-oxo-piperazin-1-yl)-cyclohexane and 0.52 ml N,N-isopropyl-ethylamine in 10 ml dichloromethane and stirred for 1.5 hours at ambient temperature. The product is purified by column chromatography.

Mass spectrum (ESI$^+$): m/z=291 [M+H]$^+$

EXAMPLE XI (cis)-1-hydroxy-4-(4-methyl-3-oxo-piperazin-1-yl)-cyclohexane

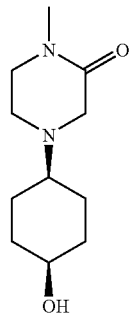

17 ml of a 1M L-Selctride solution (in tetrahydrofuran) are added dropwise at −78° C. to 3.3 g 4-(4-methyl-3-oxo-piperazin-1-yl)-cyclohexan-1-one in 100 ml abs. tetrahydrofuran. After 5.5 hours 20 ml of methanol are added and the solution is evaporated down. The residue is purified by column chromatography. The mixture of cis- and trans-compound is separated by preparative HPLC.

Mass spectrum (ESI$^+$): m/z=213 [M+H]$^+$

EXAMPLE XII 4-(4-methyl-3-oxo-piperazin-1-yl)-cyclohexan-1-one

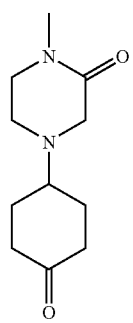

0.55 ml dimethylsulphoxide in 2 ml dichloromethane are added dropwise to 0.46 ml oxalyl chloride in 10 ml dichloromethane within two minutes at −60° C. After 5 minutes 1.0 g (trans)-1-hydroxy-4-(4-methyl-3-oxo-piperazin-1-yl)-cyclohexane in 8 ml dichloromethane are added within 5 min. After 20 minutes 3.3 ml triethylamine are added and the mixture is stirred for 70 minutes at ambient temperature. 15 ml of water are added and the mixture is extracted with dichloromethane. After evaporation of the solvent the residue contains the product.

Mass spectrum (ESI$^+$): m/z=211 [M+H]$^+$

EXAMPLE XIII 4-(4-methyl-3-oxo-piperazin-1-yl)-cyclohexan-1-one

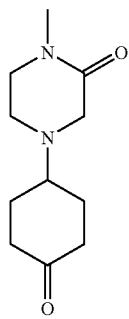

2.3 g 8-(4-methyl-3-oxo-piperazin-1-yl)-1,4-dioxa-spiro[4,5]decane are stirred in 20 ml of 4M HCl for 48 hours at ambient temperature, for 7 hours at 50° C. and for two hours at 70° C. The mixture is made alkaline with 4M sodium hydroxide solution and extracted five times with 40 ml dichloromethane. The organic phase is evaporated down and the product is purified by column chromatography.

Mass spectrum (ESI$^+$): m/z=211 [M+H]$^+$

EXAMPLE XIV (trans)-1-hydroxy-4-(4-methyl-3-oxo-piperazin-1-yl)-cyclohexane

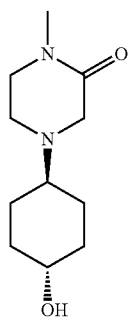

10.0 g (trans)-1-hydroxy-4-{[N-(2,2-dimethoxy-ethyl)-N-methyl-amino]-carbonylmethylamino}-cyclohexane are hydrogenated in a solution of 60 ml of water, 140 ml of methanol and 10.5 g methanesulphonic acid with 3.25 g platinum on charcoal (5% Pt) for 24 hours at 50° C. The solution is made alkaline with 50% sodium hydroxide solution and evaporated down. The residue is extracted with dichloromethane. The organic phase is dried on magnesium sulphate and evaporated down.

Mass spectrum (ESI$^+$): m/z=213 [M+H]$^+$

The following may be obtained analogously to Example XIV:

(cis)-1-hydroxy-4-(4-methyl-3-oxo-piperazin-1-yl)-cyclohexane

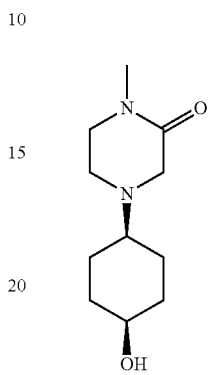

EXAMPLE XV (trans)-1-hydroxy-4-{[N-(2,2-dimethoxy-ethyl)-N-methyl-amino]-carbonylmethylamino}-cyclohexane

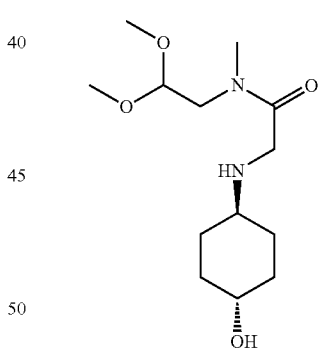

15.0 g 2-chloro-N-(2,2-dimethoxy-ethyl)-N-methyl-acetamide in 80 ml acetonitrile are added dropwise within one hour to a suspension of 10.6 g (trans)-4-aminocyclohexanol, 16.25 g sodium carbonate and 0.64 g potassium iodide in 220 ml acetonitrile which has been warmed to 85° C. The mixture is stirred for one hour at 85° C. and for 16.5 hours at ambient temperature. It is filtered off and the filtrate is evaporated down. The residue is purified by chromatography and then recrystallised from methyl-tert-butylether and cyclohexane.

Mass spectrum (ESI$^+$): m/z=275 [M+H]$^+$

The following may be obtained analogously to Example XV:

(cis)-1-hydroxy-4-{[N-(2,2-dimethoxy-ethyl)-N-methyl-amino]-carbonylmethylamino}-cyclohexane

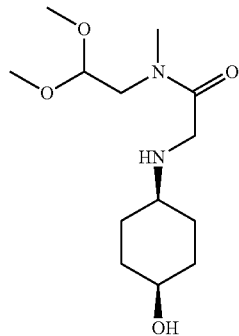

EXAMPLE XVI 8-(4-methyl-3-oxo-piperazin-1-yl)-1,4-dioxa-spiro[4,5]decane

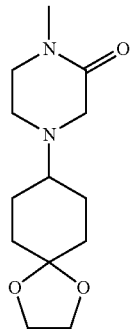

26.18 g Sodium triacetoxyborohydride are added at 5° C. to a solution of 10.0 g 4-methyl-3-oxo-piperazine, 13.51 g 1,4-dioxa-spiro[4,5]decan-8-one, 5.65 ml acetic acid and 200 ml dichloromethane. After 23 hours stirring at ambient temperature 100 ml dichloromethane and 100 ml 4N sodium hydroxide solution are added. The phases are separated and the organic phase is evaporated down. The residue is purified by chromatography.
Mass spectrum (ESI$^+$): m/z=255 [M+H]$^+$

EXAMPLE XVII 3-benzyl-3,4-dihydro-4-oxo-6-[trans-4-(4-methyl-3-oxo-piperazin-1-yl)-cyclohexyloxy]-7-methoxy-quinazoline

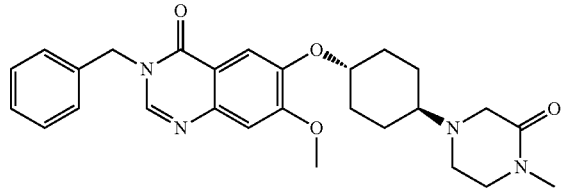

650 mg (cis)-1-methanesulphonyloxy-4-(4-methyl-3-oxo-piperazin-1-yl)-cyclohexane in 3 ml N-methyl-2-pyrrolidinone are added dropwise at 120° C. over two hours to 632 mg 3-benzyl-3,4-dihydro-4-oxo-6-hydroxy-7-methoxy-quinazoline and 1.09 g caesium carbonate in 4 ml N-methyl-2-pyrrolidinone. The product is isolated by preparative HPLC.
Mass spectrum (ESI$^+$): m/z=477 [M+H]$^+$

EXAMPLE XVIII 3-benzyl-3,4-dihydro-4-oxo-6-[cis/trans-4-(4-morpholin-4-yl)-cyclohexyloxy]-7-methoxy-quinazoline

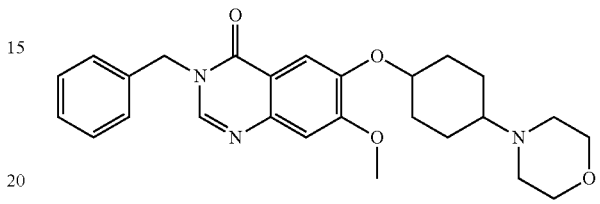

Prepared by reacting 3-benzyl-3,4-dihydro-4-oxo-6-(4-oxo-cyclohexyloxy)-7-methoxy-quinazoline with morpholine analogously to Example 1.
Mass spectrum (ESI$^+$): m/z=450 [M+H]$^+$
Preparation of the End Compounds:

EXAMPLE 1

4-[(3-chloro-2-fluoro-phenyl)amino]-6-[cis-4-(morpholin-4-yl)-cyclohexyloxy]-7-methoxy-quinazoline and 4-[(3-chloro-2-fluoro-phenyl)amino]-6-[trans-4-(morpholin-4-yl)-cyclohexyloxy]-7-methoxy-quinazoline

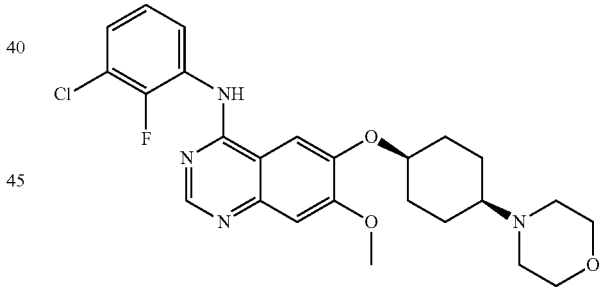

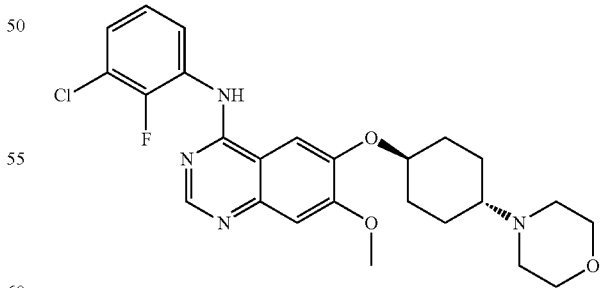

175 µl morpholine, 600 mg sodium-triacetoxyborohydride and 115 µl glacial acetic acid are added to 800 mg of 4-[(3-chloro-2-fluoro-phenyl)amino]-6-(4-oxo-cyclohexyloxy)-7-methoxy-quinazoline in 25 ml 1,2-dichloroethane and the mixture is stirred for 18 hours at ambient temperature under an argon atmosphere. Some more sodium-triacetoxyborohydride is added and stirring is continued for a further 3 hours. The reaction mixture is combined with 1M sodium hydroxide solution and briefly stirred, then extracted several times with dichloromethane. The combined organic phases are dried on magnesium sulphate and evaporated down. Purification through a silica gel column with dichloromethane/methanol (99:1 to 80:20) yields the two title compounds as a mixture. The cis/trans mixture is separated by preparative HPLC (xBridge™ C18 of Messrs. Waters; acetonitrile, water, aqueous ammonia). The isomers are attributed by 1H-NMR spectroscopy.

4-[(3-chloro-2-fluoro-phenyl)amino]-6-[cis-4-(morpholin-4-yl)-cyclohexyloxy]-7-methoxy-quinazoline Yield: 250 mg (25% of theory)

Mass spectrum (ESI$^+$): m/z=487, 489 [M+H]$^+$

4-[(3-chloro-2-fluoro-phenyl)amino]-6-[trans-4-(morpholin-4-yl)-cyclohexyloxy]-7-methoxy-quinazoline Yield: 320 mg (33% of theory)

Mass spectrum (ESI$^+$): m/z=487, 489 [M+H]$^+$

The following compounds are obtained analogously to Example 1:

(1) 4-[(3-chloro-2-fluoro-phenyl)amino]-6-[(R)-cis-4-(3-hydroxy-pyrrolidin-1-yl)-cyclohexyloxy]-7-methoxy-quinazoline and 4-[(3-chloro-2-fluoro-phenyl)amino]-6-[(R)-trans-4-(3-hydroxy-pyrrolidin-1-yl)-cyclohexyloxy]-7-methoxy-quinazoline

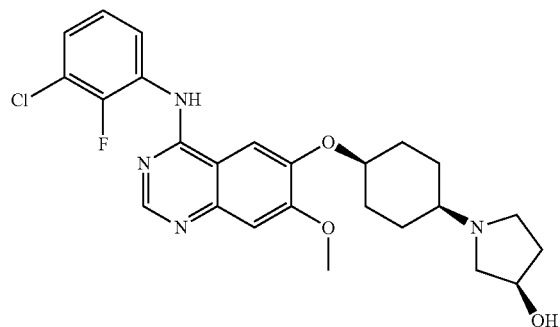

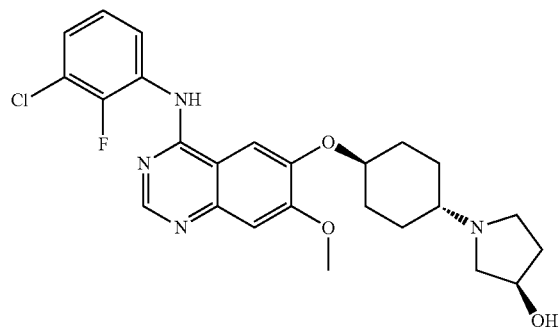

The reaction is carried out in tetrahydrofuran.

4-[(3-chloro-2-fluoro-phenyl)amino]-6-[(R)-cis-4-(3-hydroxy-pyrrolidin-1-yl)-cyclohexyloxy]-7-methoxy-quinazoline Mass spectrum (ESI$^+$): m/z=487, 489 [M+H]$^+$ 4-[(3-chloro-2-fluoro-phenyl)amino]-6-[(R)-trans-4-(3-hydroxy-pyrrolidin-1-yl)-cyclohexyloxy]-7-methoxy-quinazoline Mass spectrum (ESI$^+$): m/z=487, 489 [M+H]$^+$ (2) 4-[(3-chloro-2-fluoro-phenyl)amino]-6-[(S)-cis-4-(3-hydroxy-pyrrolidin-1-yl)-cyclohexyloxy]-7-methoxy-quinazoline and 4-[(3-chloro-2-fluoro-phenyl)amino]-6-[(S)-trans-4-(3-hydroxy-pyrrolidin-1-yl)-cyclohexyloxy]-7-methoxy-quinazoline

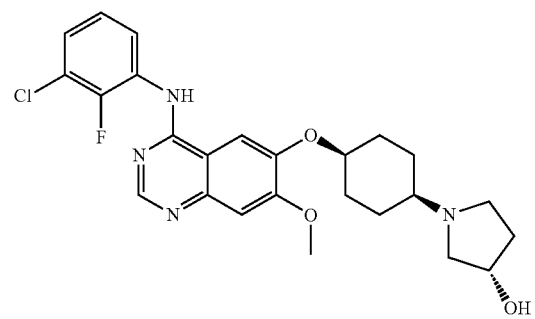

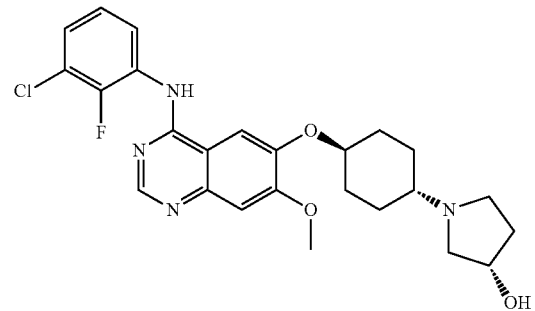

The reaction is carried out in tetrahydrofuran.

4-[(3-chloro-2-fluoro-phenyl)amino]-6-[(S)-cis-4-(3-hydroxy-pyrrolidin-1-yl)-cyclohexyloxy]-7-methoxy-quinazoline Mass spectrum (ESI$^+$): m/z=487, 489 [M+H]$^+$ 4-[(3-chloro-2-fluoro-phenyl)amino]-6-[(S)-trans-4-(3-hydroxy-pyrrolidin-1-yl)-cyclohexyloxy]-7-methoxy-quinazoline Mass spectrum (ESI$^+$): m/z=487, 489 [M+H]$^+$ (3) 4-[(3-chloro-2-fluoro-phenyl)amino]-6-[cis-4-(3-oxo-piperazin-1-yl)-cyclohexyloxy]-7-methoxy-quinazoline and 4-[(3-chloro-2-fluoro-phenyl)amino]-6-[trans-4-(3-oxo-piperazin-1-yl)-cyclohexyloxy]-7-methoxy-quinazoline

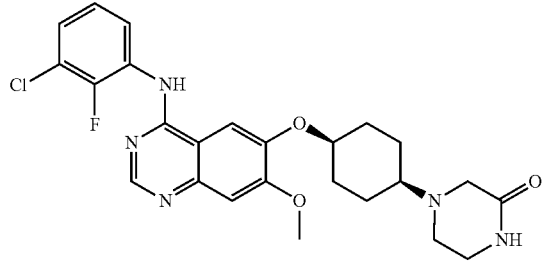

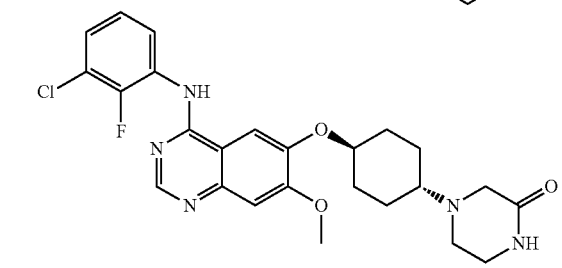

The reaction is carried out in 1,2-dichloroethane.

4-[(3-chloro-2-fluoro-phenyl)amino]-6-[cis-4-(3-oxo-piperazin-1-yl)-cyclohexyloxy]-7-methoxy-quinazoline Mass spectrum (ESI⁺): m/z=500, 502 [M+H]⁺

4-[(3-chloro-2-fluoro-phenyl)amino]-6-[trans-4-(3-oxo-piperazin-1-yl)-cyclohexyloxy]-7-methoxy-quinazoline Mass spectrum (ESI⁺): m/z=500, 502 [M+H]⁺

(4) 4-[(3-chloro-2-fluoro-phenyl)amino]-6-{(S)-cis-4-[2-(N,N-dimethylaminocarbonyl)-pyrrolidin-1-yl]-cyclohexyloxy]-7-methoxy-quinazoline and 4-[(3-chloro-2-fluoro-phenyl)amino]-6-{(S)-trans-4-[2-(N,N-dimethylaminocarbonyl)-pyrrolidin-1-yl]-cyclohexyloxy]-7-methoxy-quinazoline

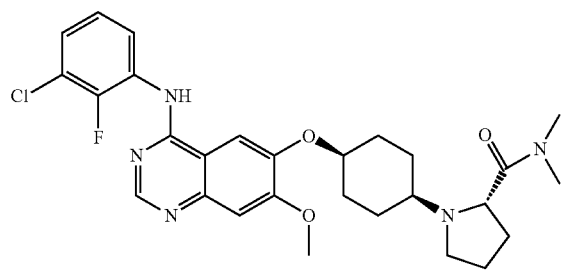

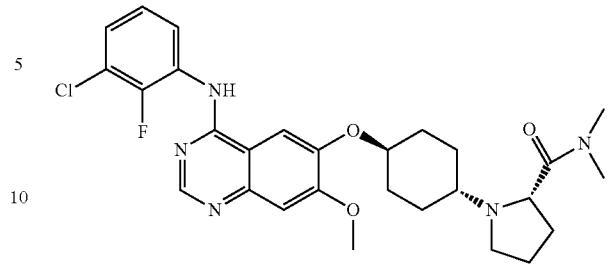

The reaction is carried out in tetrahydrofuran.

4-[(3-chloro-2-fluoro-phenyl)amino]-6-{(S)-cis-4-[2-(N,N-dimethylaminocarbonyl)-pyrrolidin-1-yl]-cyclohexyloxy]-7-methoxy-quinazoline Mass spectrum (ESI⁺): m/z=542, 544 [M+H]⁺

4-[(3-chloro-2-fluoro-phenyl)amino]-6-{(S)-trans-4-[2-(N,N-dimethylaminocarbonyl)-pyrrolidin-1-yl]-cyclohexyloxy]-7-methoxy-quinazoline Mass spectrum (ESI⁺): m/z=542, 544 [M+H]⁺

(5) 4-[(3-chloro-2-fluoro-phenyl)amino]-6-{(S)-cis-4-[2-(aminocarbonyl)-pyrrolidin-1-yl]-cyclohexyloxy]-7-methoxy-quinazoline and 4-[(3-chloro-2-fluoro-phenyl)amino]-6-{(S)-trans-4-[2-(aminocarbonyl)-pyrrolidin-1-yl]-cyclohexyloxy]-7-methoxy-quinazoline

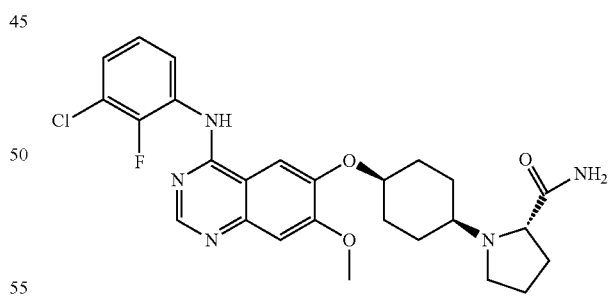

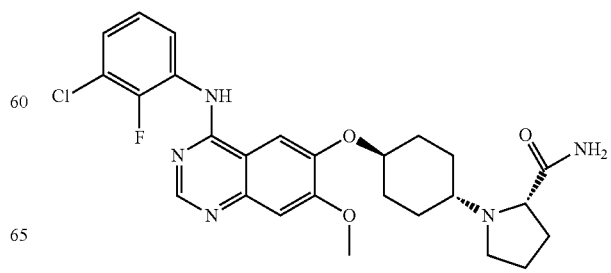

The reaction is carried out in tetrahydrofuran.

4-[(3-chloro-2-fluoro-phenyl)amino]-6-{(S)-cis-4-[2-(aminocarbonyl)-pyrrolidin-1-yl]-cyclohexyloxy]-7-methoxy-quinazoline Mass spectrum (ESI$^+$): m/z=514, 516 [M+H]$^+$ 4-[(3-chloro-2-fluoro-phenyl)amino]-6-{(S)-trans-4-[2-(aminocarbonyl)-pyrrolidin-1-yl]-cyclohexyloxy]-7-methoxy-quinazoline Mass spectrum (ESI$^+$): m/z=514, 516 [M+H]$^+$ (6) 4-[(2-fluoro-5-methyl-phenyl)amino]-6-[cis-4-(3-oxo-piperazin-1-yl)-cyclohexyloxy]-7-methoxy-quinazoline and 4-[(2-fluoro-5-methyl-phenyl)amino]-6-[trans-4-(3-oxo-piperazin-1-yl)-cyclohexyloxy]-7-methoxy-quinazoline

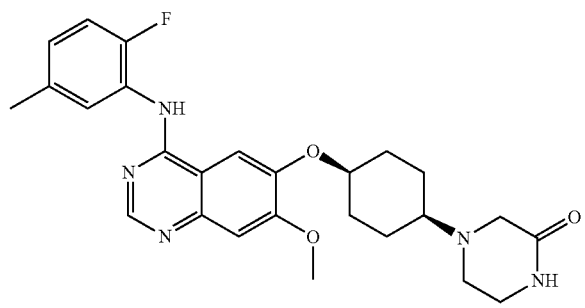

The reaction is carried out in tetrahydrofuran.

4-[(2-fluoro-5-methyl-phenyl)amino]-6-[cis-4-(3-oxo-piperazin-1-yl)-cyclohexyloxy]-7-methoxy-quinazoline Mass spectrum (ESI$^+$): m/z=480 [M+H]$^+$ 4-[(2-fluoro-5-methyl-phenyl)amino]-6-[trans-4-(3-oxo-piperazin-1-yl)-cyclohexyloxy]-7-methoxy-quinazoline Mass spectrum (ESI$^+$): m/z=480 [M+H]$^+$ (7) 4-[(2,4-difluoro-3-methyl-phenyl)amino]-6-[cis-4-(3-oxo-piperazin-1-yl)-cyclohexyloxy]-7-methoxy-quinazoline and 4-[(2,4-difluoro-3-methyl-phenyl)amino]-6-[trans-4-(3-oxo-piperazin-1-yl)-cyclohexyloxy]-7-methoxy-quinazoline

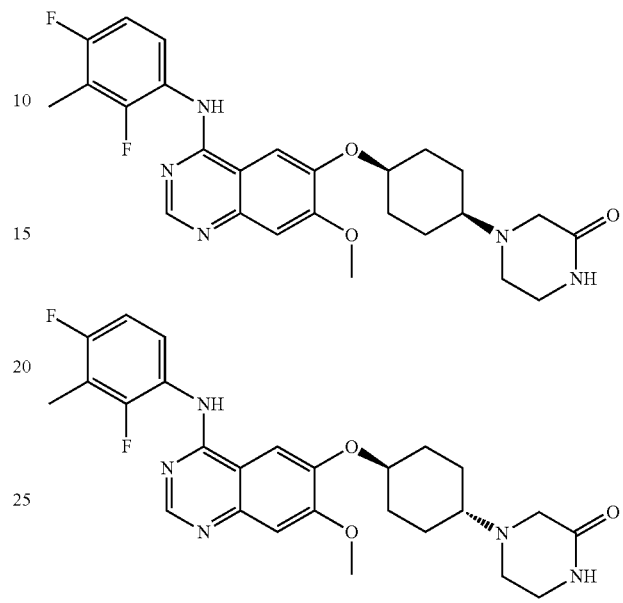

The reaction is carried out in tetrahydrofuran.

4-[(2,4-difluoro-3-methyl-phenyl)amino]-6-[cis-4-(3-oxo-piperazin-1-yl)-cyclohexyloxy]-7-methoxy-quinazoline Mass spectrum (ESI$^+$): m/z=498 [M+H]$^+$ 4-[(2,4-difluoro-3-methyl-phenyl)amino]-6-[trans-4-(3-oxo-piperazin-1-yl)-cyclohexyloxy]-7-methoxy-quinazoline Mass spectrum (ESI$^+$): m/z=498 [M+H]$^+$ (8) 4-[(2-fluoro-3-methyl-phenyl)amino]-6-[cis-4-(3-oxo-piperazin-1-yl)-cyclohexyloxy]-7-methoxy-quinazoline and 4-[(2-fluoro-3-methyl-phenyl)amino]-6-[trans-4-(3-oxo-piperazin-1-yl)-cyclohexyloxy]-7-methoxy-quinazoline

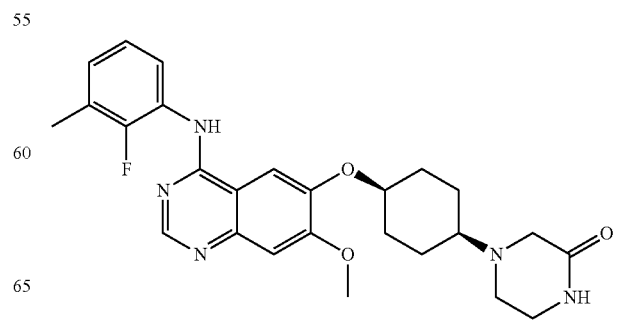

-continued

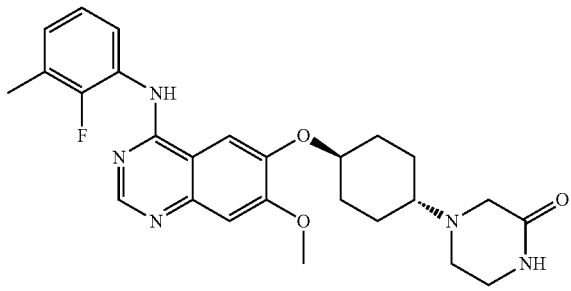

The reaction is carried out in tetrahydrofuran.

4-[(2-fluoro-3-methyl-phenyl)amino]-6-[cis-4-(3-oxo-piperazin-1-yl)-cyclohexyloxy]-7-methoxy-quinazoline Mass spectrum (ESI⁺): m/z=480 [M+H]⁺

4-[(2-fluoro-3-methyl-phenyl)amino]-6-[trans-4-(3-oxo-piperazin-1-yl)-cyclohexyloxy]-7-methoxy-quinazoline Mass spectrum (ESI⁺): m/z=480 [M+H]⁺

(9) 4-[(3-chloro-2-methyl-phenyl)amino]-6-[cis-4-(3-oxo-piperazin-1-yl)-cyclohexyloxy]-7-methoxy-quinazoline and 4-[(3-chloro-2-methyl-phenyl)amino]-6-[trans-4-(3-oxo-piperazin-1-yl)-cyclohexyloxy]-7-methoxy-quinazoline

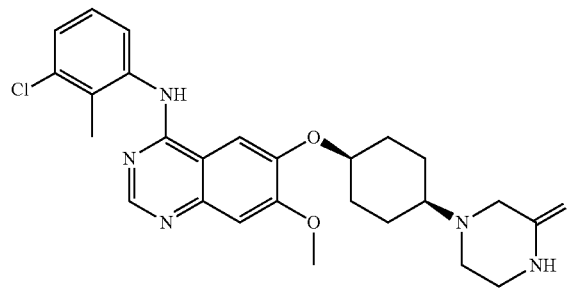

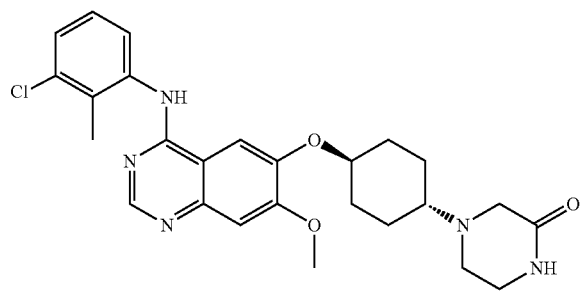

The reaction is carried out in tetrahydrofuran.

4-[(3-chloro-2-methyl-phenyl)amino]-6-[cis-4-(3-oxo-piperazin-1-yl)-cyclohexyloxy]-7-methoxy-quinazoline Mass spectrum (ESI⁺): m/z=496, 498 [M+H]⁺

4-[(3-chloro-2-methyl-phenyl)amino]-6-[trans-4-(3-oxo-piperazin-1-yl)-cyclohexyloxy]-7-methoxy-quinazoline Mass spectrum (ESI⁺): m/z=496, 498 [M+H]⁺

(10) 4-[(3-chloro-4-fluoro-phenyl)amino]-6-[cis-4-(3-oxo-piperazin-1-yl)-cyclohexyloxy]-7-methoxy-quinazoline and 4-[(3-chloro-4-fluoro-phenyl)amino]-6-[trans-4-(3-oxo-piperazin-1-yl)-cyclohexyloxy]-7-methoxy-quinazoline

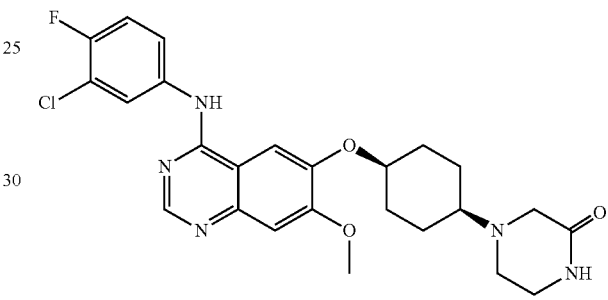

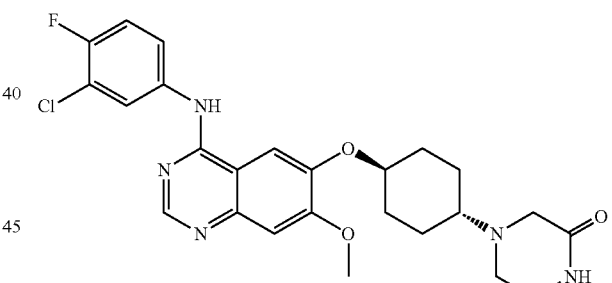

The reaction is carried out in tetrahydrofuran.

4-[(3-chloro-4-fluoro-phenyl)amino]-6-[cis-4-(3-oxo-piperazin-1-yl)-cyclohexyloxy]-7-methoxy-quinazoline Mass spectrum (ESI⁺): m/z=500, 502 [M+H]⁺

4-[(3-chloro-4-fluoro-phenyl)amino]-6-[trans-4-(3-oxo-piperazin-1-yl)-cyclohexyloxy]-7-methoxy-quinazoline Mass spectrum (ESI⁺): m/z=500, 502 [M+H]⁺

(11) 4-[(5-chloro-2-fluoro-phenyl)amino]-6-[cis-4-(3-oxo-piperazin-1-yl)-cyclohexyloxy]-7-methoxy-quinazoline and 4-[(5-chloro-2-fluoro-phenyl)amino]-6-[trans-4-(3-oxo-piperazin-1-yl)-cyclohexyloxy]-7-methoxy-quinazoline

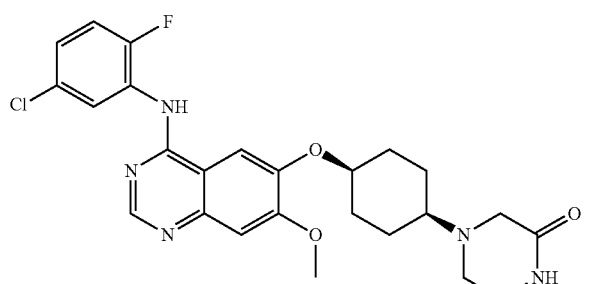

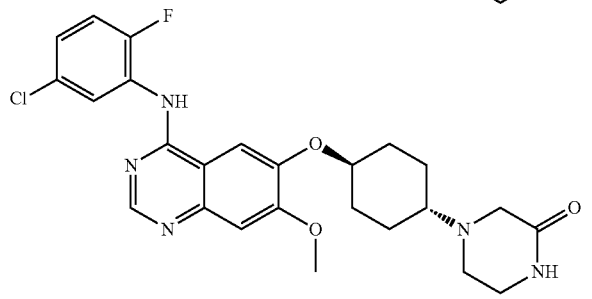

The reaction is carried out in tetrahydrofuran.

4-[(5-chloro-2-fluoro-phenyl)amino]-6-[cis-4-(3-oxo-piperazin-1-yl)-cyclohexyloxy]-7-methoxy-quinazoline Mass spectrum (ESI$^+$): m/z=500, 502 [M+H]$^+$ 4-[(5-chloro-2-fluoro-phenyl)amino]-6-[trans-4-(3-oxo-piperazin-1-yl)-cyclohexyloxy]-7-methoxy-quinazoline Mass spectrum (ESI$^+$): m/z=500, 502 [M+H]$^+$

(12) 4-[(4-fluoro-3-methyl-phenyl)amino]-6-[cis-4-(3-oxo-piperazin-1-yl)-cyclohexyloxy]-7-methoxy-quinazoline and 4-[(4-fluoro-3-methyl-phenyl)amino]-6-[trans-4-(3-oxo-piperazin-1-yl)-cyclohexyloxy]-7-methoxy-quinazoline

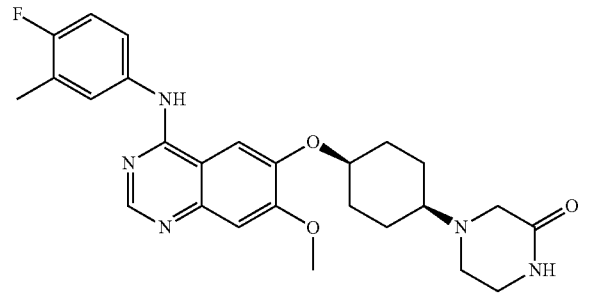

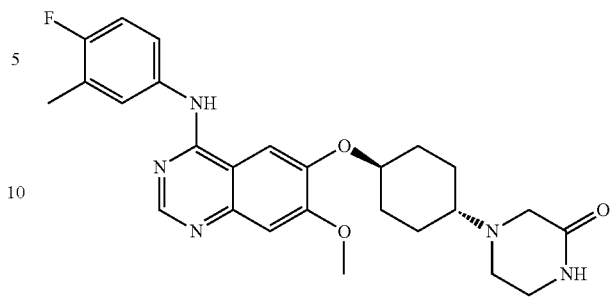

The reaction is carried out in tetrahydrofuran.

4-[(4-fluoro-3-methyl-phenyl)amino]-6-[cis-4-(3-oxo-piperazin-1-yl)-cyclohexyloxy]-7-methoxy-quinazoline Mass spectrum (ESI$^+$): m/z=480 [M+H]$^+$ 4-[(4-fluoro-3-methyl-phenyl)amino]-6-[trans-4-(3-oxo-piperazin-1-yl)-cyclohexyloxy]-7-methoxy-quinazoline Mass spectrum (ESI$^+$): m/z=480 [M+H]$^+$

(13) 4-[(3-fluoro-5-methyl-phenyl)amino]-6-[cis-4-(3-oxo-piperazin-1-yl)-cyclohexyloxy]-7-methoxy-quinazoline and 4-[(3-fluoro-5-methyl-phenyl)amino]-6-[trans-4-(3-oxo-piperazin-1-yl)-cyclohexyloxy]-7-methoxy-quinazoline

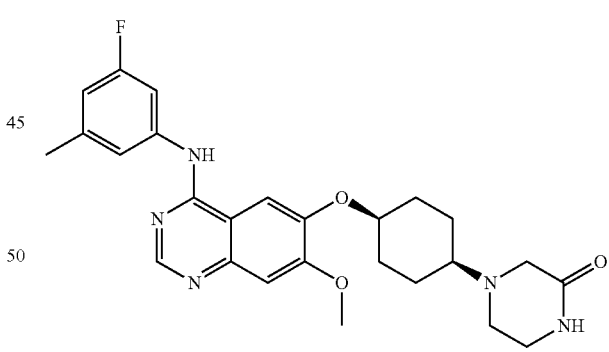

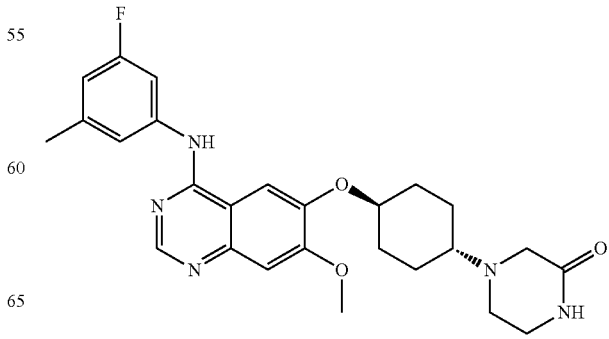

The reaction is carried out in tetrahydrofuran.

4-[(3-fluoro-5-methyl-phenyl)amino]-6-[cis-4-(3-oxo-piperazin-1-yl)-cyclohexyloxy]-7-methoxy-quinazoline Mass spectrum (ESI⁺): m/z=480 [M+H]⁺

4-[(3-fluoro-5-methyl-phenyl)amino]-6-[trans-4-(3-oxo-piperazin-1-yl)-cyclohexyloxy]-7-methoxy-quinazoline

(14) (R)-4-[(1-phenylethyl)amino]-6-[cis-4-(3-oxo-piperazin-1-yl)-cyclohexyloxy]-7-methoxy-quinazoline and (R)-4-[(1-phenylethyl)amino]-6-[trans-4-(3-oxo-piperazin-1-yl)-cyclohexyloxy]-7-methoxy-quinazoline

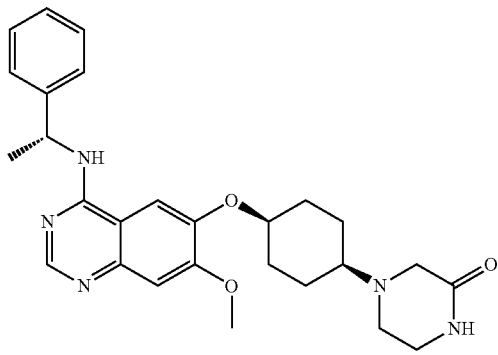

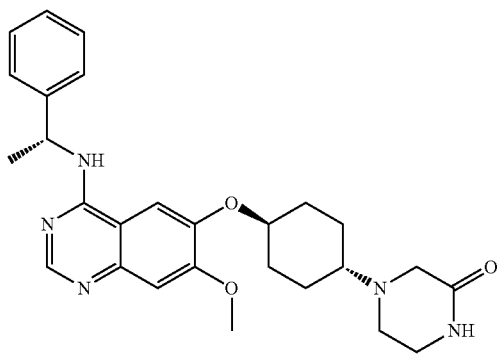

The reaction is carried out in tetrahydrofuran.

(R)-4-[(1-phenylethyl)amino]-6-[cis-4-(3-oxo-piperazin-1-yl)-cyclohexyloxy]-7-methoxy-quinazoline Mass spectrum (ESI⁺): m/z=476 [M+H]⁺

(R)-4-[(1-phenylethyl)amino]-6-[trans-4-(3-oxo-piperazin-1-yl)-cyclohexyloxy]-7-methoxy-quinazoline Mass spectrum (ESI⁺): m/z=476 [M+H]⁺

EXAMPLE 2

4-[(3-Chloro-2-fluoro-phenyl)amino]-6-[trans-4-(4-methyl-3-oxo-piperazin-1-yl)-cyclohexyloxy]-7-methoxy-quinazoline

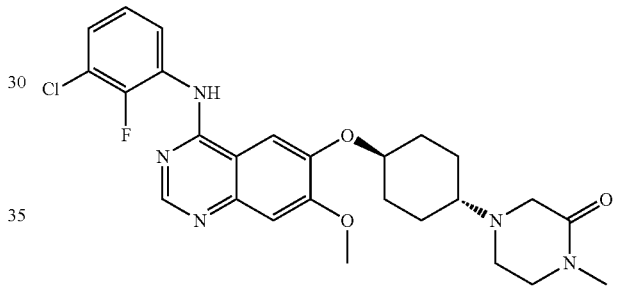

Prepared by reacting 4-[(3-chloro-2-fluoro-phenyl)amino]-6-hydroxy-7-methoxy-quinazoline with (cis)-1-methanesulphonyloxy-4-(4-methyl-3-oxo-piperazin-1-yl)-cyclohexane in N-methyl-2-pyrrolidinone at 125° C. in the presence of potassium carbonate.

The following compounds may also be prepared analogously to the Examples described above and other methods known from the literature:

| Example No. | Structure |
|---|---|
| (1) | ![structure] |

| Example No. | Structure |
|---|---|
| (2) | 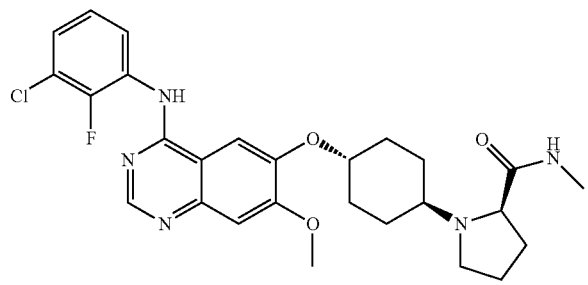 |
| (3) | 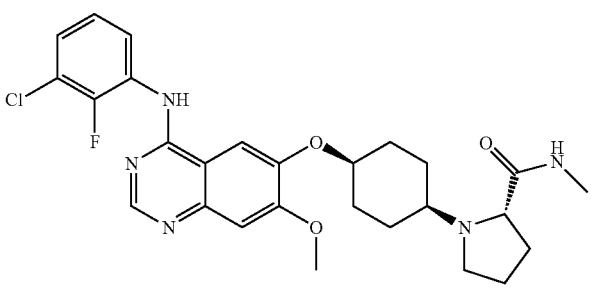
Carried out according to Example 1 in tetrahydrofuran
Mass spectrum (ESI$^+$): m/z = 528, 530 [M + H]$^+$ |
| (4) | 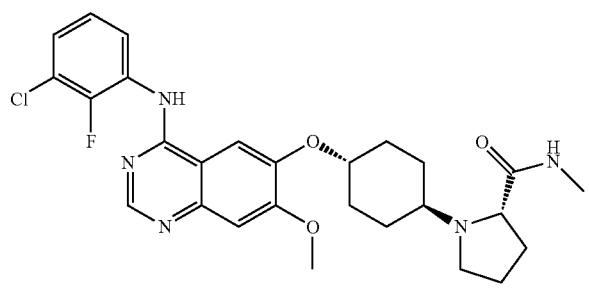
Carried out according to Example 1 in tetrahydrofuran
Mass spectrum (ESI$^+$): m/z = 528, 530 [M + H]$^+$ |
| (5) | 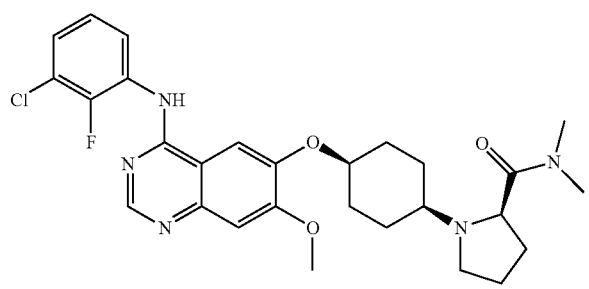 |

| Example No. | Structure |
|---|---|
| (6) | 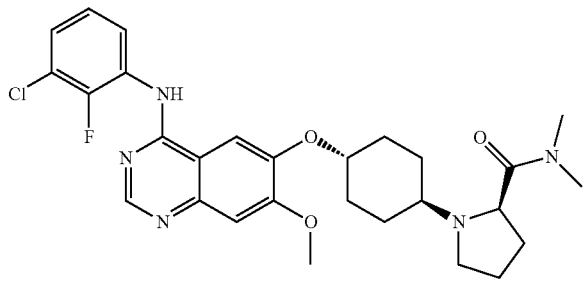 |
| (7) | 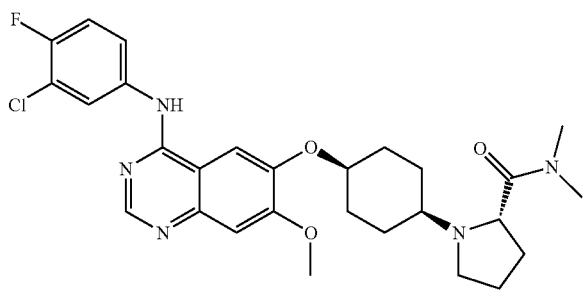 |
| (8) | 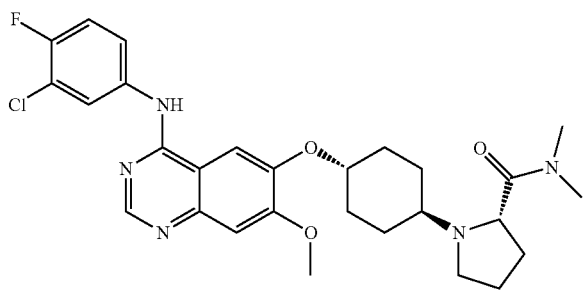 |
| (9) | 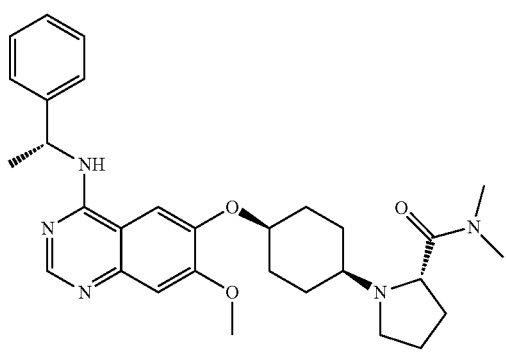 |
| (10) | 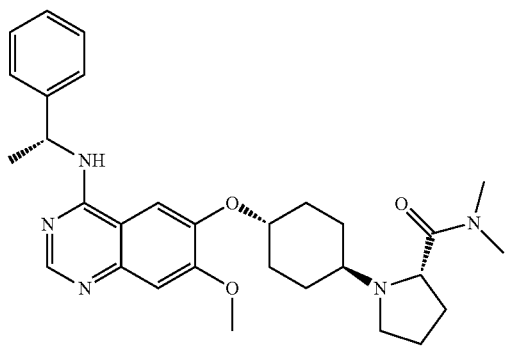 |

| Example No. | Structure |
|---|---|
| (11) | 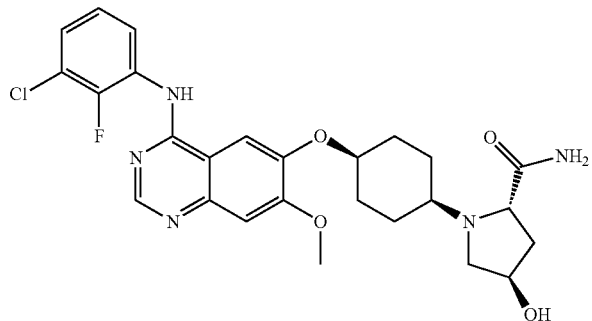 |
| (12) | 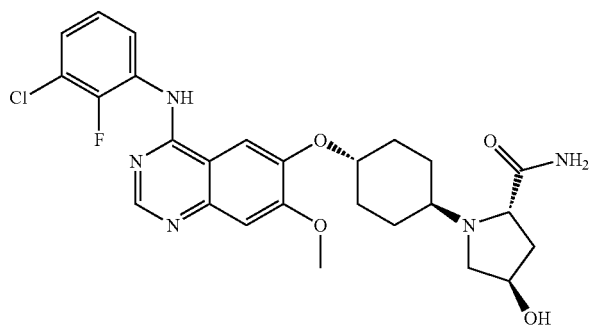 |
| (13) | 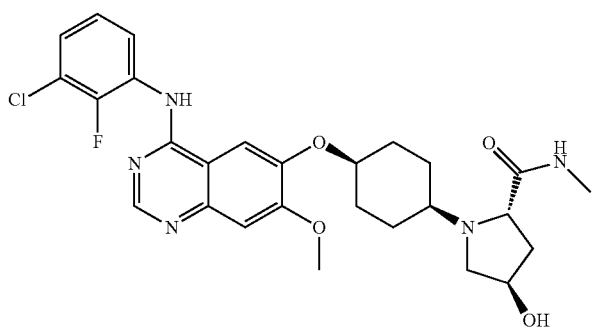 |
| (14) | 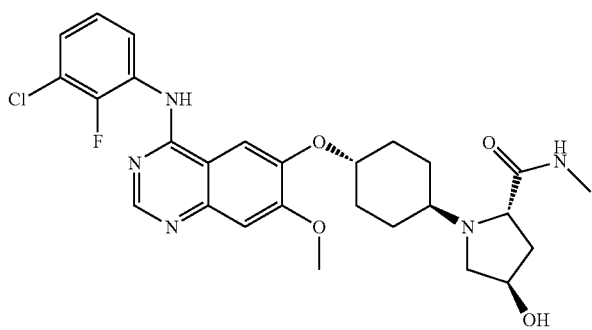 |

| Example No. | Structure |
|---|---|
| (15) | 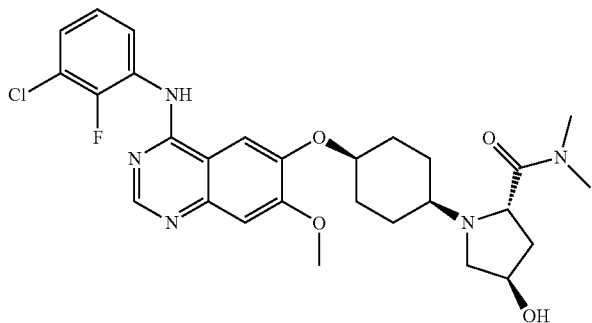 |
| (16) | 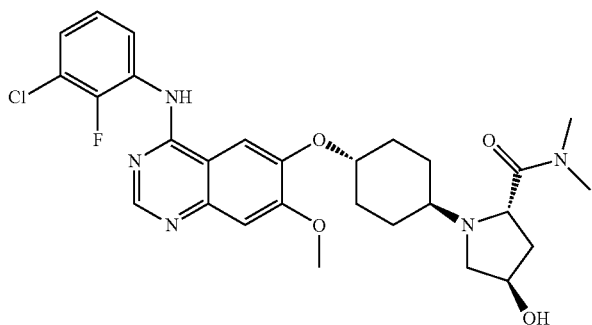 |
| (17) | 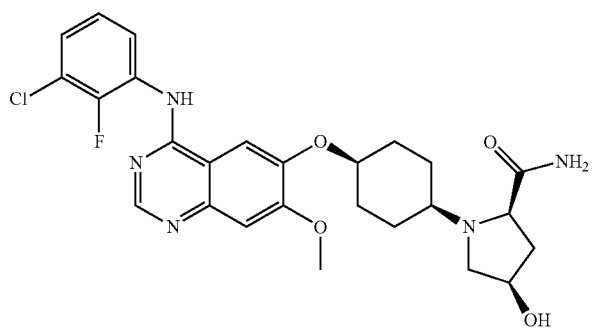 |
| (18) | 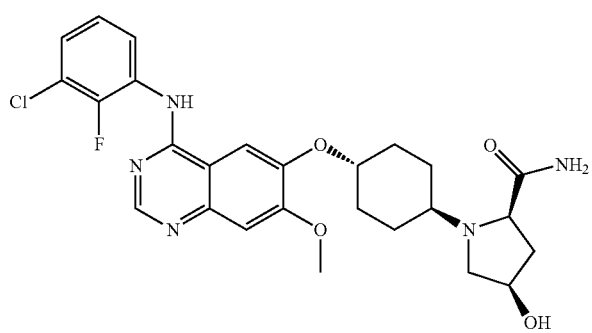 |

| Example No. | Structure |
| --- | --- |
| (19) | 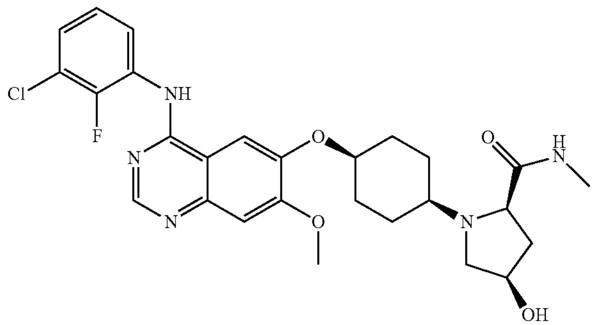 |
| (20) | 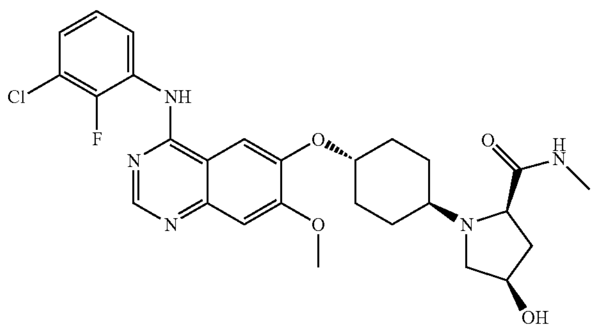 |
| (21) | 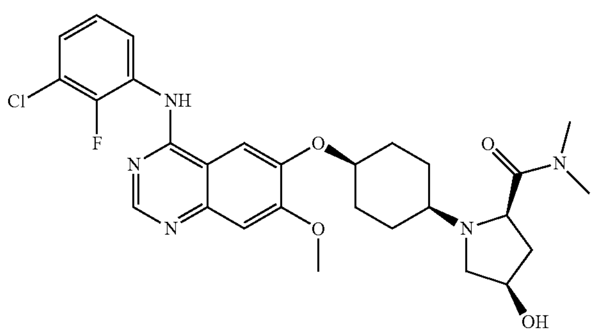 |
| (22) | 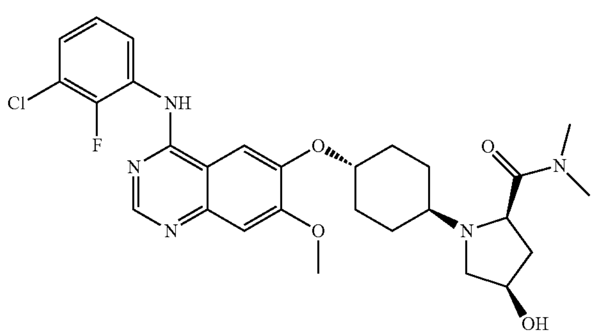 |

| Example No. | Structure |
|---|---|
| (23) | 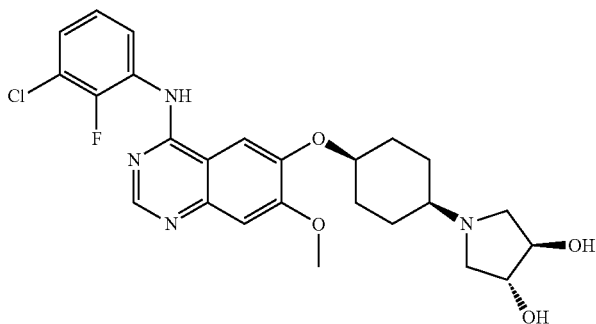<br>Carried out according to Example 1 in tetrahydrofuran<br>Mass spectrum (ESI$^+$): m/z = 503, 505 [M + H]$^+$<br>(3R,4R)-3,4-dihydroxypyrrolidine: cf for example Tetrahedron, 63(5), 1243-1253; 2006 |
| (24) | 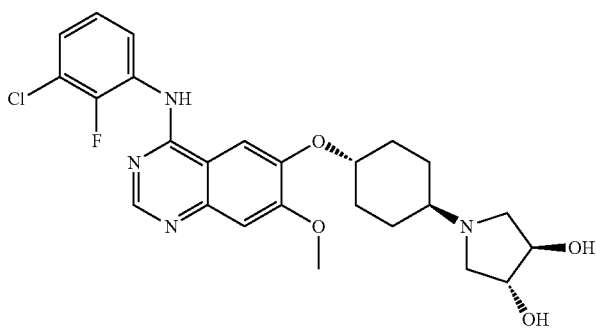<br>Carried out according to Example 1 in tetrahydrofuran<br>Mass spectrum (ESI+): m/z = 503, 505 [M + H]+<br>(3R,4R)-3,4-dihydroxypyrrolidine: cf for example Tetrahedron, 63(5), 1243-1253; 2006 |
| (25) | 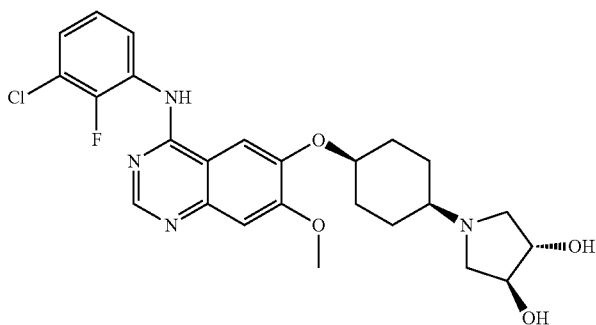<br>Carried out according to Example 1 in tetrahydrofuran<br>Mass spectrum (ESI+): m/z = 503, 505 [M + H]+<br>(3S,4S)-3,4-dihydroxypyrrolidine: cf for example Helvetica Chimica Acta, 87(12), 3167-3181; 2004 |

| Example No. | Structure |
|---|---|
| (26) | 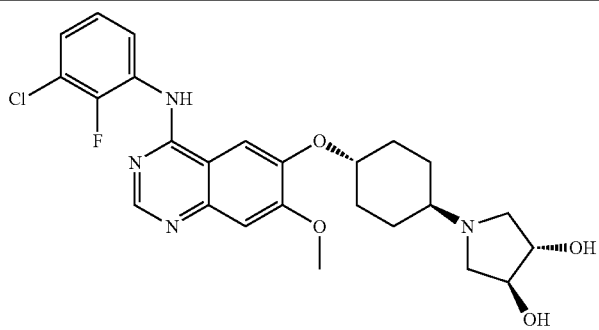<br>Carried out according to Example 1 in tetrahydrofuran<br>Mass spectrum (ESI+): m/z = 503, 505 [M + H]+<br>(3S,4S)-3,4-dihydroxypyrrolidine: cf for example Helvetica Chimica Acta, 87(12), 3167-3181; 2004 |
| (27) | 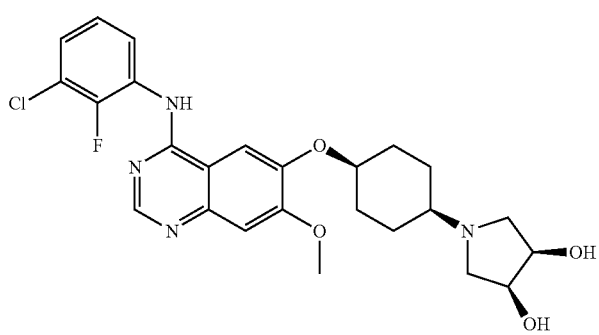 |
| (28) | 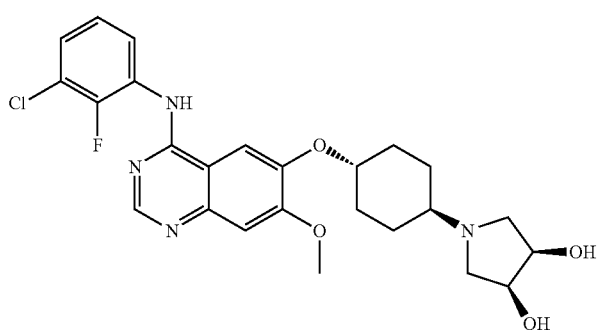 |
| (29) | 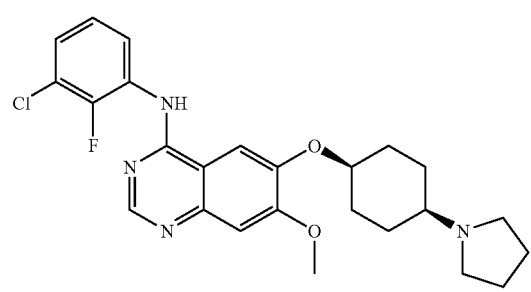 |

-continued
| Example No. | Structure |
|---|---|
| (30) | 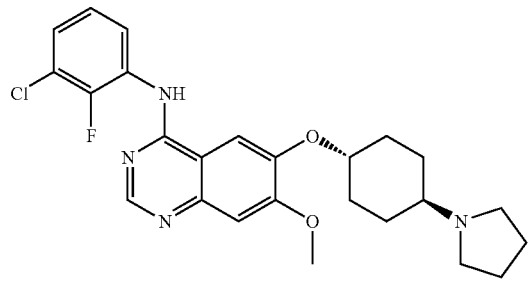 |
| (31) | 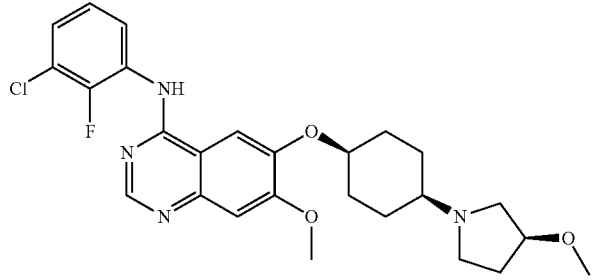 |
| (32) | 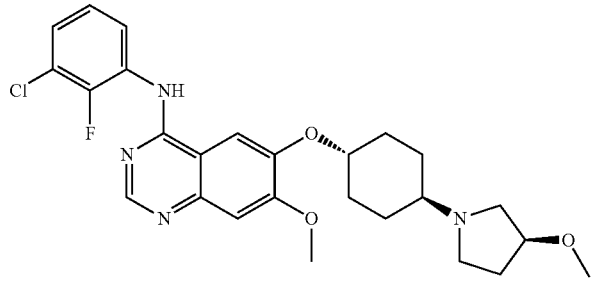 |
| (33) | 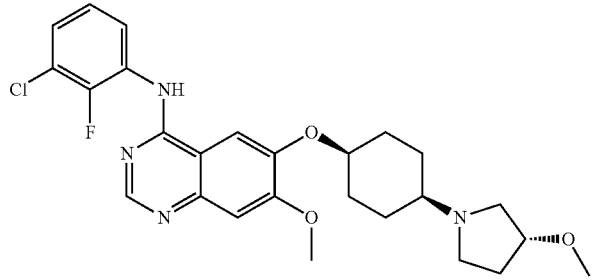 |
| (34) | 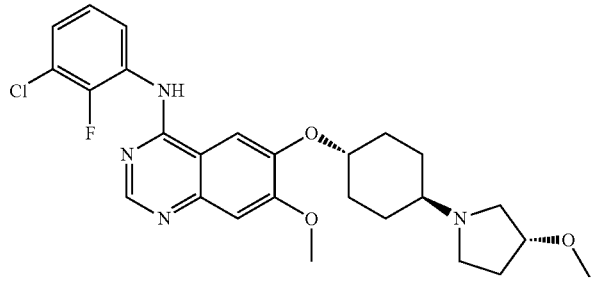 |

| Example No. | Structure |
|---|---|
| (35) | 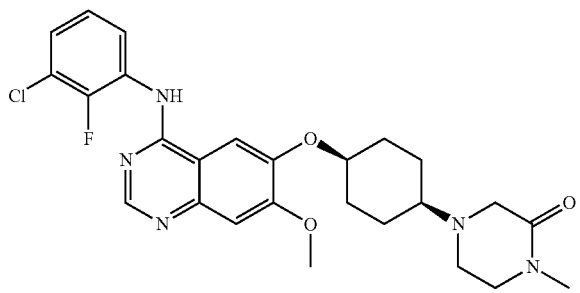<br>Carried out according to Example 1 in<br>tetrahydrofuran<br>or 1,2-dichloroethane<br>Mass spectrum (ESI$^+$): m/z = 514, 516 [M + H]$^+$ |
| (36) | 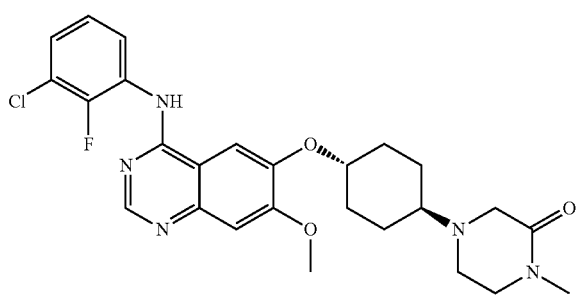<br>Carried out according to Example 1 in<br>tetrahydrofuran<br>or 1,2-dichloroethane<br>Mass spectrum (ESI$^+$): m/z = 514, 516 [M + H]$^+$ |
| (37) | 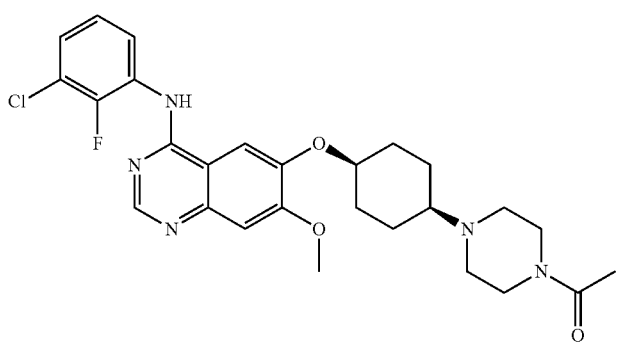 |
| (38) | 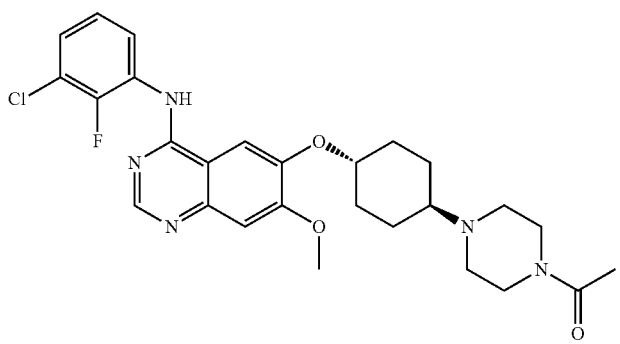 |

| Example No. | Structure |
|---|---|
| (39) | 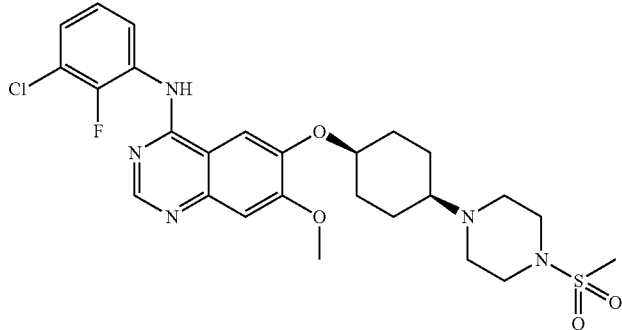 |
| (40) | 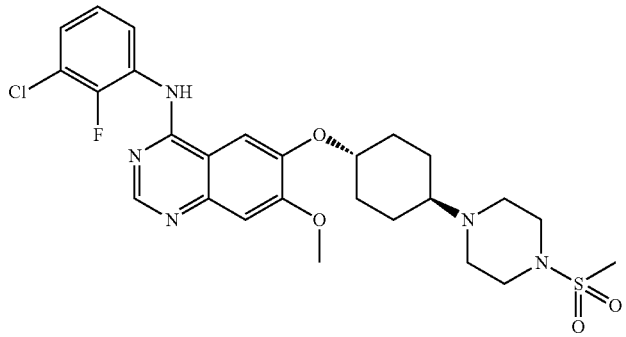 |
| (41) | 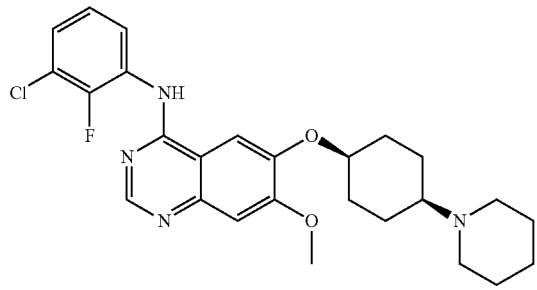 |
| (42) | 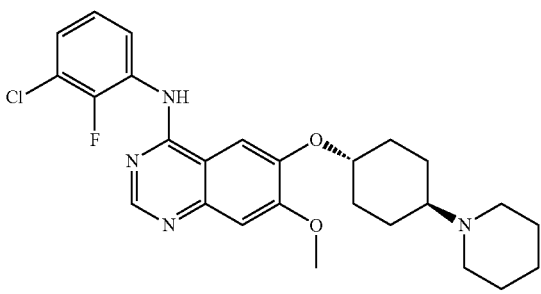 |

| Example No. | Structure |
|---|---|
| (43) | 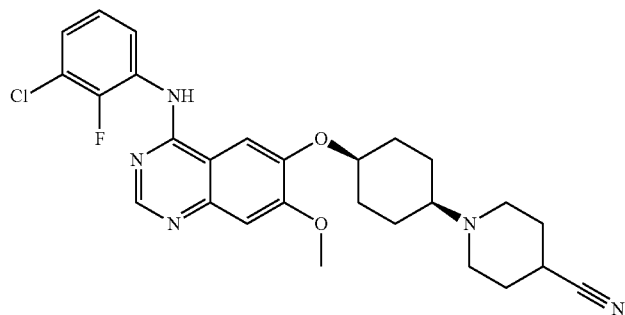<br>Carried out according to Example 1 in tetrahydrofuran<br>Mass spectrum (ESI$^+$): m/z = 510, 512 [M + H]$^+$ |
| (44) | 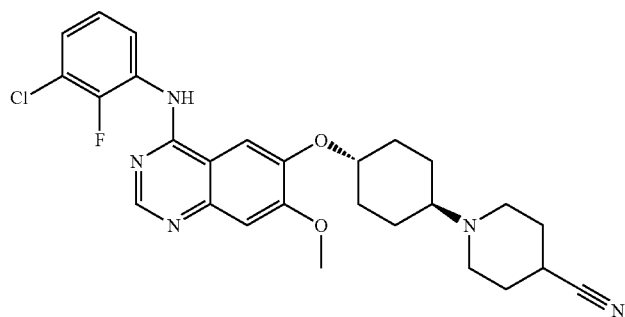<br>Carried out according to Example 1 in tetrahydrofuran<br>Mass spectrum (ESI$^+$): m/z = 510, 512 [M + H]$^+$ |
| (45) | 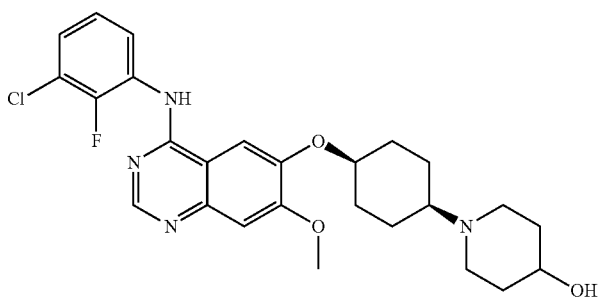<br>Carried out according to Example 1 in tetrahydrofuran<br>Mass spectrum (ESI$^+$): m/z = 501, 503 [M + H]$^+$ |

| Example No. | Structure |
|---|---|
| (46) | 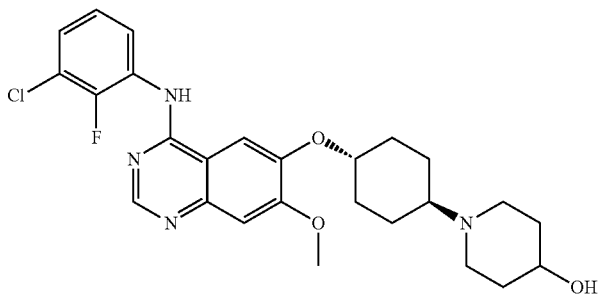 Carried out according to Example 1 in tetrahydrofuran<br>Mass spectrum (ESI$^+$): m/z = 501, 503 [M + H]$^+$ |
| (47) | 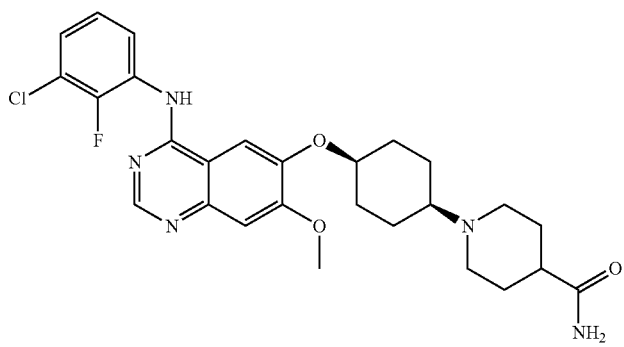 |
| (48) | 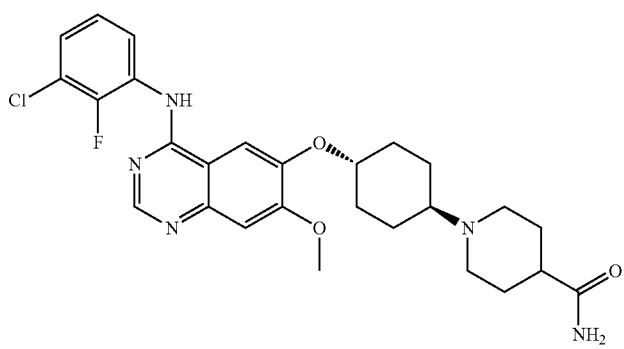 |
| (49) | 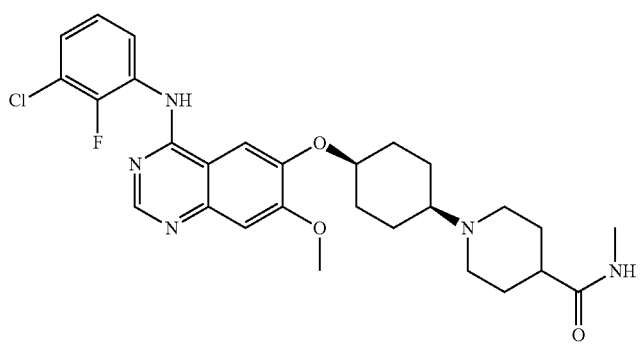 |

| Example No. | Structure |
|---|---|
| (50) | 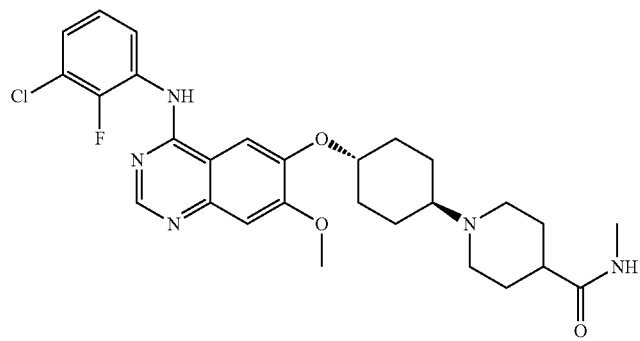 |
| (51) | 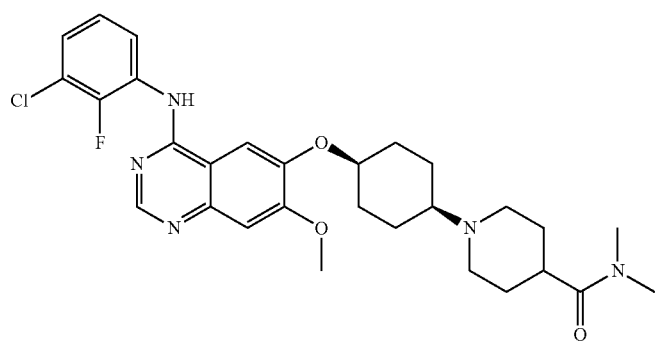 |
| (52) | 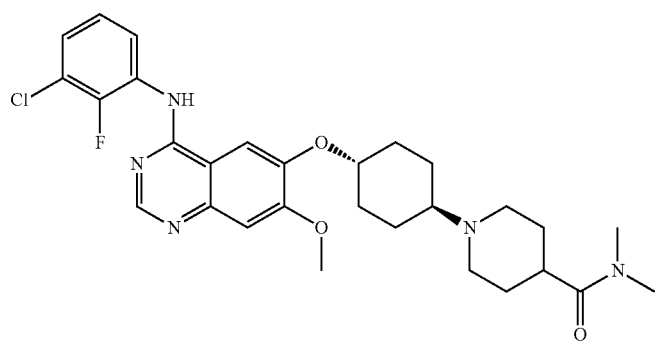 |
| (53) | 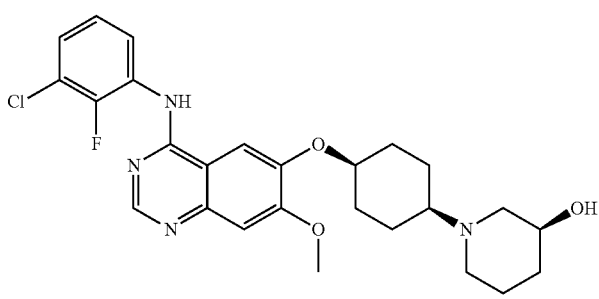 |

| Example No. | Structure |
|---|---|
| (54) | 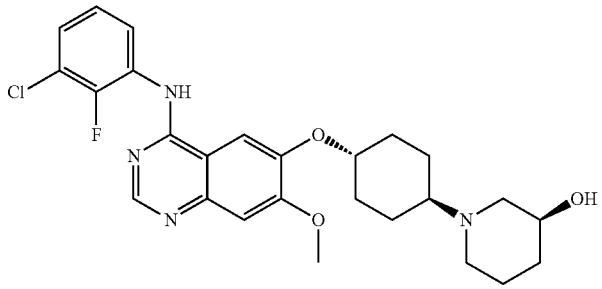 |
| (55) | 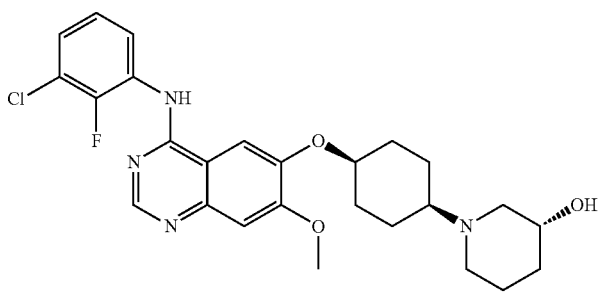 |
| (56) | 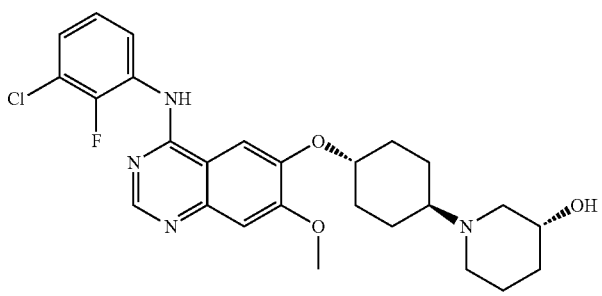 |
| (57) | 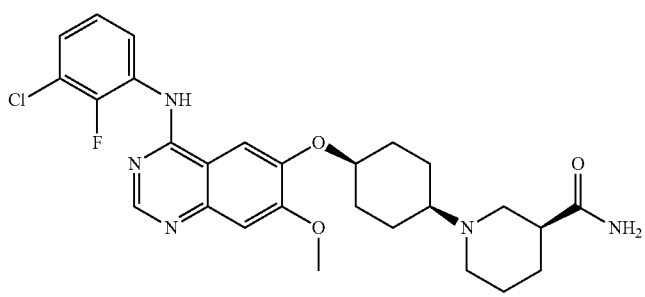 |
| (58) | 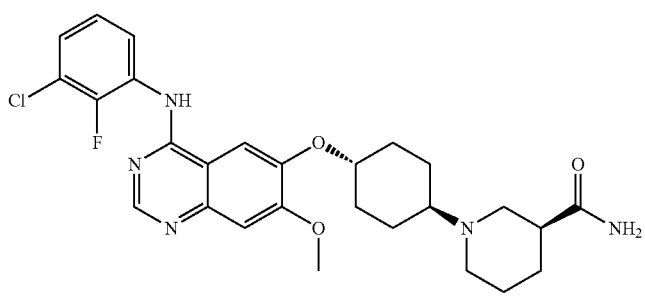 |

| Example No. | Structure |
|---|---|
| (59) | 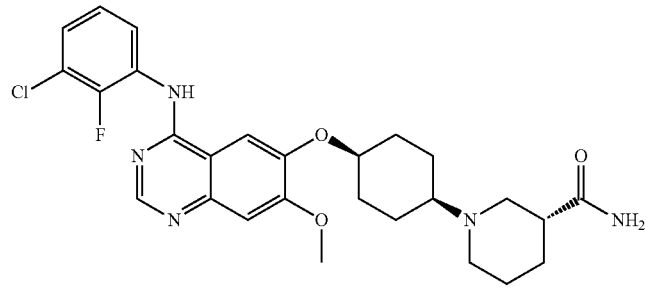 |
| (60) | 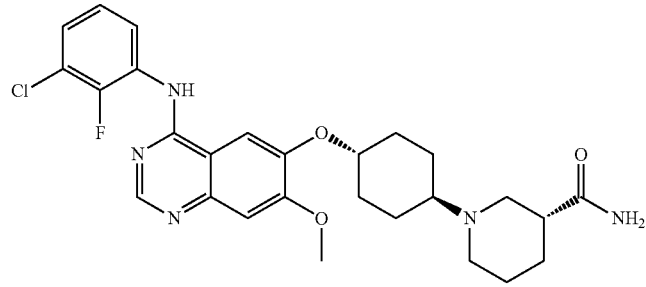 |
| (61) | 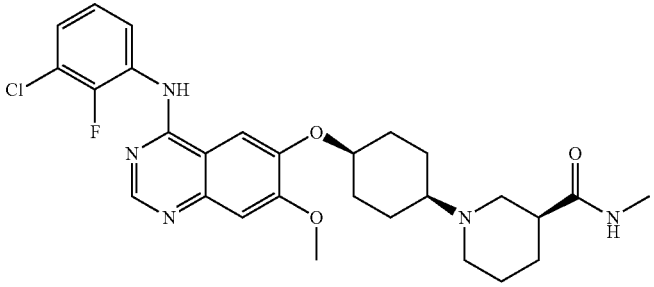 |
| (62) | 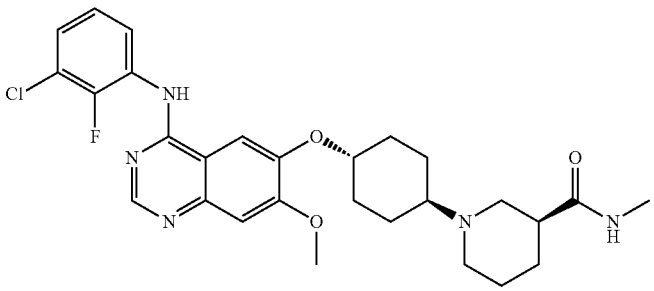 |
| (63) | 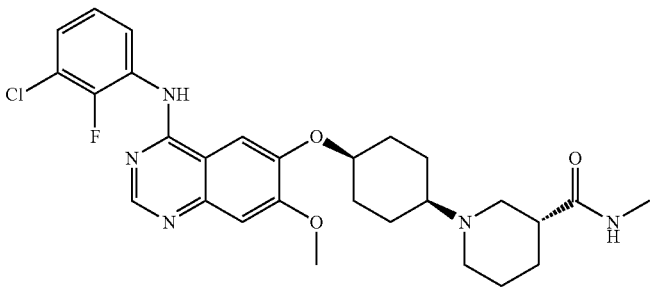 |

| Example No. | Structure |
|---|---|
| (64) | 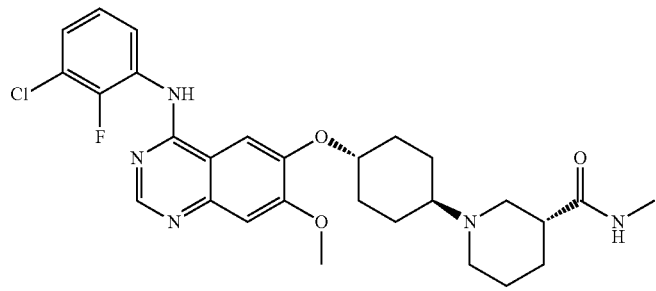 |
| (65) | 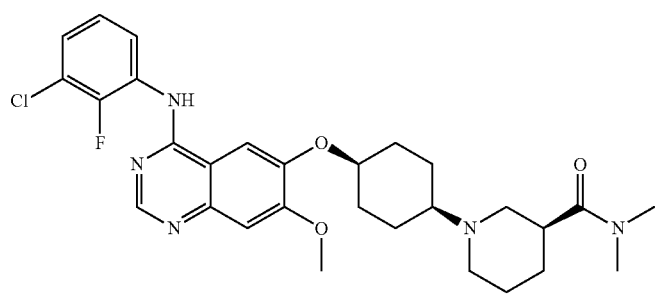 |
| (66) | 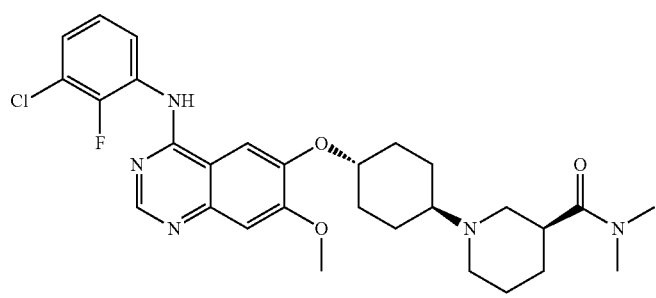 |
| (67) | 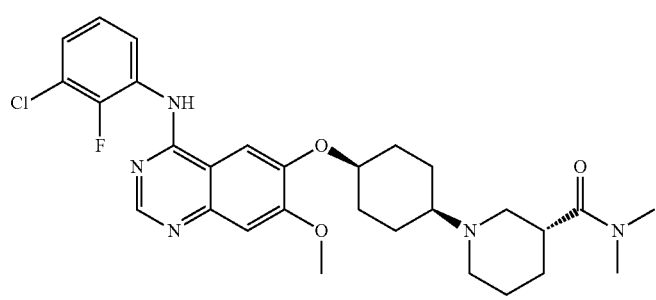 |
| (68) | 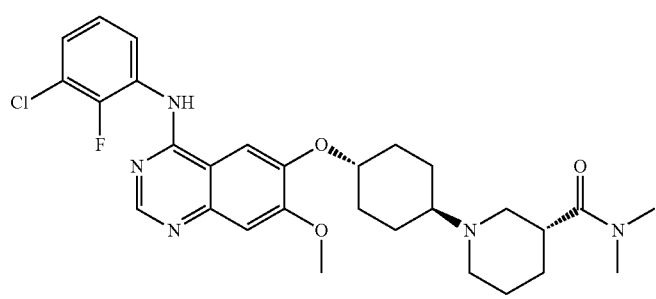 |

| Example No. | Structure |
|---|---|
| (69) | 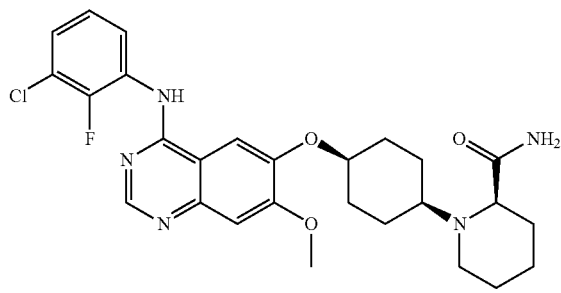 |
| (70) | 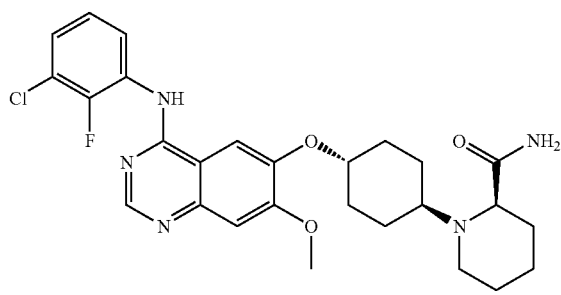 |
| (71) | 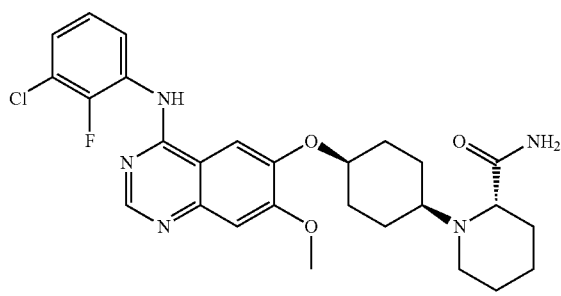 |
| (72) | 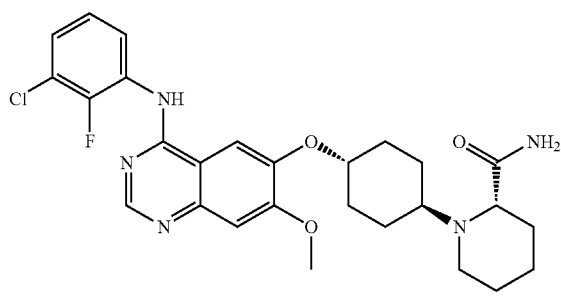 |
| (73) | 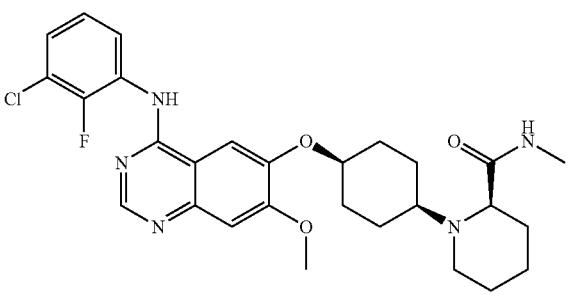 |

| Example No. | Structure |
|---|---|
| (74) | 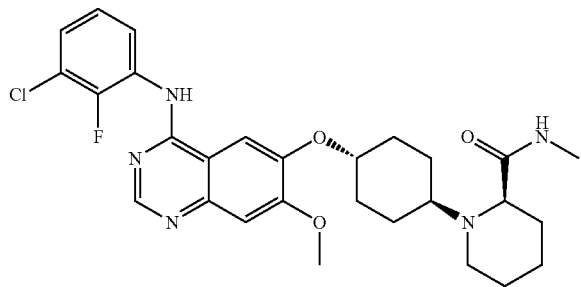 |
| (75) | 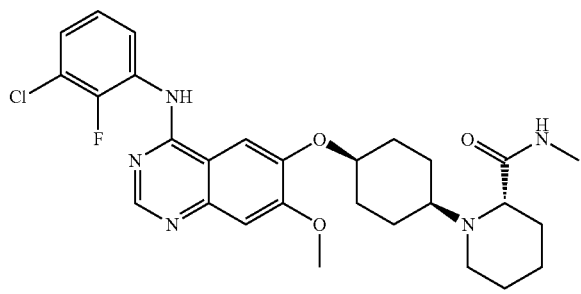 |
| (76) | 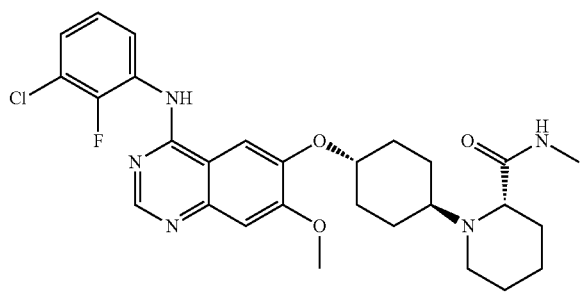 |
| (77) | 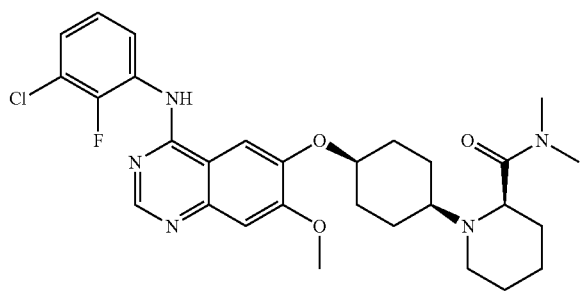 |
| (78) | 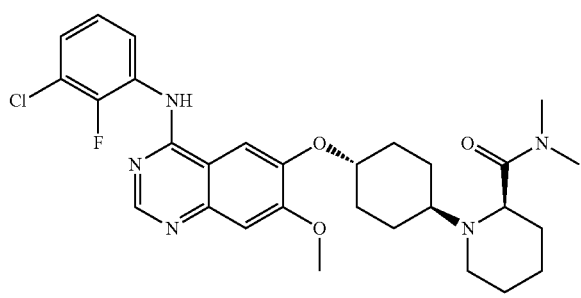 |

| Example No. | Structure |
|---|---|
| (79) | 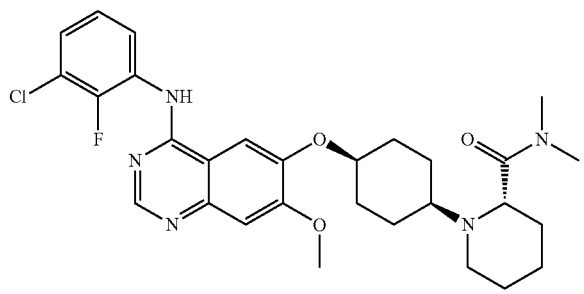 |
| (80) | 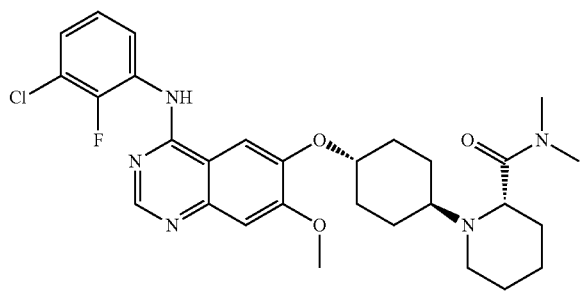 |
| (81) | 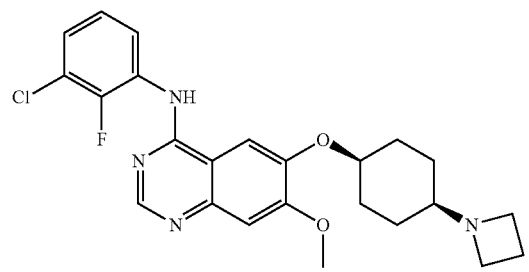 |
| (82) | 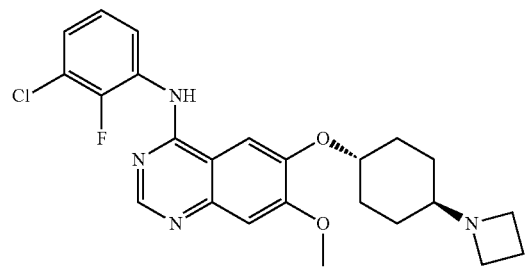 |
| (83) | 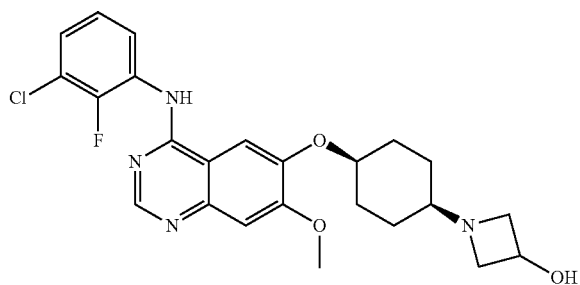 |
Carried out according to Example 1 in tetrahydrofuran
Mass spectrum (ESI$^+$): m/z = 473, 475 [M + H]$^+$

| Example No. | Structure |
|---|---|
| (84) | 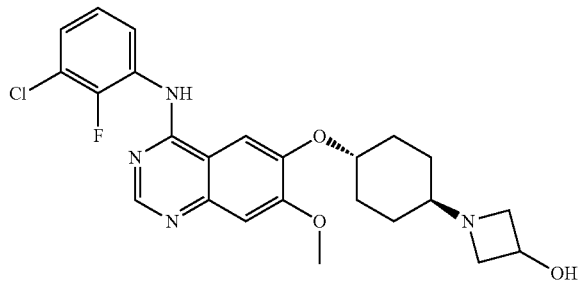 Carried out according to Example 1 in tetrahydrofuran<br>Mass spectrum (ESI$^+$): m/z = 473, 475 [M + H]$^+$ |
| (85) | 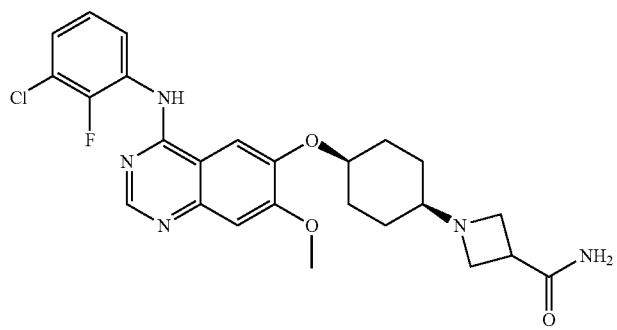 |
| (86) | 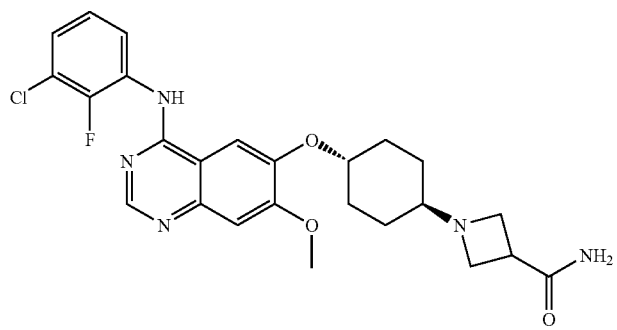 |
| (87) | 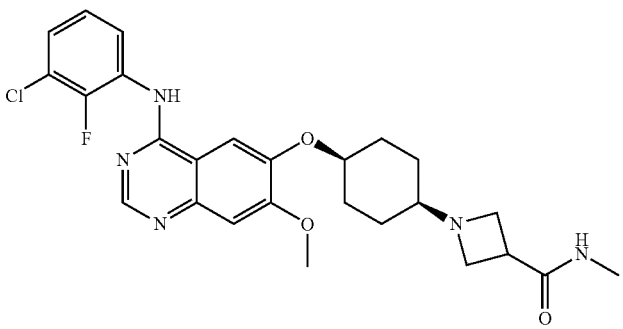 |

| Example No. | Structure |
|---|---|
| (88) | 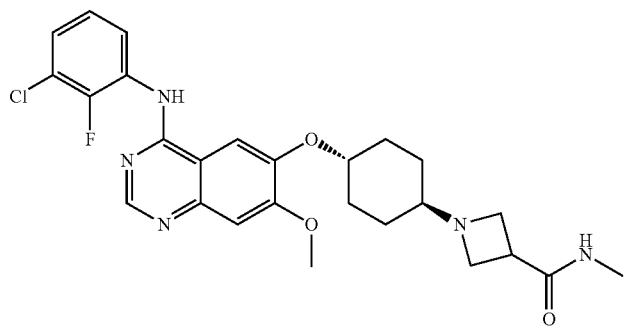 |
| (89) | 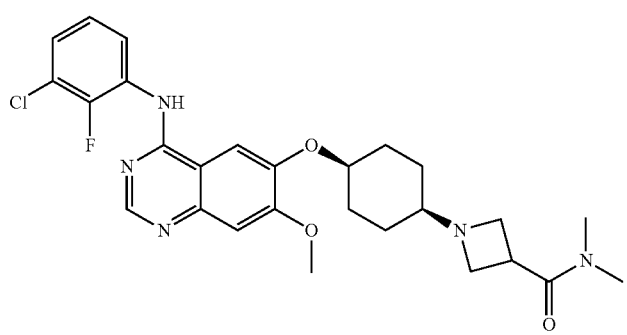 |
| (90) | 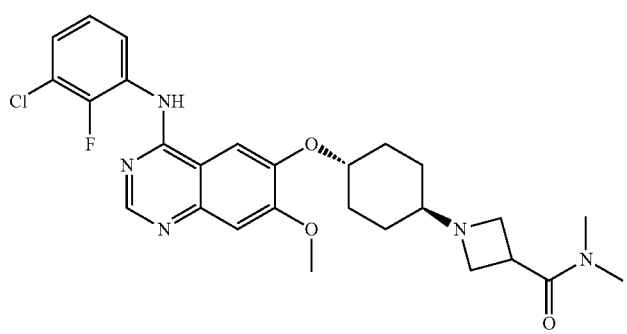 |
| (91) | 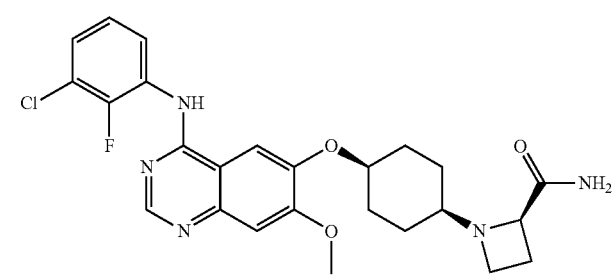 |
| (92) | 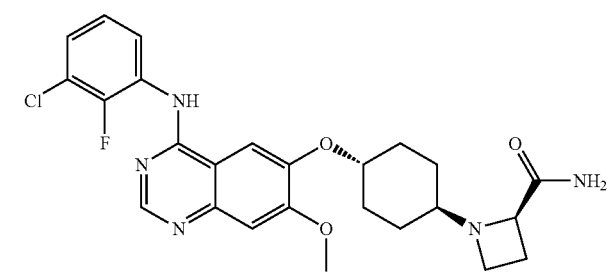 |

-continued
| Example No. | Structure |
|---|---|
| (93) | 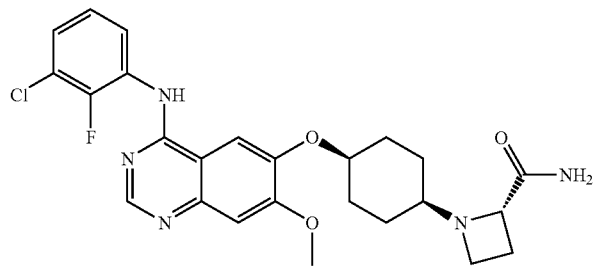 |
| (94) | 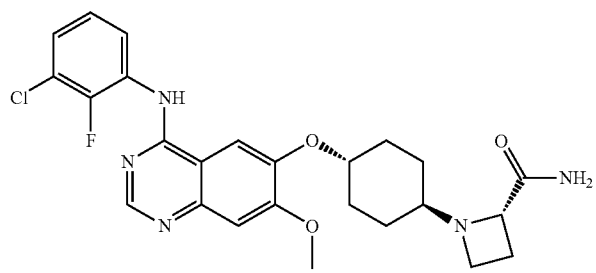 |
| (95) | 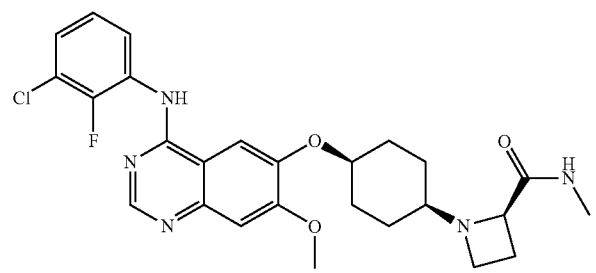 |
| (96) | 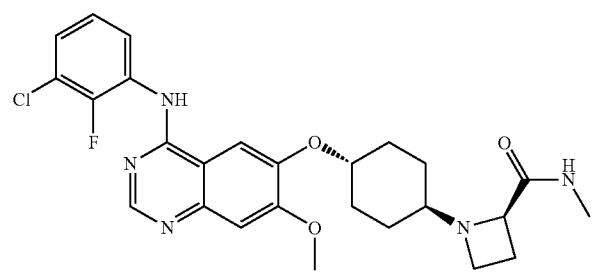 |
| (97) | 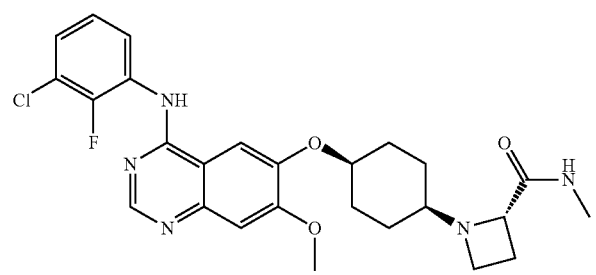 |

| Example No. | Structure |
|---|---|
| (98) | 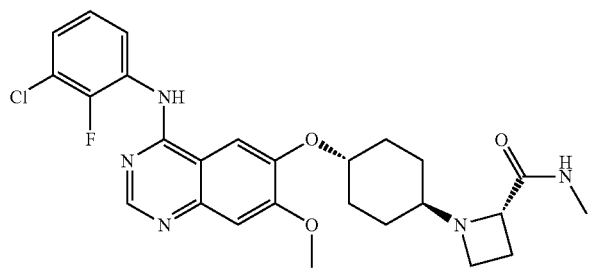 |
| (99) | 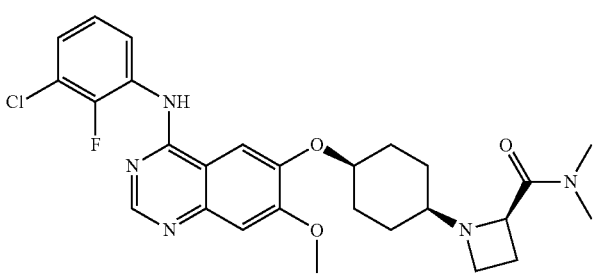 |
| (100) | 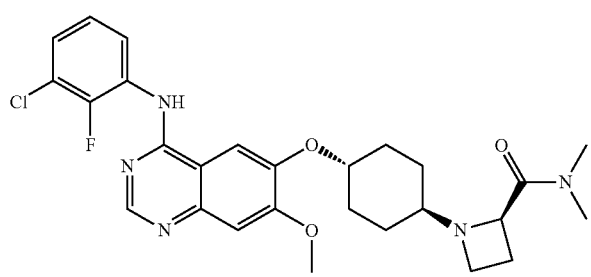 |
| (101) | 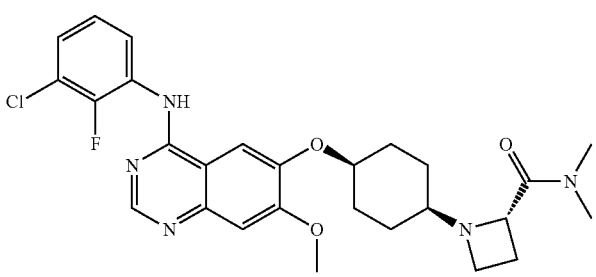 |
| (102) | 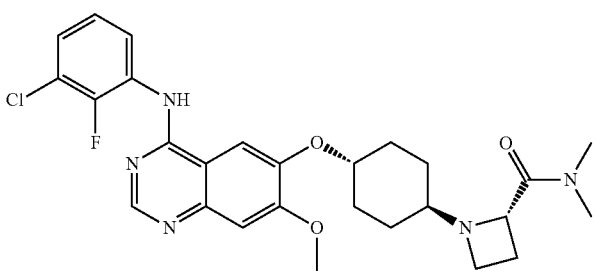 |

| Example No. | Structure |
|---|---|
| (103) | 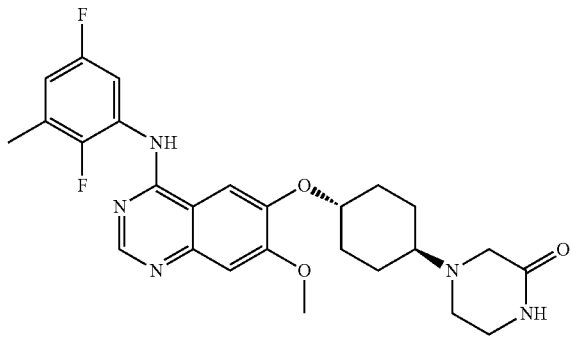 |
| (104) | 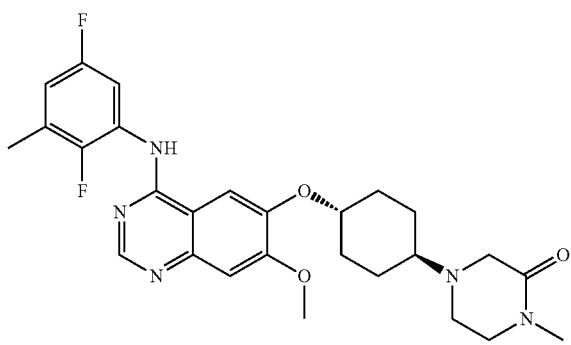 |
| (105) | 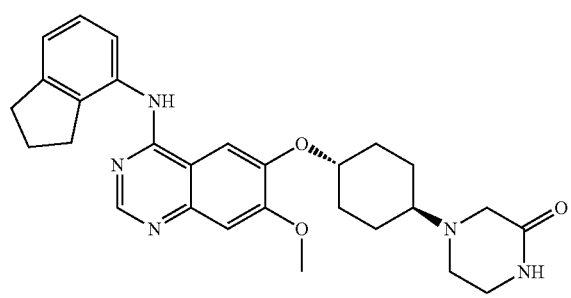<br>Carried out according to Example 1 in tetrahydrofuran<br>Mass spectrum (ESI$^+$): m/z = 488 [M + H]$^+$ |
| (106) | 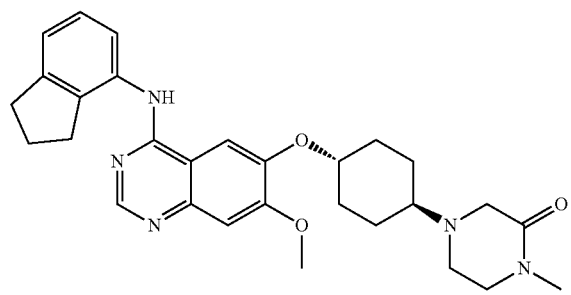<br>Carried out according to Example 1 in dichloromethane<br>Mass spectrum (ESI$^+$): m/z = 502 [M + H]$^+$ |

| Example No. | Structure |
|---|---|
| (107) | 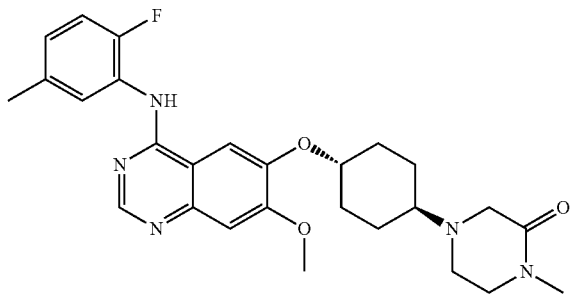<br>Carried out according to Example 1 in dichloromethane<br>Mass spectrum (ESI⁺): m/z =494 [M + H]⁺ |
| (108) | 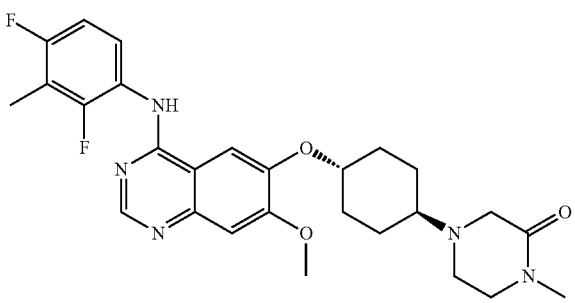 |
| (109) | 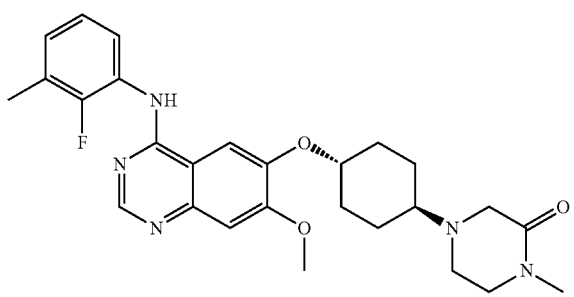<br>Carried out according to Example 1 in 1,2-dichloroethane<br>Mass spectrum (ESI⁺): m/z = 494 [M + H]⁺ |
| (110) | 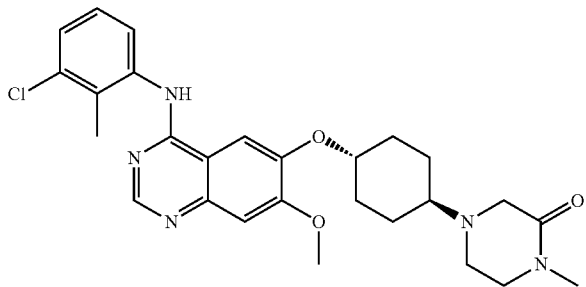<br>Carried out according to Example 1 in dichloromethane<br>Mass spectrum (ESI⁺): m/z = 510, 512 [M + H]⁺ |

-continued
| Example No. | Structure |
|---|---|
| (111) | 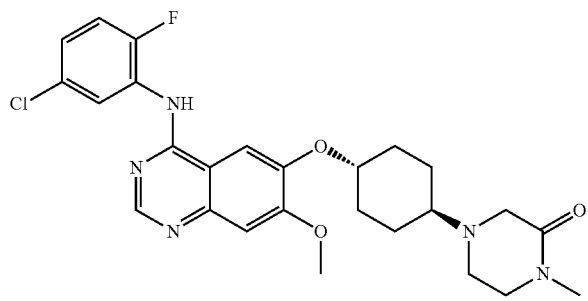 |
| (112) | 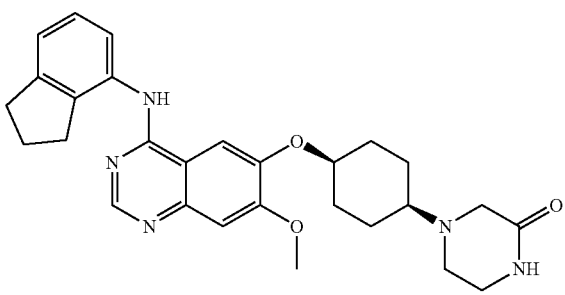
Carried out according to Example 1 in tetrahydrofuran
Mass spectrum (ESI$^+$): m/z = 488 [M + H]$^+$ |
| (113) | 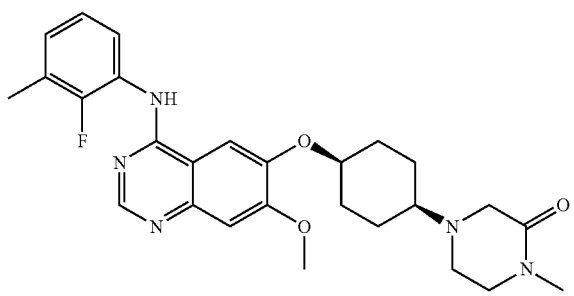
Carried out according to Example 1 in 1,2-dichloroethane
Mass spectrum (ESI$^+$): m/z = 494 [M + H]$^+$ |
| (114) | 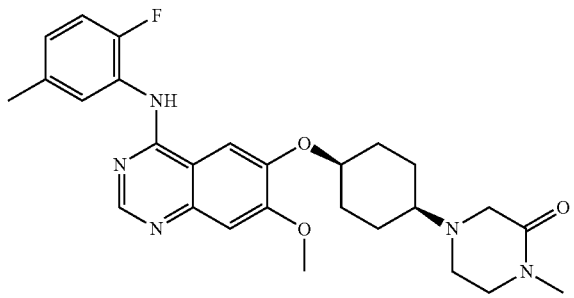
Carried out according to Example 1 in dichloromethane
Mass spectrum (ESI$^+$): m/z = 494 [M + H]$^+$ |

| Example No. | Structure |
|---|---|
| (115) | 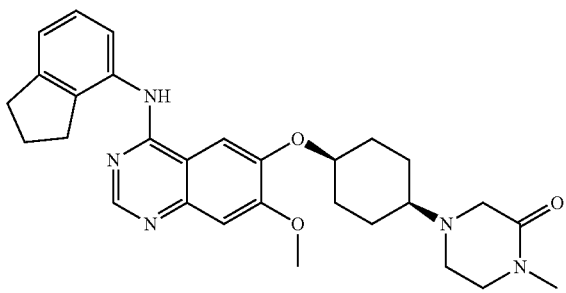<br>Carried out according to Example 1 in dichloromethane<br>Mass spectrum (ESI$^+$): m/z = 502 [M + H]$^+$ |
| (116) | 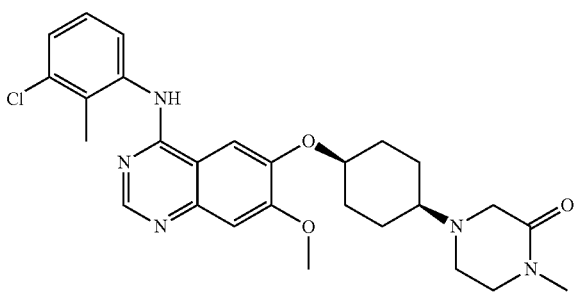<br>Carried out according to Example 1 in dichloromethane<br>Mass spectrum (ESI$^+$): m/z = 510, 512 [M + H]$^+$ |

EXAMPLE 2

Coated Tablets Containing 75 mg of Active Substance

1 Tablet Core Contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl-pyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance

Composition:

1 Tablet Contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 4

Tablets Containing 150 mg of Active Substance

Composition:
1 Tablet Contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 5

Hard Gelatine Capsules Containing 150 mg of Active Substance

1 Capsule Contains:

| | |
|---|---|
| active substance | 50.0 mg |
| corn starch (dried) | approx. 80.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 6

Suppositories Containing 150 mg of Active Substance

1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

EXAMPLE 7

Suspension Containing 50 mg of Active Substance 100 ml of Suspension Contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. Water | ad 100 ml |

Preparation:
The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules Containing 10 mg Active Substance

Composition:

| | |
|---|---|
| active substance | 10.0 mg |
| 0.01 N hydrochloric acid | q.s. |
| double-distilled water | ad 2.0 ml |

Preparation:
The active substance is dissolved in the necessary amount of 0.01 N HCl, made isotonic with common salt, filtered sterile and transferred into 2 ml ampoules.

EXAMPLE 9

Ampoules Containing 50 mg of Active Substance

Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

EXAMPLE 10

Capsules for Powder Inhalation Containing 5 mg of Active Substance

1 Capsule Contains:

| active substance | 5.0 mg |
|---|---|
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule = | 3 |

EXAMPLE 11

Solution for Inhalation for Hand-Held Nebulisers Containing 2.5 mg Active Substance 1 Spray Contains:

| active substance | 2.500 mg |
|---|---|
| benzalkonium chloride | 0.001 mg |
| 1N hydrochloric acid | q.s. |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).
Contents of the container: 4.5 g

The invention claimed is:
1. A compound of formula (I)

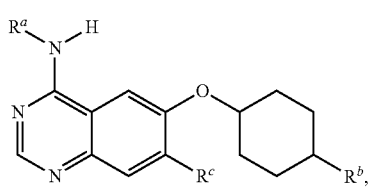

wherein
$R^a$ denotes a phenyl, 1-phenylethyl or indan-4-yl group, wherein the phenyl nucleus is substituted in each case by the groups $R^1$ to $R^3$, wherein $R^1$ and $R^2$, which may be identical or different, each denote:
a hydrogen, fluorine, chlorine, bromine or iodine atom,
a $C_{1-4}$-alkyl, hydroxy, $C_{1-4}$-alkoxy, $C_{2-3}$-alkenyl or $C_{2-3}$-alkynyl group,
an aryl, aryloxy, arylmethyl or arylmethoxy group,
a heteroaryl, heteroaryloxy, heteroarylmethyl or heteroarylmethoxy group,
a methyl or methoxy group substituted by 1 to 3 fluorine atoms or
a cyano, nitro or amino group, and
$R^3$ denotes a hydrogen, fluorine, chlorine or bromine atom or
a methyl or trifluoromethyl group,
$R^b$ denotes an azetidin-1-yl, homopiperidin-1-yl, homomorpholin-4-yl, piperazin-1-yl, 4-($C_{1-4}$-alkyl-carbonyl)-piperazin-1-yl, 4-($C_{1-4}$-alkyl-sulphonyl)-piperazin-1-yl, homopiperazin-1-yl, 4-($C_{1-4}$-alkyl-carbonyl)-homopiperazin-1-yl or 4-($C_{1-4}$-alkyl-sulphonyl)-homopiperazin-1-yl group which may be mono-, di- or trisubstituted by $R^4$ in each case, while the substituents may be identical or different and
$R^4$ denotes:
a fluorine, chlorine, bromine or iodine atom,
a $C_{1-4}$-alkyl, $C_{2-4}$-alkenyl or $C_{2-4}$-alkynyl group,
a methyl or methoxy group substituted by 1 to 3 fluorine atoms,
an amino, $C_{1-4}$-alkylamino, di-($C_{1-4}$-alkyl)amino, $C_{1-4}$-alkyl-carbonylamino, N—($C_{1-4}$-alkyl)-$C_{1-4}$-alkyl-carbonylamino, $C_{1-4}$-alkyl-sulphonylamino or N—($C_{1-4}$-alkyl)-$C_{1-4}$-alkyl-sulphonylamino group,
an amino-$C_{1-4}$-alkyl, $C_{1-4}$-alkylamino-$C_{1-4}$-alkyl, di-($C_{1-4}$-alkyl)amino-$C_{1-4}$-alkyl, $C_{1-4}$-alkyl-carbonylamino-$C_{1-4}$-alkyl, N—($C_{1-4}$-alkyl)-$C_{1-4}$-alkyl-carbonylamino-$C_{1-4}$-alkyl, $C_{1-4}$-alkyl-sulphonylamino-$C_{1-4}$-alkyl or N—($C_{1-4}$-alkyl)-$C_{1-4}$-alkyl-sulphonylamino-$C_{1-4}$-alkyl group,
a hydroxy, $C_{1-4}$-alkyloxy or $C_{1-4}$-alkyl-carbonyloxy group
a hydroxy-$C_{1-4}$-alkyl, $C_{1-4}$-alkyloxy-$C_{1-4}$-alkyl or $C_{1-4}$-alkyl-carbonyloxy-$C_{1-4}$-alkyl group,
a $C_{1-4}$-alkyl-carbonyl, cyano, $C_{1-4}$-alkyl-oxycarbonyl, carboxy, aminocarbonyl, $C_{1-4}$-alkyl-aminocarbonyl, di-($C_{1-4}$-alkyl)amino-carbonyl, pyrrolidin-1-yl-carbonyl, piperidin-1-yl-carbonyl, piperazin-1-yl-carbonyl, 4-$C_{1-4}$-alkyl-piperazin-1-yl-carbonyl or morpholin-4-yl-carbonyl group,
a $C_{1-4}$-alkylcarbonyl-$C_{1-4}$-alkyl, cyano-$C_{1-4}$-alkyl, $C_{1-4}$-alkyloxycarbonyl-$C_{1-4}$-alkyl, aminocarbonyl-$C_{1-4}$-alkyl, $C_{1-4}$-alkylaminocarbonyl-$C_{1-4}$-alkyl, di-($C_{1-4}$-alkyl)aminocarbonyl-$C_{1-4}$-alkyl, pyrrolidin-1-yl-carbonyl-$C_{1-4}$-alkyl, piperidin-1-yl-carbonyl-$C_{1-4}$-alkyl, piperazin-1-yl-carbonyl-$C_{1-4}$-alkyl, 4-$C_{1-4}$-alkyl-piperazin-1-yl-carbonyl-$C_{1-4}$-alkyl or morpholin-4-yl-carbonyl-$C_{1-4}$-alkyl group,
a $C_{1-4}$-alkylsulphanyl, $C_{1-4}$-alkylsulphinyl, $C_{1-4}$-alkylsulphonyl, aminosulphonyl, $C_{1-4}$-alkyl-aminosulphonyl or di-($C_{1-4}$-alkyl)amino-sulphonyl group,
a $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, aminosulphonyl-$C_{1-4}$-alkyl, $C_{1-4}$-alkyl-aminosulphonyl-$C_{1-4}$-alkyl or di-($C_{1-4}$-alkyl)amino-sulphonyl-$C_{1-4}$-alkyl group
and wherein the heterocycles mentioned under $R^b$ above may additionally be substituted by an oxo group, $R^c$ denotes:

a hydrogen atom, a fluorine, chlorine, bromine or iodine atom, a $C_{1-4}$-alkyl group, a $C_{1-4}$-alkyl group which is substituted by an $R^5$ group, where $R^5$ denotes a hydroxy, $C_{1-3}$-alkyloxy, $C_{3-6}$-cycloalkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, 2-oxa-5-aza-bicyclo[2,2,1]hept-5-yl, 3-oxa-8-aza-bicyclo[3.2.1]oct-8-yl, 8-oxa-3-aza-bicyclo-[3.2.1]oct-3-yl, piperazin-1-yl, 4-$C_{1-3}$-alkyl-piperazin-1-yl, homopiperazin-1-yl or $C_{1-3}$-alkyl-homopiperazin-1-yl group or $R^5$ denotes a formylamino, $C_{1-4}$-alkylcarbonylamino, $C_{1-3}$-alkyloxy-$C_{1-3}$-alkyl-carbonylamino, $C_{1-4}$-alkyloxycarbonylamino, aminocarbonylamino, $C_{1-3}$-alkylaminocarbonylamino, di-($C_{1-3}$-alkyl)aminocarbonylamino, pyrrolidin-1-ylcarbonylamino, piperidin-1-ylcarbonylamino, piperazin-1-ylcarbonylamino, 4-$C_{1-3}$-alkyl-piperazin-1-ylcarbonylamino, morpholin-4-ylcarbonylamino or a $C_{1-4}$-alkylsulphonylamino group, a hydroxy group, a $C_{1-4}$-alkyloxy group, methoxy or ethyloxy group substituted by 1 to 3 fluorine atoms, a $C_{2-4}$-alkyloxy group which is substituted by the group $R^5$, where $R^5$ is as hereinbefore defined, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a $C_{1-4}$-alkoxy group which is substituted by a pyrrolidinyl, piperidinyl or homopiperidinyl group substituted in the 1 position by the group $R^6$, where $R^6$ denotes a hydrogen atom or a $C_{1-3}$-alkyl group, or a $C_{1-4}$-alkoxy group which is substituted by a morpholinyl group substituted in the 4 position by the group $R^6$, where $R^6$ is as hereinbefore defined, and wherein the pyrrolidinyl, piperidinyl, piperazinyl and morpholinyl groups mentioned above in the definition of the group $R^c$ may each be substituted by one or two $C_{1-3}$-alkyl groups, and wherein by the aryl groups mentioned in the definition of the foregoing groups is meant in each case a phenyl group which is mono- or disubstituted by $R^7$, wherein the substituents may be identical or different and $R^7$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, and by the heteroaryl groups mentioned in the definition of the foregoing groups is meant a pyridyl, pyridazinyl, pyrimidinyl or pyrazinyl group, wherein the above-mentioned heteroaryl groups are mono- or disubstituted by the group $R^7$, wherein the substituents may be identical or different and $R^7$ is as hereinbefore defined, and unless stated otherwise, the above-mentioned alkyl groups may be straight-chain or branched, a tautomer, stereoisomer, mixture thereof or physiologically acceptable salt thereof.

2. The compound of formula (I) according to claim 1, wherein $R^a$ denotes a phenyl, 1-phenylethyl or indan-4-yl group, wherein the phenyl nucleus is substituted in each case by the groups $R^1$ to $R^3$, wherein $R^1$ denotes:

a hydrogen, fluorine, chlorine or bromine atom, a methyl, trifluoromethyl or ethynyl group, a phenyloxy or phenylmethoxy group, wherein the phenyl moiety of the above-mentioned groups may optionally be substituted by a fluorine or chlorine atom, or a pyridyloxy or pyridinylmethoxy group, wherein the pyridinyl moiety of the above-mentioned groups is optionally substituted by a methyl or trifluoromethyl group, $R^2$ denotes a hydrogen, fluorine or chlorine atom or a methyl group and $R^3$ denotes a hydrogen atom, $R^b$ denotes an azetidin-1-yl, homopiperidin-1-yl, homomorpholin-4-yl, piperazin-1-yl, 4-($C_{1-3}$-alkyl-carbonyl)-piperazin-1-yl, 4-($C_{1-3}$-alkyl-sulphonyl)piperazin-1-yl, homopiperazin-1-yl, 4-($C_{1-3}$-alkyl-carbonyl)-homopiperazin-1-yl or 4-($C_{1-3}$-alkyl-sulphonyl)-homopiperazin-1-yl group which may be mono- or disubstituted in each case by $R^4$, wherein the substituents may be identical or different and $R^4$ denotes:

a fluorine atom, a $C_{1-3}$-alkyl group, an amino, $C_{1-3}$-alkylamino, di-($C_{1-3}$-alkyl)amino, $C_{1-3}$-alkyl-carbonylamino, N—($C_{1-3\text{-}alkyl})$-$C_{1-3}$-alkyl-carbonylamino, $C_{1-3}$-alkyl-sulphonylamino or N—($C_{1-3}$-alkyl)-$C_{1-3}$-alkyl-sulphonylamino group, an amino-$C_{1-3}$-alkyl, $C_{1-3}$-alkylamino-$C_{1-3}$-alkyl, di-($C_{1-3}$-alkyl)amino-$C_{1-3}$-alkyl, $C_{1-3}$-alkyl-carbonylamino-$C_{1-3}$-alkyl, N—($C_{1-3}$-alkyl)-$C_{1-3}$-alkyl-carbonylamino-$C_{1-3}$-alkyl, $C_{1-3}$-alkyl-sulphonylamino-$C_{1-3}$-alkyl or N—($C_{1-3}$-alkyl)-$C_{1-3}$-alkyl-sulphonylamino-$C_{1-3}$-alkyl group, a hydroxy, $C_{1-3}$-alkyloxy or $C_{1-3}$-alkyl-carbonyloxy group, a hydroxy-$C_{1-3}$-alkyl, $C_{1-3}$-alkyloxy-$C_{1-3}$-alkyl or $C_{1-3}$-alkyl-carbonyloxy-$C_{1-3}$-alkyl group, a $C_{1-3}$-alkyl-carbonyl, cyano, $C_{1-4}$-alkyl-oxycarbonyl, carboxy, aminocarbonyl, $C_{1-3}$-alkyl-aminocarbonyl or di-($C_{1-3}$-alkyl)amino-carbonyl-group, a $C_{1-3}$-alkylcarbonyl-$C_{1-3}$-alkyl, cyano-$C_{1-3}$-alkyl, $C_{1-4}$-alkyloxycarbonyl-$C_{1-3}$-alkyl-group, aminocarbonyl-$C_{1-3}$-alkyl, $C_{1-3}$-alkylaminocarbonyl-$C_{1-3}$-alkyl or di-($C_{1-3}$-alkyl)aminocarbonyl-$C_{1-3}$-alkyl group, a $C_{1-4}$-alkylsulphanyl, $C_{1-4}$-alkylsulphinyl, $C_{1-4}$-alkylsulphonyl, aminosulphonyl, $C_{1-3}$-alkyl-aminosulphonyl or di-($C_{1-3}$-alkyl)aminosulphonyl group, a $C_{1-4}$-alkylsulphanyl-$C_{1-3}$-alkyl, $C_{1-4}$-alkylsulphinyl-$C_{1-3}$-alkyl, $C_{1-4}$-alkylsulphonyl-$C_{1-3}$-alkyl, aminosulphonyl-$C_{1-3}$-alkyl, $C_{1-3}$-alkyl-aminosulphonyl-$C_{1-3}$-alkyl or di-($C_{1-3}$-alkyl)amino-sulphonyl-$C_{1-3}$-alkyl group, and wherein the heterocycles mentioned above under $R^b$- may additionally be substituted by an oxo group, $R^c$ denotes:

a hydrogen atom, a hydroxy group, a $C_{1-3}$-alkyloxy group, a methoxy group which is substituted by one to three fluorine atoms, an ethyloxy group which is substituted in the 2 position by an $R^5$ group, wherein $R^5$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, morpholin-4-yl, homomorpholin-4-yl, piperazin-1-yl or a 4-$C_{1-3}$-alkyl-piperazin-1-yl group, a propyloxy group which is substituted in the 3 position by the group $R^5$, wherein $R^5$ is as hereinbefore defined, or a butyloxy group which is substituted in the 4 position by a group $R^5$, wherein $R^5$ is as hereinbefore defined, and wherein, unless stated otherwise, the above-mentioned alkyl groups may be straight-chain or branched, a tautomer, stereoisomer, mixture thereof or physiologically acceptable salt thereof.

3. The compound of formula (I) according to claim 1, wherein $R^a$ denotes a 1-phenylethyl, 3-ethynylphenyl, 3-bromo-2-fluoro-phenyl, 3-bromo-4-fluoro-phenyl, 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 2,5-difluoro-3-methyl-phenyl, 3-chloro-2-methyl-phenyl or an indan-4-yl group, or $R^a$ denotes a 3-chloro-4-benzyloxy-phenyl, 3-chloro-4-[(3-fluoro-benzyl)oxy]-phenyl, 4-(pyridin-3-yloxy)-phenyl, 4-[(6-methyl-pyridin-3-yl)oxy]-phenyl, 3-methyl-4-(pyridin-3-yloxy)-phenyl, 3-methyl-4-[(6-methyl-pyridin-3-yl)oxy]-phenyl, 3-chloro-4-(pyridin-3-yloxy)-phenyl or 3-chloro-4-[(6-methyl-pyridin-3-yl)oxy]-phenyl group, $R^b$ denotes an azetidin-1-yl, piperazin-1-yl, 4-($C_{1-3}$-alkyl-carbonyl)-piperazin-1-yl or 4-($C_{1-3}$-alkyl-sulphonyl)-piperazin-1-yl group which may be mono- or disubstituted in each case by $R^4$, wherein the substituents may be identical or different and $R^4$ denotes:

a fluorine atom, a $C_{1-3}$-alkyl group, an amino, $C_{1-3}$-alkylamino, di-($C_{1-3}$-alkyl)amino, $C_{1-3}$-alkyl-carbonylamino, N—($C_{1-3}$-alkyl)-$C_{1-3}$-alkyl-carbonylamino, $C_{1-3}$-alkyl-sulphonylamino or N—($C_{1-3}$-alkyl)-$C_{1-3}$-alkyl-sulphonylamino group, an amino-$C_{1-3}$-alkyl, $C_{1-3}$-alkylamino-$C_{1-3}$-alkyl, di-($C_{1-3}$-alkyl)amino-$C_{1-3}$-alkyl, $C_{1-3}$-alkyl-carbonylamino-$C_{1-3}$-alkyl, N—($C_{1-3}$-alkyl)-$C_{1-3}$-alkyl-carbonylamino-$C_{1-3}$-alkyl, $C_{1-3}$-alkyl-sulphonylamino-$C_{1-3}$-alkyl or N—($C_{1-3}$-alkyl)-$C_{1-3}$-alkyl-sulphonylamino-$C_{1-3}$-alkyl group, a hydroxy, $C_{1-3}$-alkyloxy or $C_{1-3}$-alkyl-carbonyloxy group, a hydroxy-$C_{1-3}$-alkyl, $C_{1-3}$-alkyloxy-$C_{1-3}$-alkyl or $C_{1-3}$-alkyl-carbonyloxy-$C_{1-3}$-alkyl group, a $C_{1-3}$-alkyl-carbonyl, cyano, $C_{1-4}$-alkyl-oxycarbonyl, carboxy, aminocarbonyl, $C_{1-3}$-alkyl-aminocarbonyl or di-($C_{1-3}$-alkyl)amino-carbonyl group, a $C_{1-3}$-alkylcarbonyl-$C_{1-3}$-alkyl, cyano-$C_{1-3}$-alkyl, $C_{1-4}$-alkyloxycarbonyl-$C_{1-3}$-alkyl-group, aminocarbonyl-$C_{1-3}$-alkyl, $C_{1-3}$-alkylaminocarbonyl-$C_{1-3}$-alkyl or di-($C_{1-3}$-alkyl)aminocarbonyl-$C_{1-3}$-alkyl group, a $C_{1-4}$-alkylsulphanyl, $C_{1-4}$-alkylsulphinyl, $C_{1-4}$-alkylsulphonyl, aminosulphonyl, $C_{1-3}$-alkyl-aminosulphonyl or di-($C_{1-3}$-alkyl)amino-sulphonyl group, a $C_{1-4}$-alkylsulphanyl-$C_{1-3}$-alkyl, $C_{1-4}$-alkylsulphinyl-$C_{1-3}$-alkyl, $C_{1-4}$-alkylsulphonyl-$C_{1-3}$-alkyl, aminosulphonyl-$C_{1-3}$-alkyl, $C_{1-3}$-alkyl-aminosulphonyl-$C_{1-3}$-alkyl or di-($C_{1-3}$-alkyl)amino-sulphonyl-$C_{1-3}$-alkyl group, and wherein the heterocycles mentioned above under $R^b$ may additionally be substituted by an oxo group, $R^c$ denotes:

a hydrogen atom, a methoxy or ethyloxy group, an ethyloxy group which is substituted in the 2 position by the group $R^5$, wherein $R^5$ denotes a hydroxy, methoxy, ethoxy, amino, dimethylamino, diethylamino, bis-(2-methoxyethyl)-amino, pyrrolidin-1-yl, piperidin-1-yl, morpholin-4-yl, homomorpholin-4-yl, piperazin-1-yl, 4-methylpiperazin-1-yl or 4-ethylpiperazin-1-yl group, a propyloxy group which is substituted in the 3 position by the group $R^5$, wherein $R^5$ is as hereinbefore defined, or a butyloxy group which is substituted in the 4 position by the group $R^5$, wherein $R^5$ is as hereinbefore defined, and wherein, unless stated otherwise, the above-mentioned alkyl groups may be straight-chain or branched, a tautomer, stereoisomer, mixture thereof or physiologically acceptable salt thereof.

4. The compound of formula (I) according to claim 1, wherein $R^a$ denotes a 1-phenylethyl, 3-ethynylphenyl, 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 2,5-difluoro-3-methyl-phenyl, 3-chloro-2-methyl-phenyl or an indan-4-yl group, $R^b$ denotes an azetidin-1-yl, piperazin-1-yl, 4-($C_{1-3}$-alkyl-carbonyl)-piperazin-1-yl or 4-($C_{1-3}$-alkyl-sulphonyl)-piperazin-1-yl group which may be mono- or disubstituted in each case by $R^4$, wherein the substituents may be identical or different and $R^4$ denotes:

a fluorine atom, a $C_{1-3}$-alkyl group, an amino, $C_{1-2}$-alkylamino, di-($C_{1-2}$-alkyl)amino, $C_{1-2}$-alkyl-carbonylamino, N—($C_{1-2}$alkyl)-$C_{1-2}$-alkyl-carbonylamino, $C_{1-2}$-alkyl-sulphonylamino or N—($C_{1-2}$-alkyl)-$C_{1-2}$-alkyl-sulphonylamino group, an amino-$C_{1-2}$-alkyl, $C_{1-2}$-alkylamino-$C_{1-2}$-alkyl, di-($C_{1-2}$-alkyl)amino-$C_{1-2}$-alkyl, $C_{1-2}$-alkyl-carbonylamino-$C_{1-2}$-alkyl, N—($C_{1-2}$-alkyl)-$C_{1-2}$-alkyl-carbonylamino-$C_{1-2}$-alkyl, $C_{1-2}$-alkyl-sulphonylamino-$C_{1-2}$-alkyl or N—($C_{1-2}$-alkyl)-$C_{1-2}$-alkyl-sulphonylamino-$C_{1-2}$-alkyl group, a hydroxy, $C_{1-2}$-alkyloxy or $C_{1-2}$-alkyl-carbonyloxy group, a hydroxy-$C_{1-2}$-alkyl, $C_{1-2}$-alkyloxy-$C_{2-4}$-alkyl or $C_{1-2}$-alkyl-carbonyloxy-$C_{1-2}$-alkyl group, a $C_{1-2}$-alkyl-carbonyl, cyano, $C_{1-2}$-alkyl-oxycarbonyl, carboxy, aminocarbonyl, $C_{1-2}$-alkyl-aminocarbonyl or di-($C_{1-2}$-alkyl)amino-carbonyl group, a $C_{1-2}$-alkylcarbonyl-$C_{1-2}$-alkyl, cyano-$C_{1-2}$-alkyl, $C_{1-2}$-alkyloxycarbonyl-$C_{1-2}$-alkyl group, aminocarbonyl-$C_{1-2}$-alkyl, $C_{1-2}$-alkylaminocarbonyl-$C_{1-2}$-alkyl or di-($C_{1-2}$-alkyl)aminocarbonyl-$C_{1-2}$-alkyl group, a $C_{1-2}$-alkylsulphanyl, $C_{1-2}$-alkylsulphinyl or $C_{1-2}$-alkylsulphonyl group, a C$_{1-2}$-alkylsulphanyl-C$_{1-2}$-alkyl, C$_{1-2}$-alkylsulphinyl-C$_{1-2}$-alkyl or C$_{1-2}$-alkylsulphonyl-C$_{1-2}$-alkyl group, and wherein the heterocycles mentioned above under R$^b$ may additionally be substituted by an oxo group, R$^c$ denotes:

a hydrogen atom, a methoxy, ethyloxy or 2-(methoxy)-ethyloxy group, a 2-(morpholin-4-yl)ethyloxy, 3-(morpholin-4-yl)propyloxy or 4-(morpholin-4-yl)butyloxy group, a tautomer, stereoisomer, mixture thereof or physiologically acceptable salt thereof.

5. The compound of formula (I) according to claim 1, wherein

R$^a$ denotes a 1-phenylethyl, 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 3-fluoro-5-methyl-phenyl, 4-fluoro-3-methyl-phenyl, 2,4-difluoro-3-methyl-phenyl, 3-chloro-2-methyl-phenyl or an indan-4-yl group, R$^b$ denotes an azetidin-1-yl or 3-oxo-piperazin-1-yl group which may be mono- or disubstituted in each case by R$^4$, wherein the substituents may be identical or different and R$^4$ denotes a methyl, hydroxy, cyano, aminocarbonyl, methylamino-carbonyl or dimethylamino-carbonyl group, and R$^c$ denotes a methoxy group, a tautomer, stereoisomer, mixture thereof or physiologically acceptable salt thereof.

6. A compound according to claim 1 selected from:

(a) 4-[(3-chloro-2-fluoro-phenyl)amino]-6-[cis-4-(3-oxo-piperazin-1-yl)-cyclohexyloxy]-7-methoxy-quinazoline, (b) 4-[(3-chloro-2-fluoro-phenyl)amino]-6-[trans-4-(3-oxo-piperazin-1-yl)-cyclohexyloxy]-7-methoxy-quinazoline, (c) 4-[(3-chloro-2-fluoro-phenyl)amino]-6-[trans-4-(4-methyl-3-oxo-piperazin-1-yl)-cyclohexyloxy]-7-methoxy-quinazoline, (d) 4-[(2-fluoro-3-methyl-phenyl)amino]-6-[trans-4-(3-oxo-piperazin- 1-yl)-cyclohexyloxy]-7-methoxy-quinazoline, (e) 4-[(2-fluoro-5-methyl-phenyl)amino]-6-[trans-4-(3-oxo-piperazin- 1-yl)-cyclohexyloxy]-7-methoxy-quinazoline, (f) 4-[(2,4-difluoro-3-methyl-phenyl)amino]-6-[trans-4-(3-oxo-piperazin-1-yl)-cyclohexyloxy]-7-methoxy-quinazoline and (g) 4-[(3-chloro-2-methyl-phenyl)amino]-6-[trans-4-(3-oxo-piperazin-1-yl)-cyclohexyloxy]-7-methoxy-quinazoline or a physiologically acceptable salt thereof.

7. A pharmaceutical composition comprising the compound according to claim 1, or a physiologically acceptable salt thereof, optionally together with one or more inert carriers and/or diluents.

8. A pharmaceutical composition comprising the compound according to claim 6, or a physiologically acceptable salt thereof, optionally together with one or more inert carriers and/or diluents.

9. A process for preparing a compound according to claim 1, comprising:

(a) reacting a compound of formula (II)

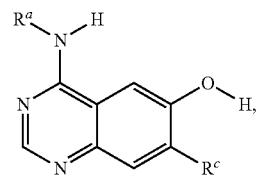

(II)

wherein R$^a$ and R$^c$ are as hereinbefore defined, with a compound of formula (III)

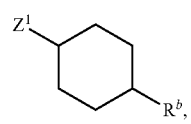

(III)

wherein R$^b$ is as hereinbefore defined and Z$^1$ denotes a leaving group, or b) reacting a compound of formula (IV)

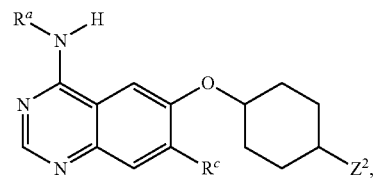

(IV)

wherein R$^a$ and R$^c$ are as hereinbefore defined, and Z$^2$ denotes a leaving group, with a compound of general formula

H—R$^b$, (V)

Wherein R$^b$ is as hereinbefore defined, or c) reacting a compound of formula (VI)

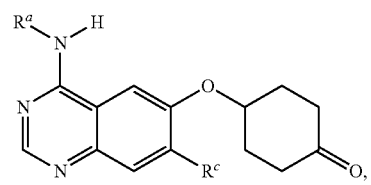

(VI)

wherein R$^a$ and R$^c$ are as hereinbefore defined, with a compound of general formula

H—R$^b$ (VII), wherein $R^b$ is as hereinbefore defined, or d) reacting a compound of formula (VIII)

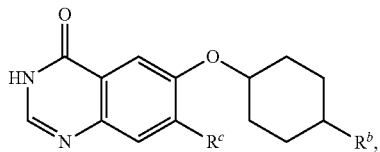
(VIII)

wherein $R^b$ and $R^c$ are as hereinbefore defined,
with a halogenating agent to form an intermediate compound of formula (IX),

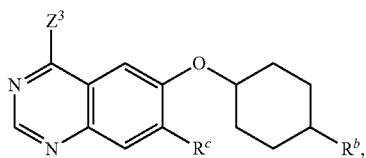
(IX)

wherein $R^b$ and $R^c$ are as hereinbefore defined and $Z^3$ denotes a halogen atom, and reacting said intermediate compound of formula (IX) with a compound of general formula (X), $$R^a—NH_2 \qquad (X),$$

wherein $R^a$ is as hereinbefore defined.

* * * * *